US012209257B2

(12) United States Patent
Brown et al.

(10) Patent No.: US 12,209,257 B2
(45) Date of Patent: Jan. 28, 2025

(54) SYSTEM AND METHOD TO DETERMINE CRITICAL PROCESS PARAMETERS FOR A CONTINUOUS VIRAL INACTIVATION REACTOR TO DESIGN AND MANUFACTURE SAME

(71) Applicant: Boehringer Ingelheim International GmbH, Ingelheim am Rhein (DE)

(72) Inventors: Matthew R. Brown, Sunnyvale, CA (US); Jonathan Coffman, Gaithersbury, CA (US); Raquel Orozco, Richmond, CA (US)

(73) Assignee: Boehringer Ingelheim International GmbH, Ingelheim Am Rhein (DE)

( * ) Notice: Subject to any disclaimer, the term of this patent is extended or adjusted under 35 U.S.C. 154(b) by 907 days.

(21) Appl. No.: 17/283,286

(22) PCT Filed: Oct. 2, 2019

(86) PCT No.: PCT/US2019/054216
§ 371 (c)(1),
(2) Date: Apr. 7, 2021

(87) PCT Pub. No.: WO2020/076575
PCT Pub. Date: Apr. 16, 2020

(65) Prior Publication Data
US 2021/0388323 A1    Dec. 16, 2021

Related U.S. Application Data

(60) Provisional application No. 62/742,506, filed on Oct. 8, 2018.

(51) Int. Cl.
*C12N 7/08* (2006.01)
*B01L 3/00* (2006.01)
(Continued)

(52) U.S. Cl.
CPC .......... *C12N 7/08* (2013.01); *B01L 3/502715* (2013.01); *C12M 23/16* (2013.01);
(Continued)

(58) Field of Classification Search
CPC ...... C12M 23/06; C12M 23/16; C12M 41/48; C12M 47/12; B01L 2200/0647;
(Continued)

(56) References Cited

U.S. PATENT DOCUMENTS 6,586,172 B1    7/2003 Gunn et al.
2006/0045796 A1    3/2006 Anderle et al.
(Continued)

FOREIGN PATENT DOCUMENTS

CA    3058647 A1 * 10/2018    .............. C07K 1/20
CN    106163576 A    11/2016
(Continued)

OTHER PUBLICATIONS

Amarikwa et.al., "Impact of Dean Vortices on the Integrity Testing of a Continuous Viral Inactivation Reactor", May 2018, Biotechnology Journal, vol. 14, No. 2, p. 1700726.
(Continued)

*Primary Examiner* — Jennifer Wecker
(74) *Attorney, Agent, or Firm* — Shelley A. Jones

(57) ABSTRACT

A viral inactivation device including at least one experimental continuous viral inactivation reactor having at least an inlet, an outlet, and a tubular flow path and a computer system that, based on the experimental continuous viral inactivation reactor can design, select, make, and/or manufacture a scaled actual reactor. The tubular flow path includes a set of alternating turns that form a serpentine or an interwoven pattern between the inlet and the outlet.

12 Claims, 60 Drawing Sheets

(51) Int. Cl.
*C12M 1/36* (2006.01)
*C12M 3/06* (2006.01)
*G01N 11/02* (2006.01)
*G16B 40/00* (2019.01)

(52) U.S. Cl.
CPC ...... *C12M 41/48* (2013.01); *B01L 2200/0647* (2013.01); *B01L 2300/0627* (2013.01); *B01L 2300/0883* (2013.01); *B01L 2400/0406* (2013.01); *C12N 2795/14261* (2013.01); *G01N 11/02* (2013.01); *G16B 40/00* (2019.02)

(58) Field of Classification Search
CPC ..... B01L 2300/0627; B01L 2300/0883; B01L 2400/0406; B01L 3/502715; C12N 2795/14261; C12N 7/00; C12N 7/08; G01N 11/02; G16B 40/00
See application file for complete search history.

(56) References Cited

U.S. PATENT DOCUMENTS

| | | | | |
|---|---|---|---|---|
| 2014/0356270 | A1* | 12/2014 | Shmayda | C01B 4/00 422/111 |
| 2016/0375159 | A1 | 12/2016 | Lobedann et al. | |
| 2017/0198246 | A1* | 7/2017 | Niazi | C12M 23/26 |
| 2019/0022615 | A1 | 1/2019 | El-Toufaili et al. | |

FOREIGN PATENT DOCUMENTS

| | | |
|---|---|---|
| CN | 108495706 A | 9/2018 |
| CN | 113015787 | 6/2021 |
| CN | 113039265 A | 6/2021 |
| CN | 117298305 A | 12/2023 |
| WO | 2016116947 A1 | 7/2016 |
| WO | 2020076681 A1 | 4/2020 |
| WO | 2020076683 A1 | 4/2020 |

OTHER PUBLICATIONS

Orozcp et.al., "Design construction, and optimization of a novel, modular, and scalable incubation chamber for continuous viral inactivation", 2017, Biotechnology Progress, 2017, vol. 33, No. 4, pp. 954-965.

Parker et.al., "Design of a novel continuous flow reactor for low pH viral inactivation", Biotechnology and Bioengineering, 2018, vol. 115, No. 3, pp. 606-616.

International Search Report and Written Opinion for corresponding application, PCT/US2019/054216, date of mailing Jan. 2, 2020.

* cited by examiner

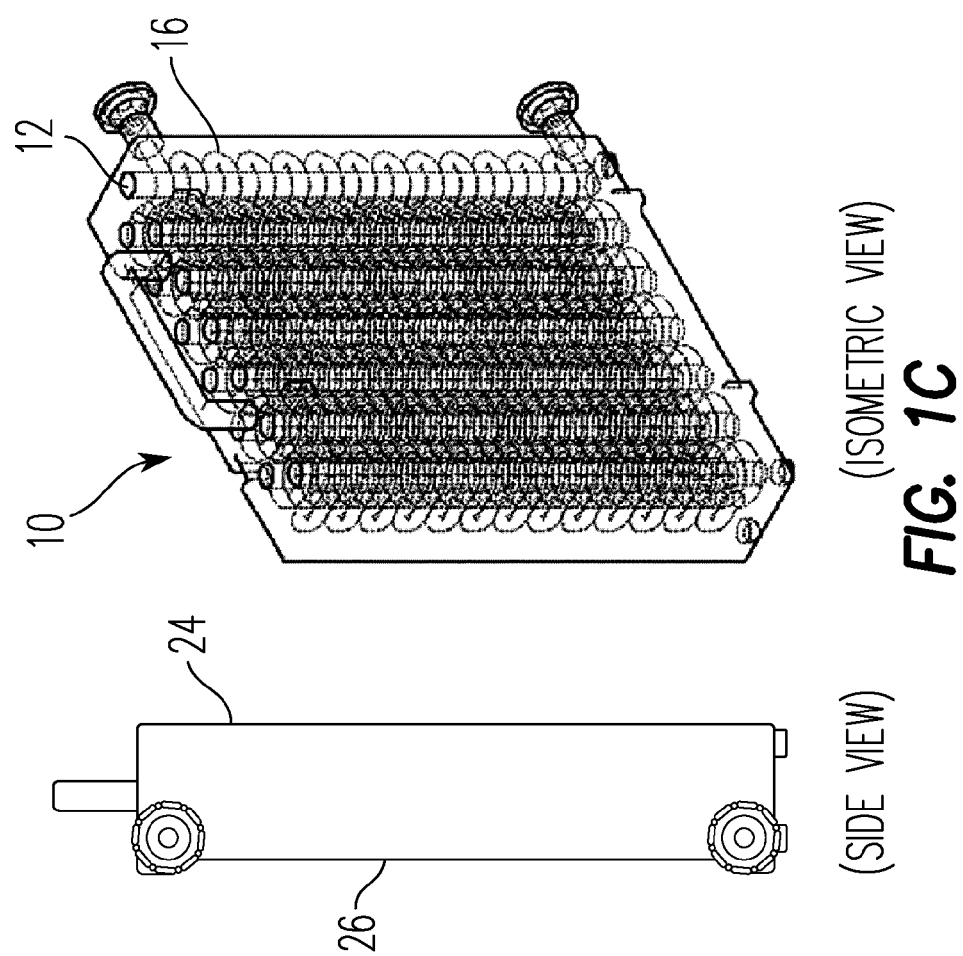

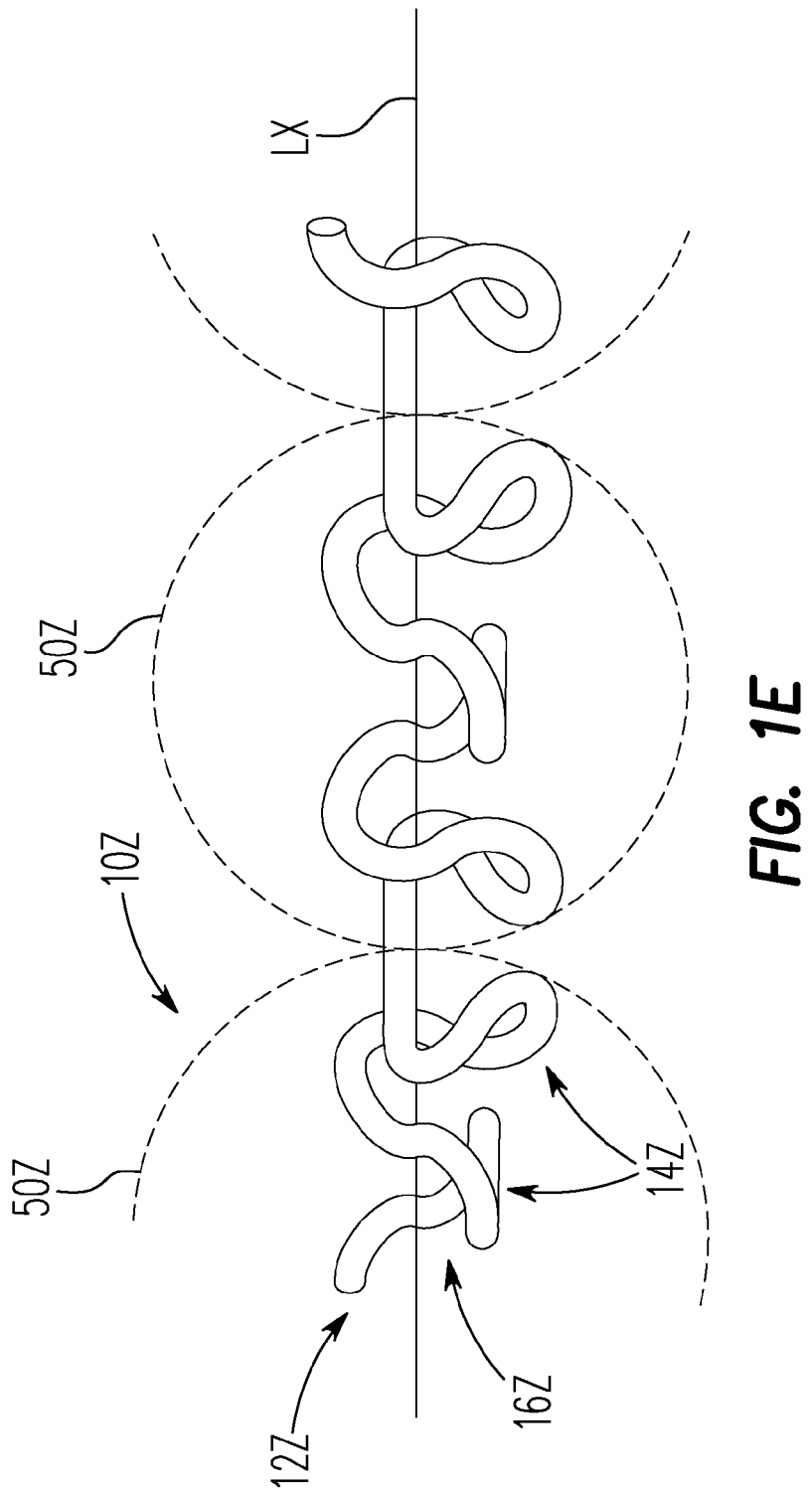

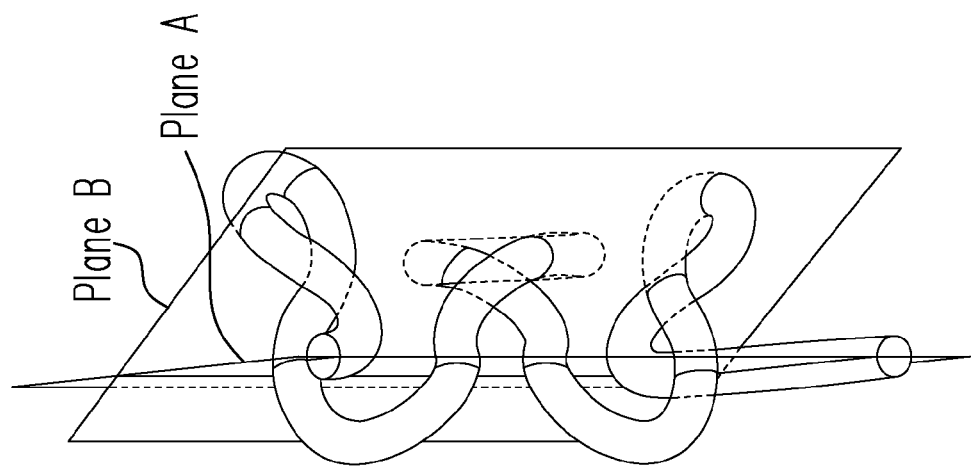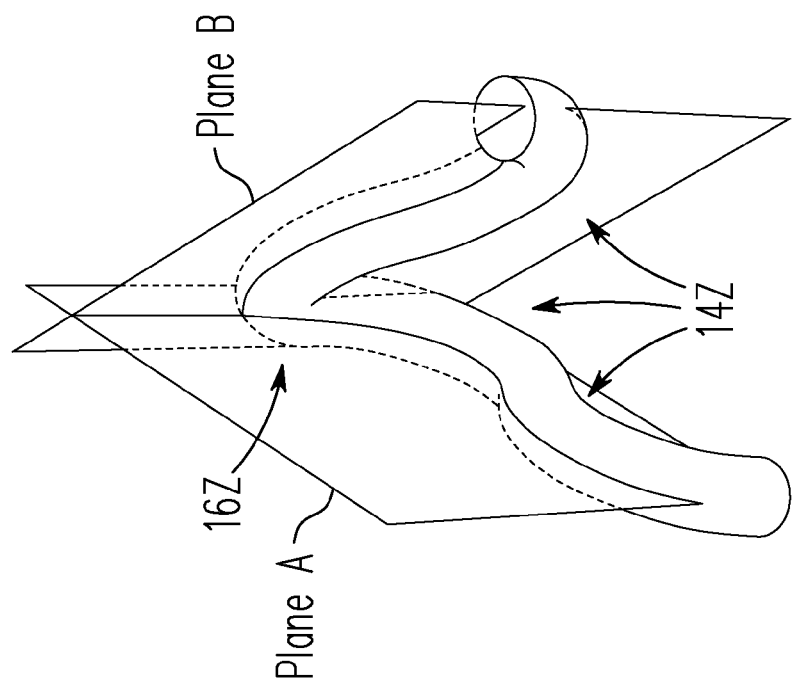
FIG. 1F

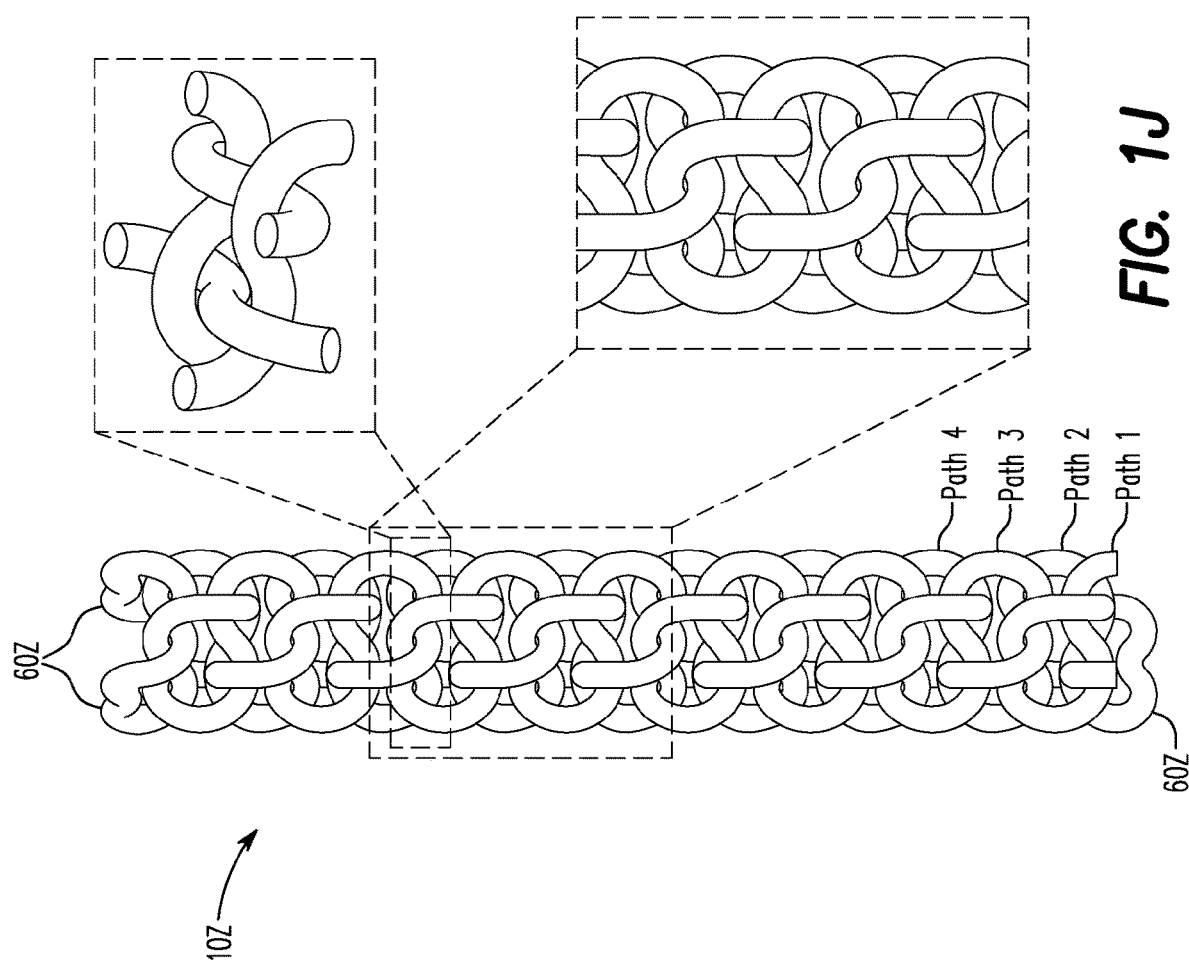

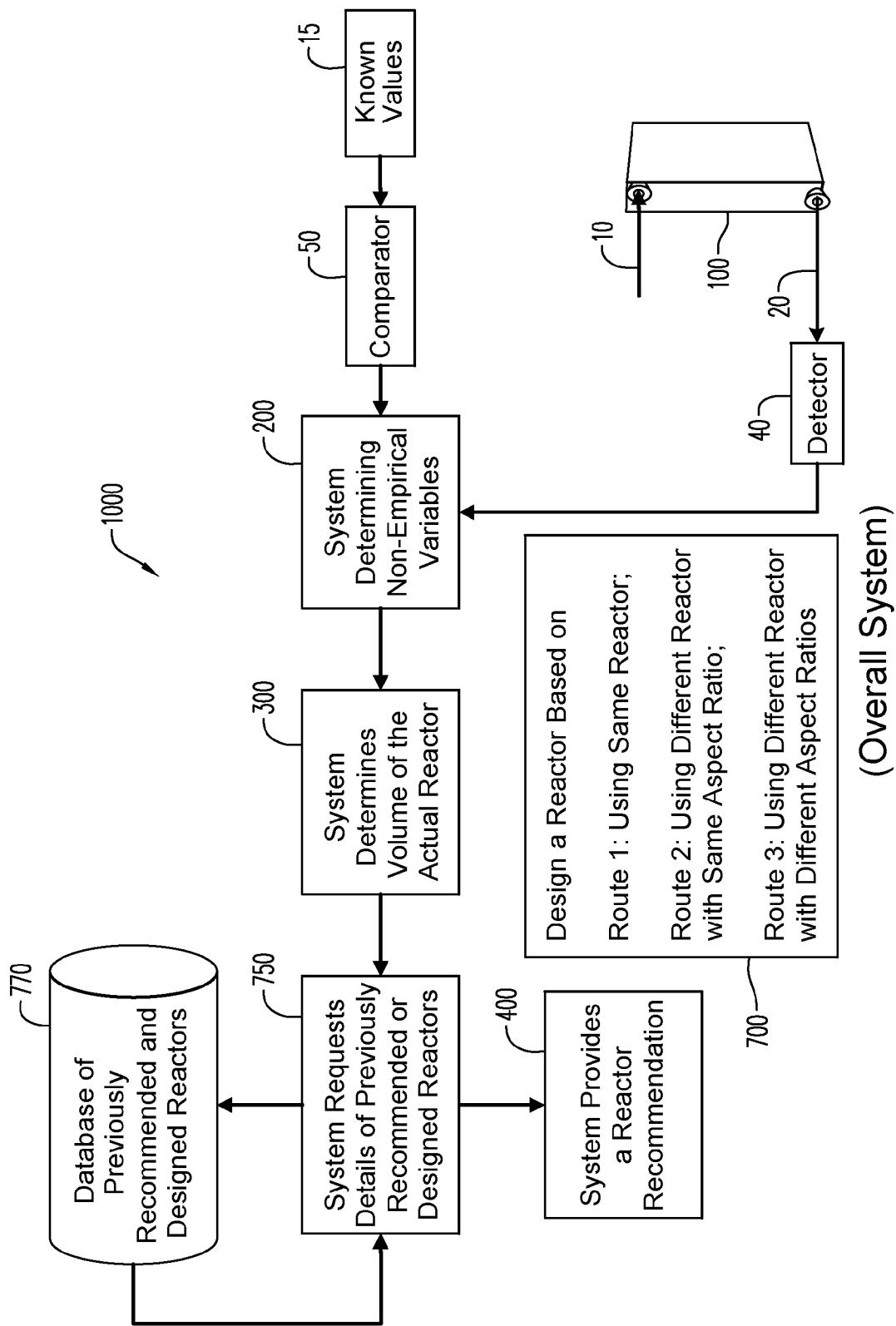
FIG. 9 (Overall System)

SYSTEM AND METHOD TO DETERMINE CRITICAL PROCESS PARAMETERS FOR A CONTINUOUS VIRAL INACTIVATION REACTOR TO DESIGN AND MANUFACTURE SAME

CROSS-REFERENCE TO RELATED APPLICATION

This application claims the benefit of U.S. Provisional Application No. 62/742,506, filed on Oct. 8, 2018, the content of which is expressly incorporated herein by reference thereto.

FIELD OF THE INVENTION

The present disclosure generally relates to a system and a method to determine critical process parameters for a continuous viral inactivation reactor and to design and manufacture the same.

BACKGROUND OF THE INVENTION

Presently, defining the residence time of the viral particles in a plug-flow-reactor (PFR) is difficult to quantify due to fluid dynamics phenomena that occur during flow of a process stream in circular piping where the flow of a process stream in the center of the pipe can be twice as fast as the average flow of the process stream and almost stagnant near the wall of the pipe. Thus, presently the only way to determine the correct PFR parameters for viral inactivation is by experimentation. This trial-and-error approach is inefficient and time-consuming.

SUMMARY OF THE INVENTION

In an aspect, a method for designing, selecting, making, and/or manufacturing of an actual plug-flow reactor is described. The method includes introducing a process stream including detectable particles/tracer into an experimental reactor having a known radius of curvature and a known internal diameter, wherein the experimental reactor is in communication with at least one of a first detector and a second detector; detecting a flow rate of the process stream in the experimental reactor by at least one of the first detector and the second detector; detecting fluid-phase parameters of the process stream by at least one of the first detector and the second detector; detecting the detectable particles/tracer exiting the experimental reactor by the second detector; determining, based on the introduced process stream including the detectable particles/tracer, empirical values relating to at least one of experimental reactor parameters and fluid-phase parameters; determining non-empirical values relating to at least one of the experimental reactor parameters and the fluid-phase parameters; and designing, selecting, making, and/or manufacturing the actual reactor based on the determined empirical values and the determined non-empirical values.

In an aspect, a system to determine, select, make, and/or manufacture an actual reactor size is described. The system comprises a processor; and a non-transitory machine-readable storage medium storing machine-readable instructions that are executable by the processor to receive parameters of an experimental reactor that is in communication with at least one of a first detector and a second detector; detect flow rate of a process stream including detectable particles/tracer in the experimental reactor by at least one of the first detector and the second detector; detect fluid-phase parameters of the process stream in the experimental reactor by at least one of the first detector and the second detector; detect the detectable particles/tracer exiting the experimental reactor by the second detector; determine empirical values of at least one of reactor parameters of the experimental reactor and fluid parameters of the process stream; determine non-empirical values of at least one of the reactor parameters of the experimental reactor and the fluid parameters of the process stream; design, select, make, and/or manufacture an actual reactor for an actual process stream having a predetermined volume of fluid, wherein the fluid includes substantially similar parameters as the fluid parameters in the experimental reactor.

In another aspect, a system for designing, selecting, making, and/or manufacturing an actual reactor for continuously inactivating virus during manufacturing of a biological product is described. The system comprises an experimental reactor having a known radius of curvature and a known diameter and designed to receive a process stream; at least one of a first detector and a second detector in communication with the experimental reactor, wherein the at least one of the first detector and the second detector detects fluid-phase parameters of the process stream and wherein the second detector detects detectable particles/tracer exiting the experimental reactor; a processor; and a non-transitory machine-readable storage medium storing machine-readable instructions that are executable by the processor to: determine empirical values corresponding to parameters of at least one of the experimental reactor and fluid of the process stream; determine non-empirical values corresponding to parameters of at least one of the experimental reactor and fluid of the process stream; and based on the determined empirical values and the determined non-empirical values, design, select, make, and/or manufacture the actual reactor for an actual process stream having a predetermined volume of fluid.

In a further aspect, a system for designing, selecting, making, and/or manufacturing an actual reactor for continuously inactivating virus during manufacturing of a biological product is provided. The system comprises an experimental reactor having an inlet, an outlet, and a tubular flow path comprising a set of alternating turns that form a serpentine pattern between the inlet and the outlet, wherein the serpentine pattern includes a predetermined radius of curvature and a predetermined diameter and wherein the experimental reactor is designed to receive a process stream; at least one of a first detector and a second detector in communication with the experimental reactor, wherein the at least one of the first detector and the second detector detects fluid-phase parameters of the process stream and wherein the second detector detects detectable particles/tracer exiting the experimental reactor; a processor; and a non-transitory machine-readable storage medium storing machine-readable instructions that are executable by the processor to: determine empirical values of at least one of the experimental reactor parameters and the fluid parameters of the process stream; determine non-empirical values of at least one of the reactor parameters of the experimental reactor and the fluid parameters of the process stream; and design, select, make, and/or manufacture the actual reactor based on the determined empirical values and the determined non-empirical values, wherein the actual reactor includes a serpentine pattern substantially similar to the serpentine pattern of the experimental reactor, but configured to accommodate an actual process stream having a predetermined volume of fluid.

In yet another aspect, a system for designing, selecting, making, and/or manufacturing an actual reactor for continuously inactivating virus during manufacturing of a biological product is provided. The system comprises an experimental reactor having an inlet, an outlet, and at least one interwoven tubular flow path comprising a plurality of turns that are in different, non-parallel planes; at least one of a first detector and a second detector in communication with the experimental reactor, wherein the at least one of the first detector and the second detector detects fluid-phase parameters of the process stream and wherein the second detector detects detectable particles/tracer exiting the experimental reactor; a processor; and a non-transitory machine-readable storage medium storing machine-readable instructions that are executable by the processor to: determine empirical values of at least one of the experimental reactor parameters and the fluid parameters of the process stream; determine non-empirical values of at least one of the reactor parameters of the experimental reactor and the fluid parameters of the process stream; and design, select, make, and/or manufacture the actual reactor based on the determined empirical values and the determined non-empirical values, wherein the actual reactor includes an interwoven tubular flow path substantially similar to the interwoven tubular flow path of the experimental reactor, but designed and configured to accommodate an actual process stream having a predetermined volume of fluid.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

The present disclosure in its several aspects and embodiments can be more fully understood from the detailed description and the accompanying drawings, wherein:

FIG. 1C is a side view and an isometric view of the continuous tubular reactor, according to an example of the present disclosure;

FIG. 1E is an isometric view of an exemplary continuous flow reactor tube having a single run, according to an example of the present disclosure;

FIG. 1F illustrates the continuous flow reactor tube of FIG. 1E having turns on a single longitudinal axis, but in different, non-parallel planes, according to an example of the present disclosure;

FIG. 1J is an isometric view of an exemplary continuous flow tube having four runs, according to an example of the present disclosure, according to an example of the present disclosure;

FIG. 9 illustrates another exemplary system, according to an example of the present disclosure;

Throughout this specification and figures like reference numbers identify like elements.

DETAILED DESCRIPTION OF THE INVENTION

Figure 1A:
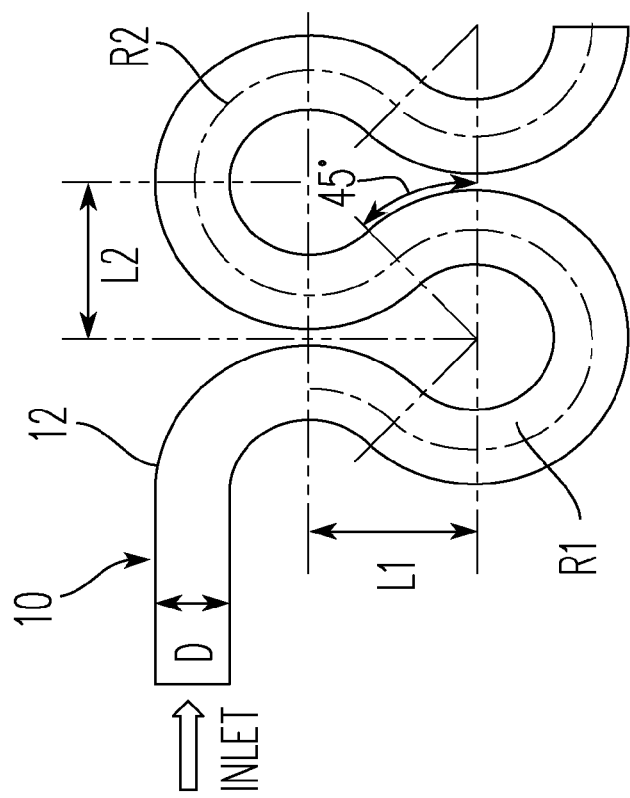
FIG. 1A is a top view of a tubular flow path of a continuous tubular reactor, according to an example of the present disclosure.

It is to be understood that both the foregoing general description and the following detailed description are exemplary and explanatory only, and are intended to provide an explanation of various embodiments of the present teachings.

In the description below, the phrase "experimental reactor" refers to a reactor that is used for non-commercial purposes, such as low volume runs, mock runs, initial data gathering, etc. Additionally, the phrase "actual reactor" refers to a reactor that is used for any other purposes that the experimental reactor is not used. Such purposes include, for example, commercial purposes. Furthermore, the phrase "hypothetical reactor" refers to an experimental reactor, wherein its data was previously collected, thus, there is no reason to conduct the experiment again. The phrases "first detector" and "second detector" refer to one or more detectors capable of detecting different characteristics of the process stream and its content.

Overall View

In an example, the process for manufacturing a biological product can include continuous viral inactivation, using a PFR, by continuously adding and homogenizing a viral inactivating agent to a product containing feed stream (process stream). From there, the process stream can be pumped through and/or introduced to the PFR and maintained at this viral inactivating condition for a predetermined amount of time. Defining the residence time of the viral particles in a PFR is difficult to quantify due to the flow of the process stream in the center of the pipe being twice as fast as the average flow of the process stream and almost stagnant near the wall of the pipe. To determine an optimum residence time of the viral particles, a new design or manufactured PFR can include a set of alternating turns that form a serpentine pattern between an inlet and an outlet, thus creating a serpentine-like flow path, interwoven path, and/or a Jig-in-a-Box (JIB) design that generates Dean Vortices to promote radial mixing can be utilized, as described in commonly owned and co-pending U.S. patent applications entitled "A Novel Continuous Flow Reactor For Low pH Viral Inactivation" and "Continuous Flow Reactor for Viral Inactivation" the specifications of which are incorporated herein by reference. In this new design or manufactured PFR, the ability to predict when the first viral particle exits the reactor is essential. Generally, three alternative approaches may be used to determine or estimate a minimum residence time experienced by a discrete detectable particle or detectable tracer equivalent to an incubation time for batch viral inactivation ($T_{min}$). One approach assumes ideal uniformity in the flow path (i.e. plug flow) and simply divides the reactor volume by the flow rate. However, this idealistic approach can result in underestimating the required residence time, even with the increasing efficiency of the reactor having a serpentine-like flow path or an interwoven flow path. Another approach is to assume that the center of the flow path remains twice as fast as the average velocity of the process stream. This approach, however, can result in overestimating the required residence time of the process stream resulting from the increased efficiency of the serpentine-like or interwoven reactor. Another approach uses process development to determine an efficiency coefficient by which to modify the idealistic approach to account for non-idealities. However, this approach requires testing of an at-scale JIB and fails to account for potential anomalies in viscosity and flow rates. Thus, the system and method of the present invention use an inventive technological solution to accurately extrapolate JIB performance across path lengths, flowrates, reactor designs, internal diameters, and viscosities.

Being able to predict $T_{min}$ allows for the estimation and/or configuration of the desired flow rates and reactor size required to fit a process.

Figure 2A:
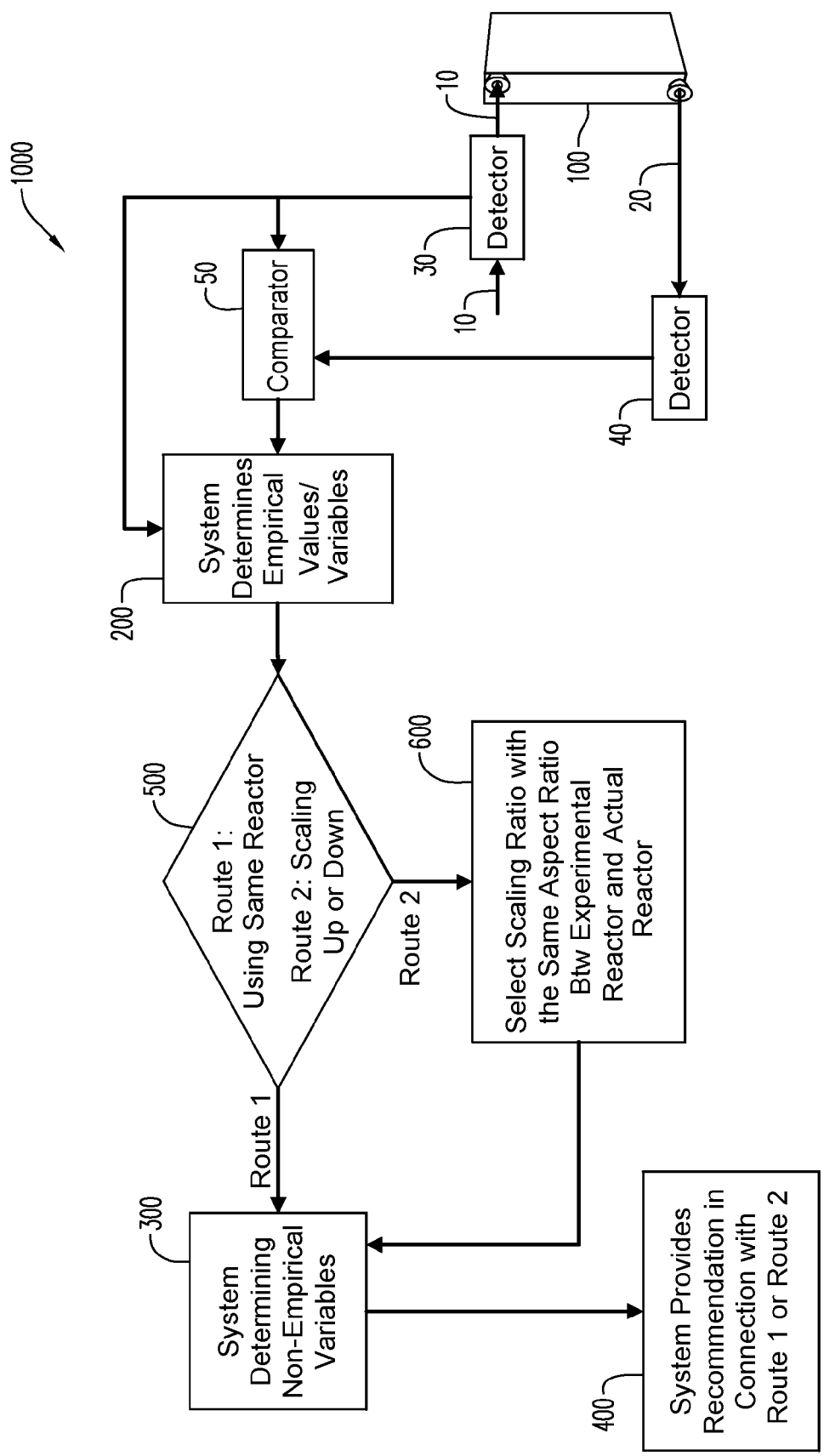
FIG. 2A illustrates an exemplary system, according to an example of the present disclosure.
Figure 3:
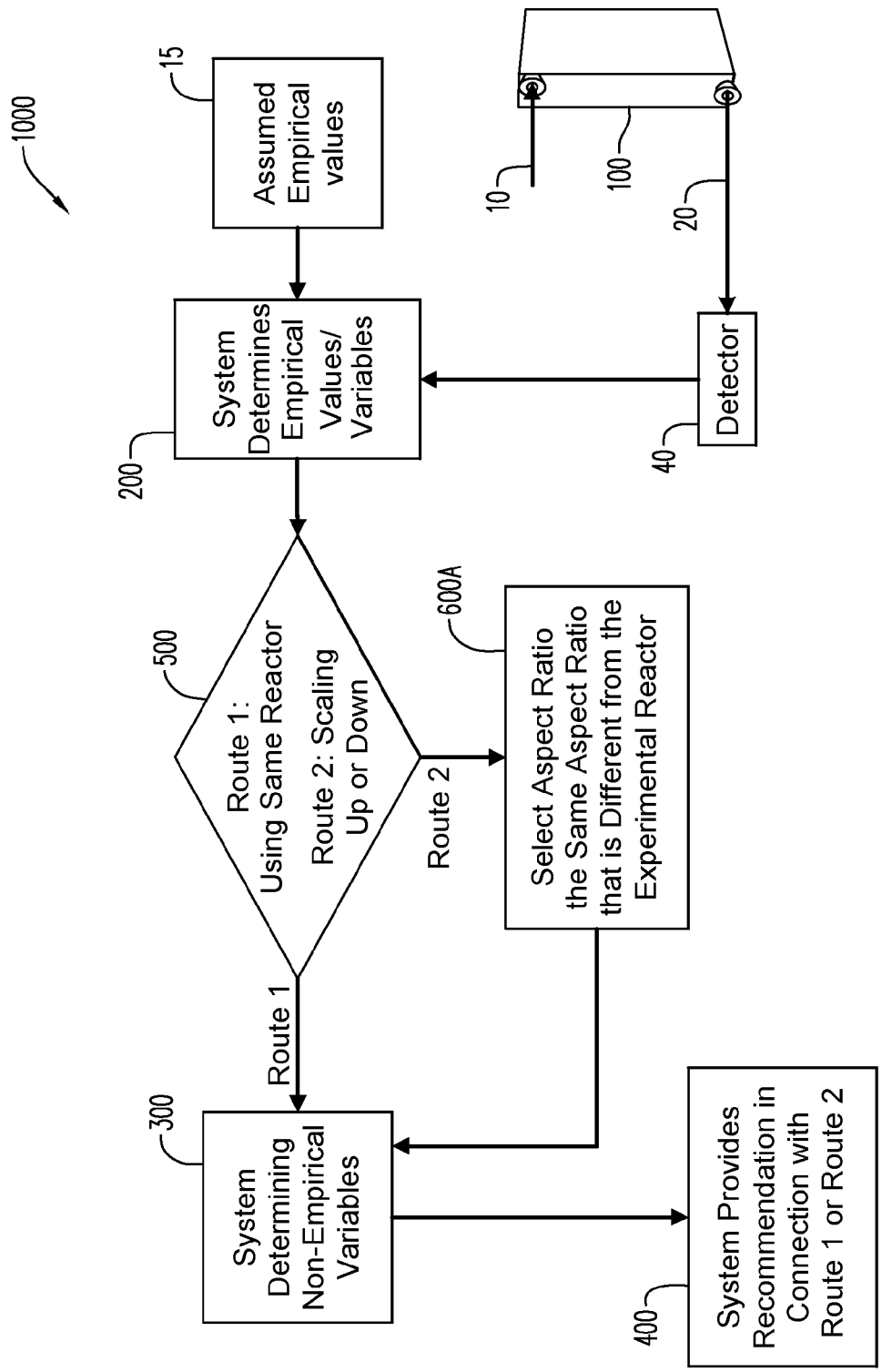
FIG. 3 illustrates another exemplary system, according to an example of the present disclosure.

This is especially useful when submitting data to regulatory agencies, such as the Food and Drug Administration (FDA), where compliance with applicable regulations requires data verification. The systems below will allow a user to run a small scale process stream for data verification purposes and then scale the reactor for mass production, without compromise to the process stream or final results of the process stream during scale-up. Given that the viral inactivating conditions can also degrade the target product as a function of residence time, maximum residence time ($T_{max}$) spent in the reactor (i.e., maximum residence time experienced by the last significant amount of target product leaving the reactor) should also be determined. The present invention is the first known approach to account for the target product stability. The first application of the system and method allows the use of $T_{min}$ and $T_{max}$ to solve for the operational flow rate and the path length of the JIB. The second application takes the opposite approach, in that the operational flow rate and path length are used to predict the $T_{min}$ and $T_{max}$. The third application is a way to approximate the internal diameter and path length required for a certain $T_{min}$ when scaling the size of the reactor. In each of these applications, the impact of viscosity, Dean Number, and reactor volume on the residence time distribution are to be determined and quantified. In each of these applications, a user can select if the user would like to use a reactor having a substantially same diameter or a reactor with a different diameter (i.e., scaling the reactor). Alternatively or additionally, the system can recommend whether a same size reaction tube reactor should be used in the actual process as in the experimental reactor or if the experimental reactor should be scaled up or down. In this alternative or additional example, when the reactor is being scaled up or down, the system or the user can select that the experimental reactor and the actual reactor have the same aspect ratio, as shown in FIG. 2A, or that the experimental reactor and the actual reactor have different aspect ratios, as shown in FIG. 3.

Continuous Flow Reactor Having a Tubular Flow Path with a Set of Alternating Turns that Form a Serpentine Pattern As stated above, the system can design, select, make, and/or manufacture an actual reactor having a reactor tube with a serpentine pattern. The details of the serpentine pattern are described in FIGS. 1A-1D. Referring to FIG. 1A, each curve 10 in the tubular flow path 12 can include a vertical (L1) center to center distance between the turns of approximately 1.5 cm, such as about 1.479 cm. Additionally, each curve 10 can include a horizontal (L2) center to center distance between the turns of about 1.375 cm. Furthermore, the radius of each curve 10 in the tubular flow path 12 can be substantially constant. In an example, when the ROC is from about 0.85 cm to about 0.99 cm, then the angle of the curvature in each curve 10 can be about 270°. In another example, the ROC is greater than or equal to about 0.99 cm, then the angle of curvature of each curve can be the same or the angle of the curvature of the first curve 10 can be about 270° and the angle of the curvature of the second curve 10 adjacent to the first curve can be equal or greater than 270°. In each exemplary scenario described, above, R1 and R2 can be within 0.05 cm of each other to prevent substantial differences in the Dean Number between alternating turns.

In an example, each curve 10 in the tubular flow path 12 can include the same radius, such as a radius of 1 cm. In another example, each curve 10 in the tubular flow path 12 can include a different radius. For example, the first curve 10 can include a radius R1, which can be 1 cm and the second curve 10 can include a radius R2, which can be 1.02 cm. In this example, the angle of the curvature corresponding to the radius R1 can be about 270° and the angle of the curvature corresponding to the radius R2 can be about 278.27°. In another example, the first half of a curve 10 in each tubular flow path 12 can include a first radius R1, which can be 1 cm and the second half of the curve 10 in each tubular flow path 12 can include a second radius R2, which can be 1.02 cm.

Figure 1B:
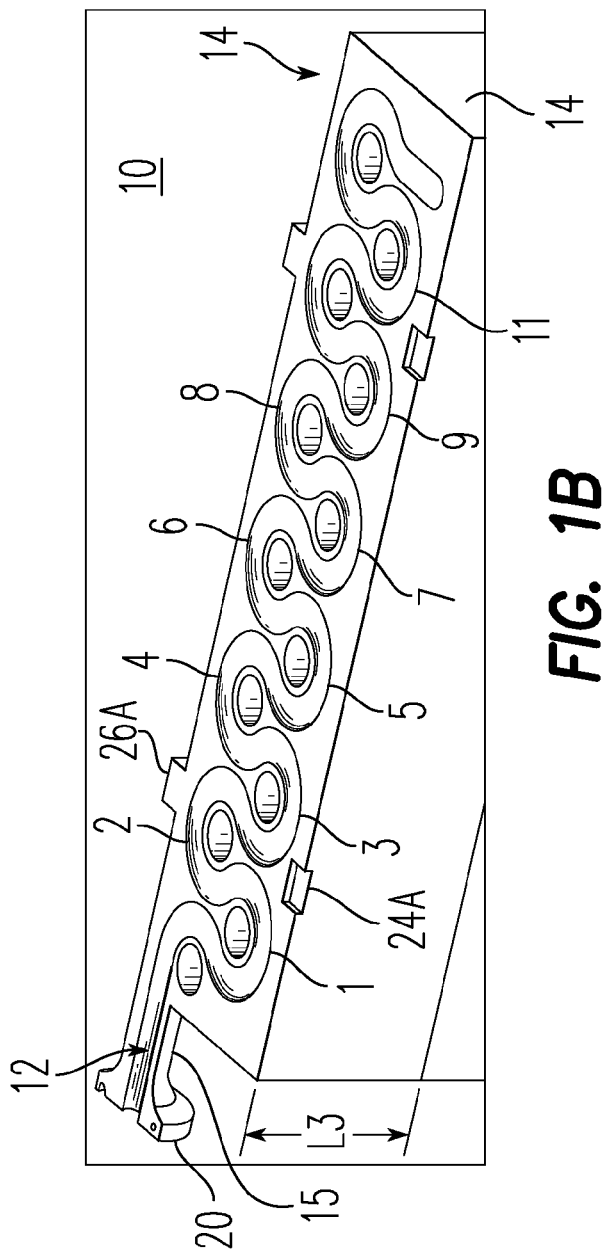
FIG. 1B is a partial perspective view of a continuous tubular reactor, according to an example of the present disclosure.

Referring to FIGS. 1B and 1C, to accommodate approximately 325 alternating 270° turns into a compact design, the tubular flow paths 12 in the in-line tubular CVI reactor 10 can be segmented vertically into a plurality of stacked layers 14, such as from 2 layers 14 to 26 layers 14 or more, for example, 26 layers 14, as shown in FIG. 1C. Each layer in the plurality of stacked layers 14 may include a thickness of from about 0.5 cm or less to about 2 cm or more, such as from about 0.7 cm to about 1.2 cm. In an example, each layer 14(a)-14(z) in the stacked layers 14 can include from about 10.5 turns or less to about 15.5 turns or more in a single plane. For example, each layer 14(a)-14(z) in the stacked layers 14 can include 12.5 turns. In an example, each layer 14 can be connected to its adjacent lower layer 14 by a 180° vertical turn 16. Alternatively, a second half of the last turn 10 of the flow path 12 in each layer 14 can be turned vertically by 180° to connect the tubular flow path 12 in the first layer (e.g., layer 14(a)) to the tubular flow path 12 in the second layer 14(b)). In an example, where the in-line tubular CVI reactor 10 includes 26 layers 14, the 26 layers 14 can be connected to one another by 25 180° vertical turns 16.

Referring to FIG. 1B, in an example, each layer 14 in the in-line tubular CVI reactor 100 can include a depth L3. The depth L3 can be a distance from a center of the tubular flow path 12 in a first layer 14 to the center of the tubular flow path 12 in a second layer 14 directly below the first layer 14. The depth L3 can be from about 0.7 cm or less to about 1.2 cm or more, for example from about 0.8 cm to about 0.9 cm, such as a depth of about 0.835 cm. In an example, the distance from the bottom portion of the tubular flow path 12 in a first layer to the top portion of the tubular flow path 12 in a second layer directly below the first layer can be from about 0.15 cm (1.5 mm) to about 0.4 cm (4 mm), for example, it can be from about 0.17 cm (1.7 mm) to about 0.255 cm (2.55 mm), such as about 0.2 cm (2 mm).

Figure 1D:
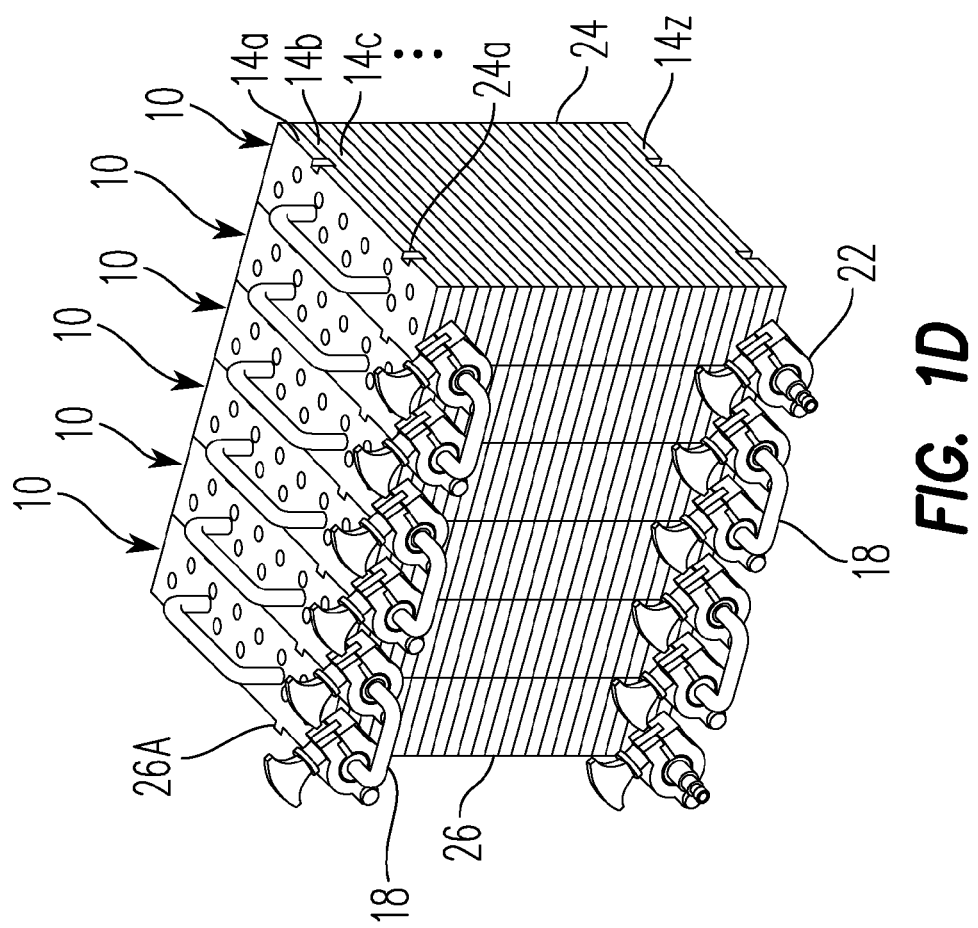
FIG. 1D illustrates a plurality of continuous tubular reactors connected to one another, according to an example of the present disclosure.

In an example, as shown in FIG. 1D, to allow for alterations to the path length and incubation time, in addition to the in-line tubular CVI reactor 10 having a plurality of layers 14, a plurality of in-line tubular CVI reactor 10 can be connected to one another in series. This can be accomplished by one or more flanged connectors 18. In an example, at least 2 in-line tubular CVI reactor 10 can be connected to one another, such as at least 6 in-line tubular CVI reactor 10 or more. In this particular example, the tubular flow path 12 at each end of the in-line tubular CVI reactor 10 can partially extend out (extended section 15) from the in-line tubular CVI reactor 100. The extended section 15 can also include a flange 20, as shown in FIG. 1B. A connector 18 can include a horizontal 180° turn and/or be in a shape of a "U." One end of the connector 18 can be connected to the tubular flow path 12 or the flange 20 of a first-in-line tubular CVI reactor 10 and the second end of the connector 18 can be connected to the tubular flow path 12 or the flange 20 of an adjacent in-line tubular CVI reactor 10.

The connector 18 can be connected to each tubular flow path 12 or flange 20 by a clamp 22, as shown in FIG. 1D, or by other fastener devices, such as a screw, an adhesive, etc. In an example, a gasket can be placed between the end of the tubular flow path 12 or flange 20 and each end of the connector 18.

In an example, the in-line tubular CVI reactor 10 can include a body or footprint of 20×4.9×23 cm and can contain a flow path 12 length of approximately 16.43 m resulting in approximately a 520 ml flow volume. The body of the in-line tubular CVI reactor 10 can include a first side 24 and a second side 26, as shown in FIG. 1C. In an example, the first side 24 can include at least one groove or indentation 24A and the second side 26 can include at least one protrusion 26A. The at least one indentation 24A and the at least one protrusion 26A can be arranged such that when two in-line tubular CVI reactors 10 are facing one another they are aligned and can secure one in-line tubular CVI reactors 10 to an adjacent in-line tubular CVI reactor 10.

Continuous Flow Reactor Having an Interwoven Tubular Flow Path

Figure 1G:
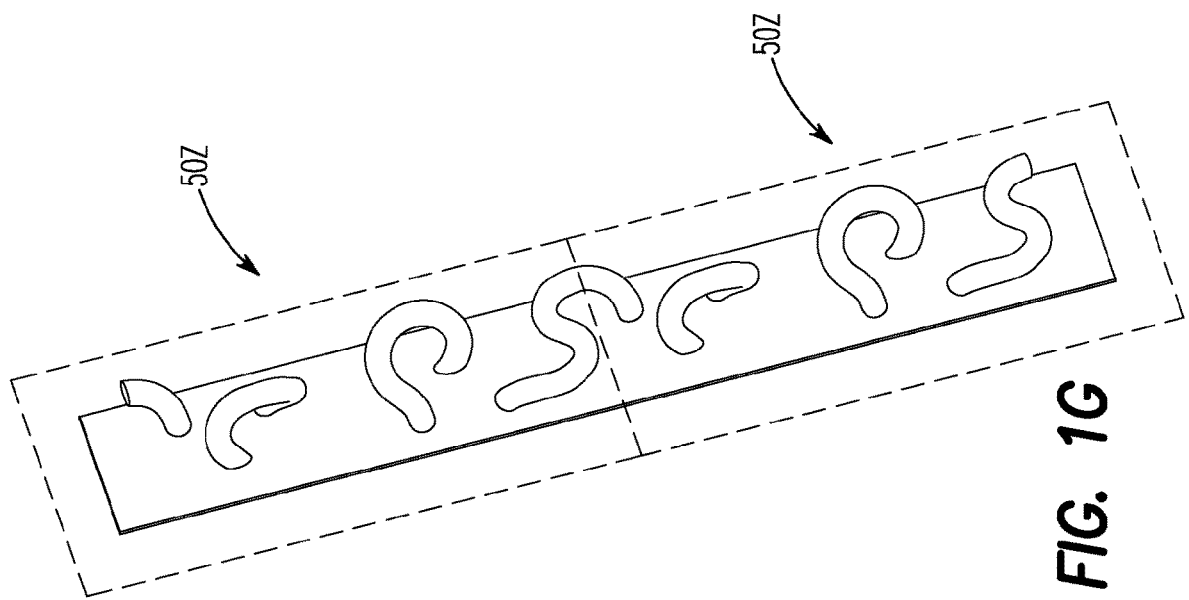
FIG. 1G is a cross-sectional view along the longitudinal access of the tube of FIG. 1E, according to an example of the present disclosure.

As stated above, the system can design, select, make, and/or manufacture an actual reactor having an interwoven reactor tube. The details of the interwoven reactor tube are described in FIGS. 1E-1J. FIGS. 1E-1J illustrate an exemplary continuous flow reactor tube 10Z that can operate at low Re. The continuous flow reactor tube 10Z can include the tubular flow path 12Z that includes turns or curves 14Z and bends 16Z. At least two of the turns or curves 14Z are disposed on a single longitudinal axis LX, but in different, non-parallel planes, for example, plane A and plane B, such that the turns or curves can form an angle of from about 25° to about 60° around the longitudinal axis LX. Depending on the number of paths used to create the continuous flow reactor tube 10Z, the turns can be in two or more different, non-parallel planes, such as from about 6 to about 13 different planes, for example, 8 different planes. Furthermore, at least two of the turns are arranged such that the planes corresponding to the at least two turns can intersect one another, as shown, for example, in FIG. 1F. The turns can also create a pattern that can be repeated or not repeated after a predetermined number of turns. For Example, as shown in FIG. 1G, which illustrates a cross-section of a single path along its longitudinal axis, the single path can include a pattern 50Z that is repeated at least two times (see also FIG. 1E). Each flow path can include from about 4 turns to about 128 turns or more of alternating turns, such as about 16 to about 32 turns, for example, 12.5 alternating turns. Each turn 14Z can include an angle of from about 110° to about 280°, such as about 135° to about 140°. In an example, the first turn can include an angle (such as an angle of about 135°) that is smaller than the angle of the second turn (such as an angle of about 140°). Additionally, as shown in FIGS. 1E, 1F, and 1J, each flow path can also include from about 8 to about 64 or more bends 16Z, such as from about 8 to about 16 bends 16Z. Each bend 16Z can include an angle of from about 15° to less than about 135°, for example, an angle of from about 30° to about 90°, such as an angle of about 45°. In an example, each pattern 50Z can be repeated after about 4 bends or more, such as after about 8 bends.

Additionally or alternatively, when the continuous flow reactor includes an interwoven tubular flow path, the interwoven tubular flow path can include from about 6 to about 100, such as from about 6.5 to about 93.2 turns per 1 $m^3$.

In another example, not shown in the figures, a path of the continuous flow reactor tube 10Z can include two or more different patterns, which may or may not be repeated. When the continuous flow reactor tube 10Z includes a plurality of interwoven flow paths, each path of the continuous flow reactor tube 10Z can include a substantially similar pattern. Alternatively, or additionally, each path of the continuous flow reactor tube 10Z can include a different pattern. Moreover, each path of the continuous flow reactor tube 10Z can include a similar number of repeated patterns (for example two similarly repeated patterns) or can include more or less than two repeated patterns. For example, the second path can include two similarly repeated patterns or can include three similarly repeated patterns.

Figure 1H:
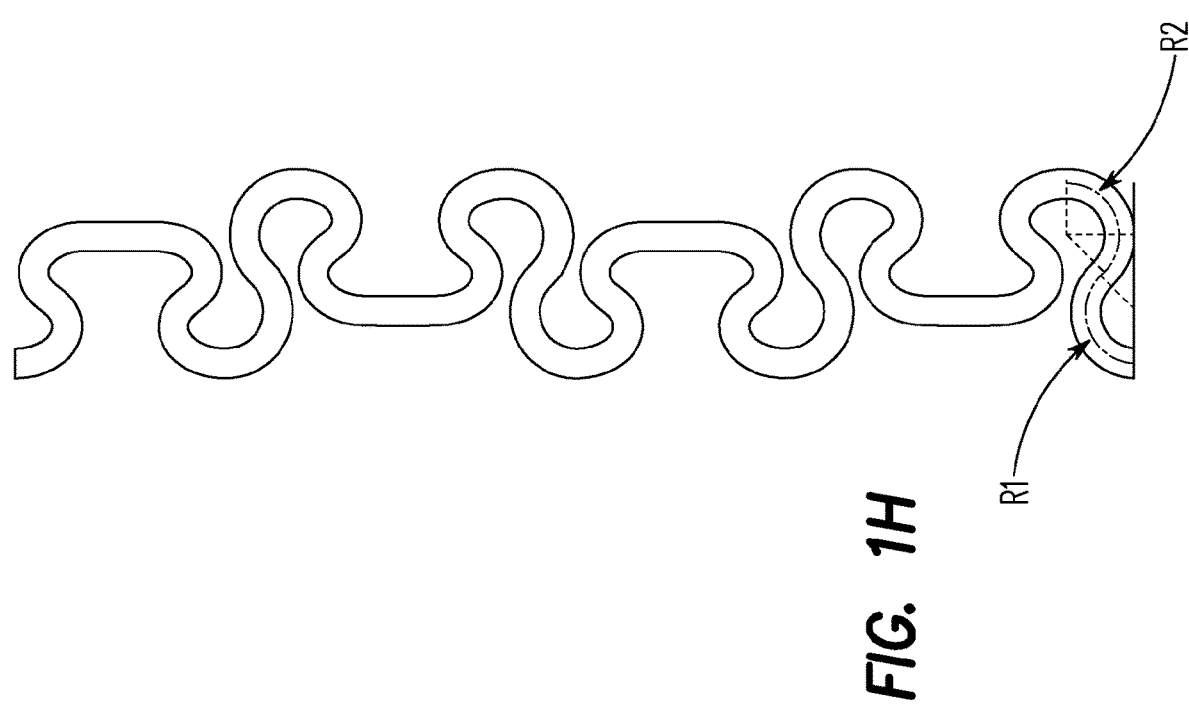
FIG. 1H is a side view of the exemplary continuous flow tube of FIG. 1E, according to an example of the present disclosure.
Figure 1I:
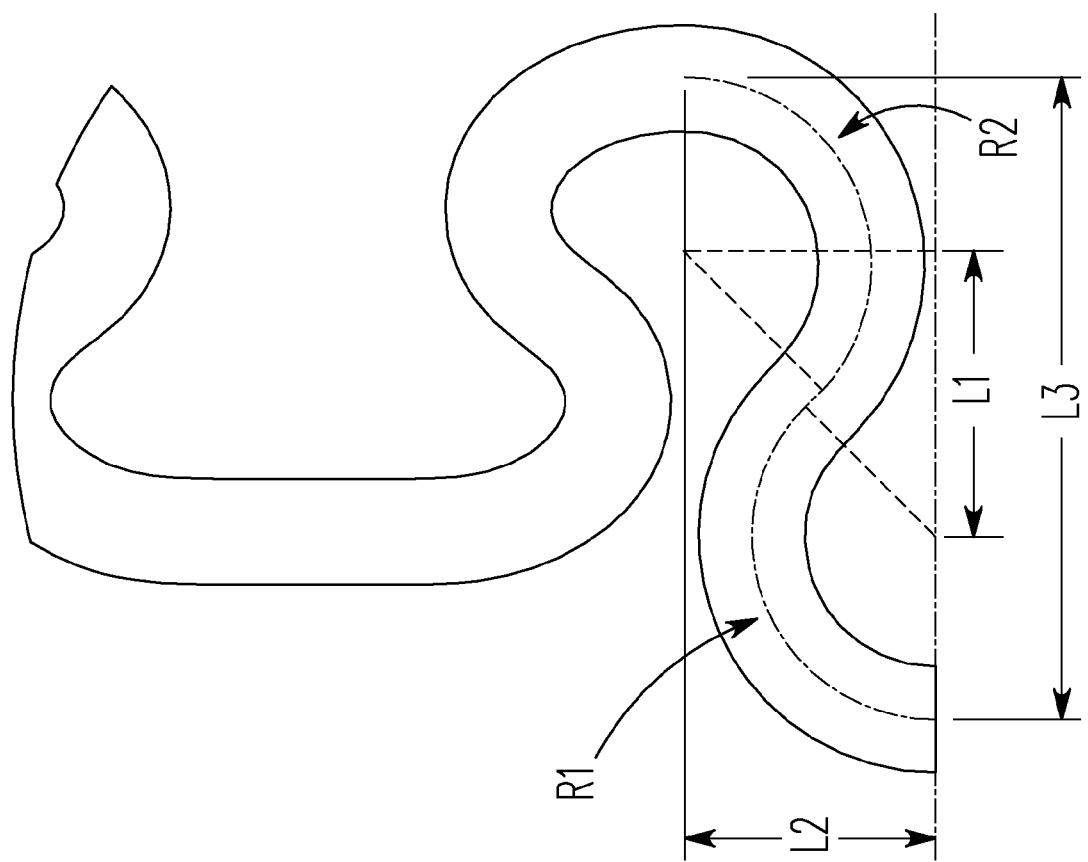
FIG. 1I is a detailed view of area A of the side view of the exemplary continuous flow tube of FIG. 1H, according to an example of the present disclosure.

Referring to FIGS. 1H and 1I, each of the turns 14Z in the continuous flow reactor tube 10Z can include a vertical L1 center to center distance between the turns of from about 1 cm to about 2 cm, such as about 1.5 cm. Additionally, each of the turns 14Z can include a horizontal L2 center to center distance between the turns of from about 1 cm to about 2 cm, such as about 1.63 cm. Furthermore, each of the turns 14Z can include an end to end distance L3 of from about 3 cm to about 4 cm, such as about 3.85 cm. The radius of each turn 14Z in the continuous flow reactor tube 10Z can be substantially constant. For example, referring to FIG. 1I, the radius R1 and R2 can be within 0.05 cm or less of each other, such as about 0.02 cm of each other to prevent substantial differences in the Dean Number between alternating turns. For example, R1 can be about 1.10 cm and R2 can be about 1.12 cm. In an example, the turns 14Z can be arranged to generate a vortex to induce mixing the process stream having a laminar flow with a Reynolds number of from about 187.7 to about 375.5.

In an example, the plurality of turns 14Z can follow a three-dimensional path that may include flow direction change at approximately 45° at a turn center. Additionally, each of the plurality of turns 14Z can include an angle of from about 125° to about 180°.

System Using Serpentine and Interwoven Reactor Tube

Figure 1K:
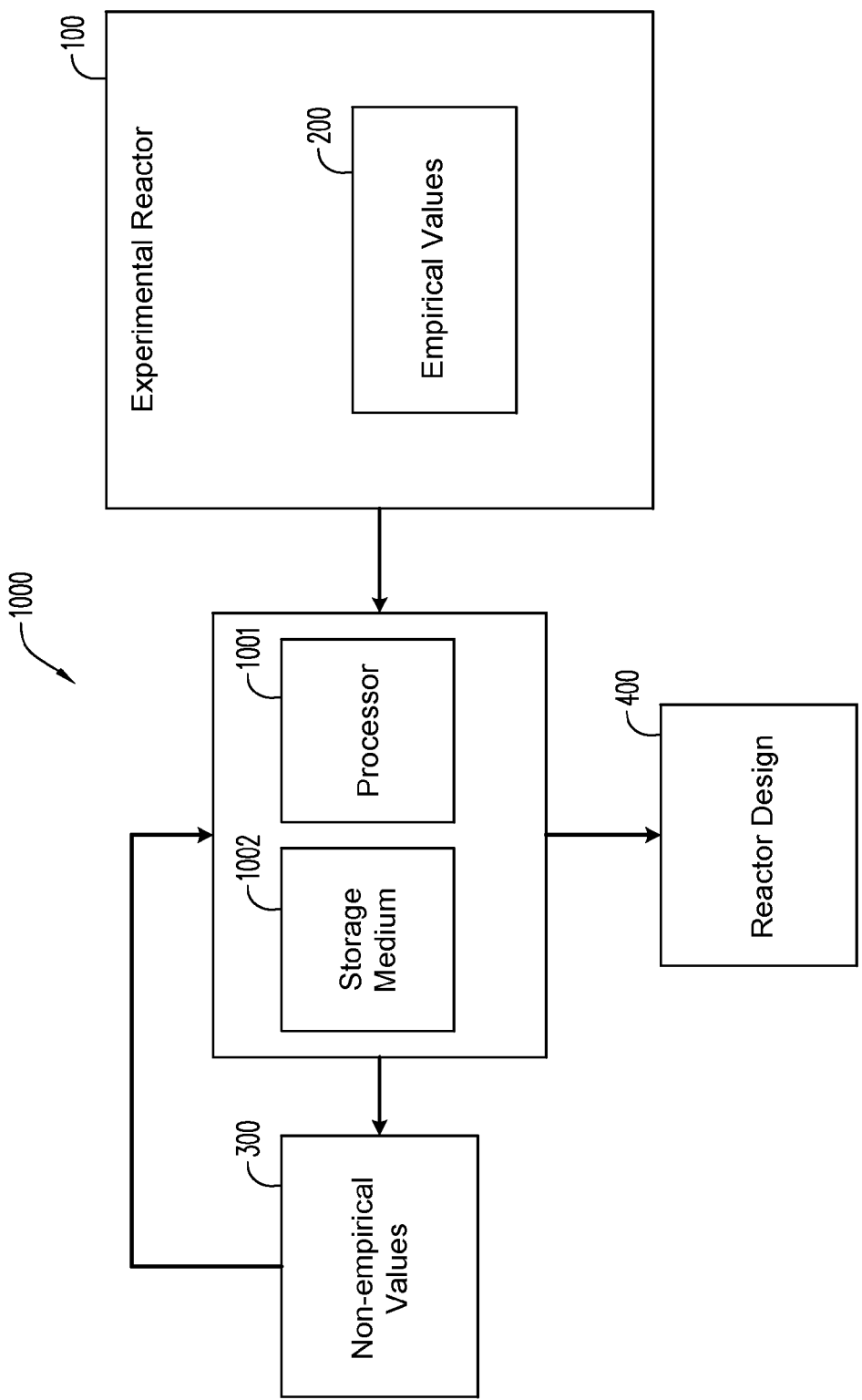
FIG. 1K illustrates an overview of the system, according to an example of the present disclosure.

Referring to FIG. 1K, in order for a system 1000 to design, select, make, and/or manufacture an actual reactor 400 that can manage an actual process stream for commercial purposes with the same results as an experimental reactor 100, the system 1000 can include a processor 1001 and a non-transitory machine-readable storage medium 1002 storing machine-readable instructions that are executable by the processor 1001 to estimate and/or determine the required parameters of an actual reactor 400. In an example, the processor 1001 can receive known and empirical values of reactor parameters of an experimental reactor 100 and/or fluid parameters of a process stream entering the experimental reactor 100. The instructions saved on the non-transitory machine-readable storage medium 1002 storing machine-readable instructions that are executable by the processor 1001 to use the received known and empirical values of the reactor parameters and/or fluid parameters to determine the non-empirical values of the reactor parameters of the experimental reactor 100 and/or fluid parameters of the process stream entering or being introduced to the experimental reactor 100. The instructions saved on the non-transitory machine-readable storage medium 1002 storing machine-readable instructions that are executable by the processor 1001 to forward the empirical values and the non-empirical values and ask the processor 1001 to determine, design, select, make, manufacture, and/or recommend an actual reactor 400 for an actual process stream.

In an example, the experimental reactor 100 can be a hypothetical reactor having certain known parameters. Generally, the experimental reactor 100 can be a fixed reactor that includes a constant internal diameter i.d. and radius of curvature Rc (cm) of a reactor tube. The known empirical values and the non-empirical values are task-dependent. That is, depending on what the user would like to accomplish, the values of at least some of the reactor parameters and/or the fluid parameters may be empirical or non-empirical. In an example, the primary variables associated with the empirical and non-empirical values relating to the reactor parameters and/or the fluid parameters can be the $T_{min}$, the $T_{max}$, the internal diameter i.d., the volumetric flow rate Q (mL/min) of the process stream, the path length L (cm) of the flow path, the radius of curvature Rc (cm) of the reactor tube, the density (ρ) of the fluid in the process stream, and the dynamic viscosity μ (mPa·s) of the fluid in the process stream, and the variance $\sigma^2_{time}$ (min$^2$).

Determining the Empirical Values Using an Experimental Reactor

Figure 2B:
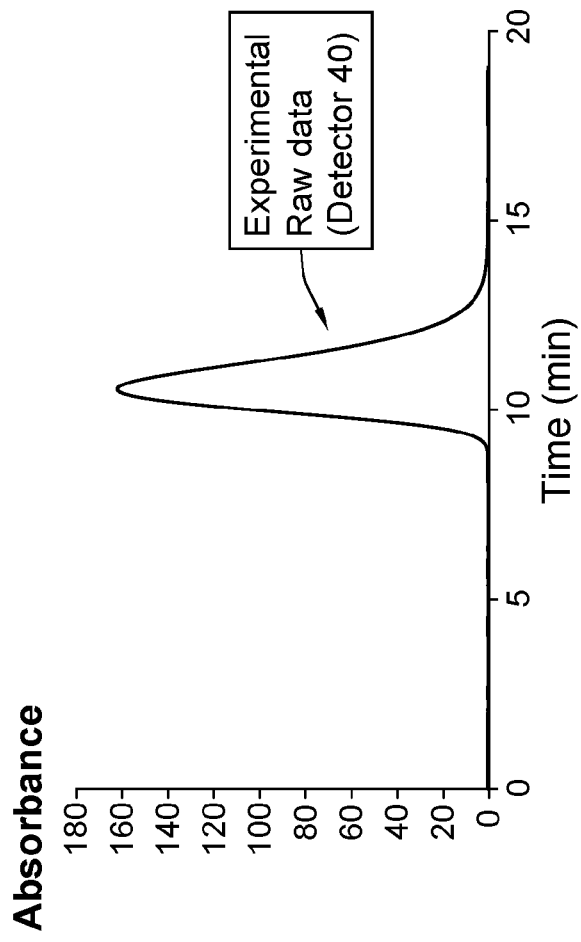
FIG. 2B is a graph showing the experimental raw data detected by a second detector, according to an example of the present disclosure.
Figure 2C:
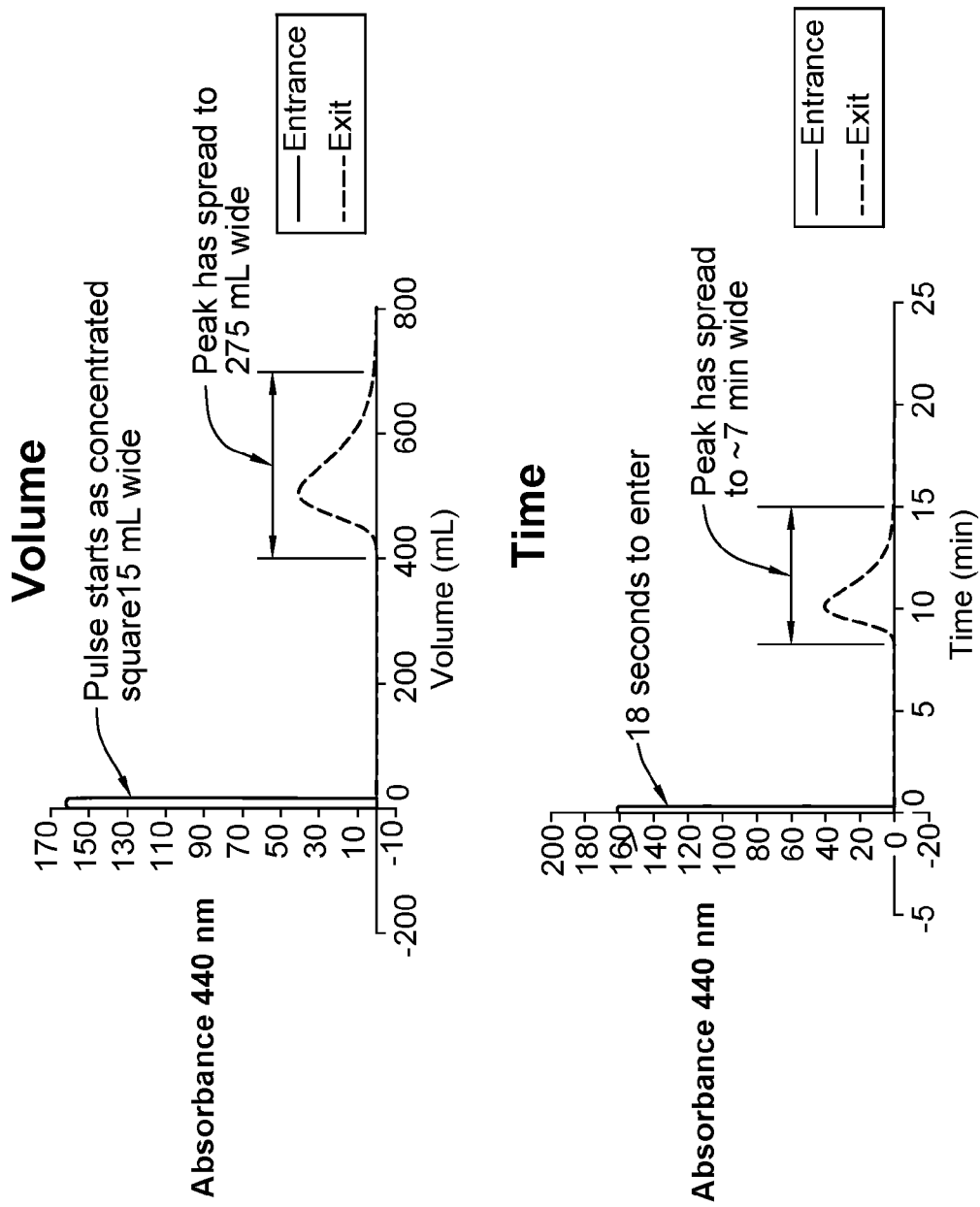
FIG. 2C is a graph showing the entrance and exit of the volume and time of the detectable particles or detectable tracer, according to an example of the present disclosure.

In an example, the empirical values can be values that correspond to experimental reactor parameters and/or fluid-phase parameters that are linear to an experimental set of data. In an example, as shown in FIGS. 2A and 2B, by introducing a process stream at 10, using a pulse injection, into the experimental reactor 100, the first detector 30, which can be in communication with the experimental reactor 100 can determine and/or be provided with the process stream fluid-phase parameters, such as density (ρ), dynamic viscosity (μ), and the Dean Number (De). Moreover, as shown in FIG. 2C, the first detector 30 can detect the volume/amount of detectable particles or detectable tracer that is injected into the process stream and the time it takes to inject the detectable particles or detectable tracer into the process stream and/or the time it takes to introduce the detectable particles or detectable tracer into the experimental reactor 100. Additionally, the first detector 30 can determine or be provided with the type of experimental reactor (e.g., JIB), flow rate Q of the process stream into the experimental reactor 100, the path length L of the experimental reactor 100, and the volume of the experimental reactor 100. In an example, some of the values above may be known to the user and, thus, there is no need for the detector to detect those values. In an example, the detectable particles or detectable tracer can be but not limited to viral/bacteriophage particles, Riboflavin, salts, dyes, protein, and/or sugars. For example, as shown in FIG. 2B, the first detector 30 can determine that the process fluid is water, the experimental reactor type is a JIB, the flow rate of the process stream Q is 50 mL/min, the path length L of the experimental reactor is 1644 cm, the reactor volume is 520 mL, and the Dean Number is 118.94.

Figure 2D:
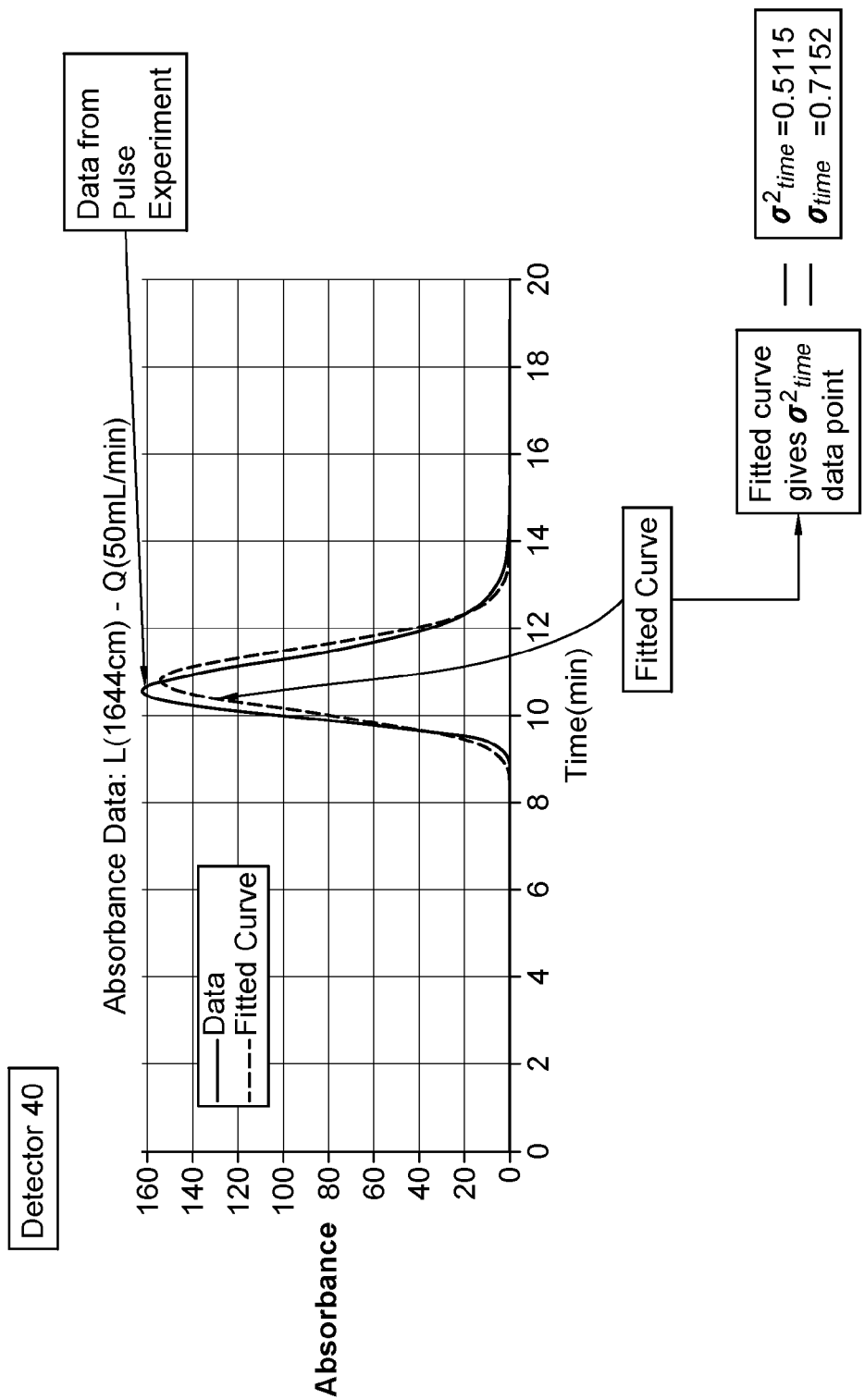
FIG. 2D is a graph showing the fitted curve versus the raw data, according to an example of the present disclosure.

Referring to FIG. 2B, the second detector 40 can also be in communication with the experimental reactor 100 and can detect and measure the time in which the first detectable particle or detectable tracer exits or leaves the experimental reactor 100 and the time in which the last significant amount of the detectable particles or detectable tracer exit or leave the experimental reactor 100. In an example, the second detector 40 can also detect the parameters that can be detected or measured by the first detector 30. Based on the experimental raw data shown in FIG. 2B, the second detector 40 can generate a fitted curve, as shown in FIG. 2D. Based on this fitted curve, the variance $\sigma^2_{time}$ and the standard deviation $\sigma_{time}$ is determined. For example, for a flow rate of 50 mL/min in an experimental reactor 100 having a path length of 1644 cm, based on the fitted curve, the variance $\sigma^2_{time}$ is 0.5115 min$^2$ and the standard deviation $\sigma_{time}$ is 0.7152 min.

Figure 2E:
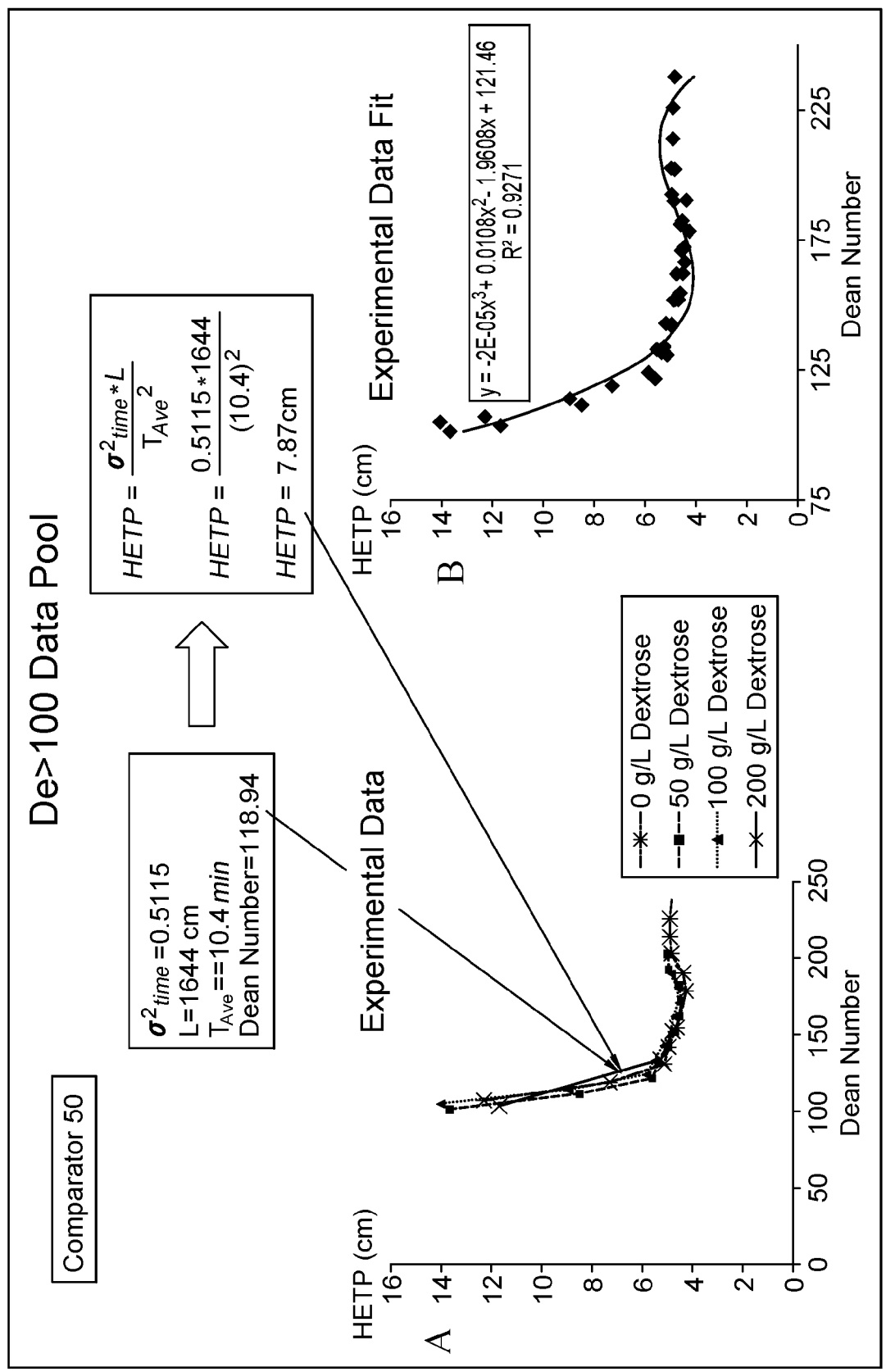
FIG. 2E illustrates the relationship between the Dean Number and HETP in the experimental data and the fitted data, according to an example of the present disclosure.

As shown in FIG. 2E, given the variance $\sigma^2_{time}$ of 0.5115 min$^2$, the experimental reactor path length L of 1644 cm, the Dean Number De of 118.94, and the average residence time $T_{Ave}$ of 10.4 min, the comparator 50 can derive at the height equivalent to a theoretical plate HETP value of 7.87 cm. The comparator 50 can then create a graph corresponding to the experimental data HETP and Dean Number across a broad array of flow rates and process stream viscosities (e.g., 0 g/L of Dextrose, 50 g/L of Dextrose, 100 g/L of Dextrose, and 200 g/L of Dextrose). In an example, based on the experimental data graph, the comparator 50 can also create an experimental data fit graph, as shown in FIG. 2E. As shown in FIG. 2A, at 200, the empirical values/variables can be forwarded to or received by the system 1000 to determine and/or create an actual reactor 400 of interest. In another example, the empirical values may have been previously derived or determined, thus, there may not be a need for the first detector 30 or the comparator 50, as shown in FIG. 3, or for that matter a need for an experimental reactor 100, first detector 30 or the second detector 40 (not shown in the Figures).

The limiting factors for designing, selecting, making, manufacturing, and/or determining the actual reactor 400 can be product stability, required viral incubation, process parameters, and/or no operational or kinetics consideration.

When the limiting factor is the product stability, a target protein that is highly sensitive to viral inactivation chemical is provided. In this example, the system 1000 can be made to determine an acceptable reactor length and flow rate based on the minimum residence time required for viral inactivation kinetics and maximum residence time limitation for product stability. When the limiting factor is the process parameters, the downstream process is limited by the volumetric flow rate Q and the path length L. In this example, the system 1000 can be made to determine process stream minimal residence time required for viral inactivation and maximum residence time for product stability. When there are no operational or kinetics considerations, the target protein may not include stability considerations. In this example, the system can be made to determine the proper Q and L for a resulting $T_{min}$.

Limiting Factor Product Stability—System and Method to Use $T_{min}$ and $T_{max}$ to Determine the Operational Flow Rate and the Path Length of an Actual Reactor In an example, a user, using the system 1000, can develop or create an actual reactor based on a desired pre-determined $T_{min}$ and $T_{max}$. For example, the user requires that the $T_{min}$ be 60 minutes and that the $T_{max}$ be 75 minutes. Additionally, the user can input the desired internal diameter of the reaction tube of the experimental reactor 100 and the radius of curvature of the experimental reactor 100. In this particular example, the experimental reactor 100 and the actual reactor 400 can include identical internal diameter i.d. and radius of curvature Rc. Moreover, referring to FIG. 2A, the density ρ and the dynamic viscosity μ of the fluid in the process stream is either known or is detected by the first detector 30 and can be provided to the system at 200. Accordingly, the system 1000 can provide a design and manufacturing specification of an actual reactor 400 based on the above-inputted parameters. The new design and manufacturing specification of an actual reactor 400 (i.e., the path length of the reaction tube of the actual reactor 400) can vary based on the operational volumetric flow rate Q. This is especially true for a system that is operated under $\sigma^2_{time} < \sigma^2_{max}$ conditions (i.e., reactor path length L and flow rate Q have multiple combinations that satisfy the $T_{min}$ and $T_{max}$ requirement). However, when the system is operated under $\sigma^2_{time} = \sigma^2_{max}$ conditions, only one reactor path length L and flow rate Q combination satisfies $T_{min}$ and $T_{max}$ requirement.

Figure 4:
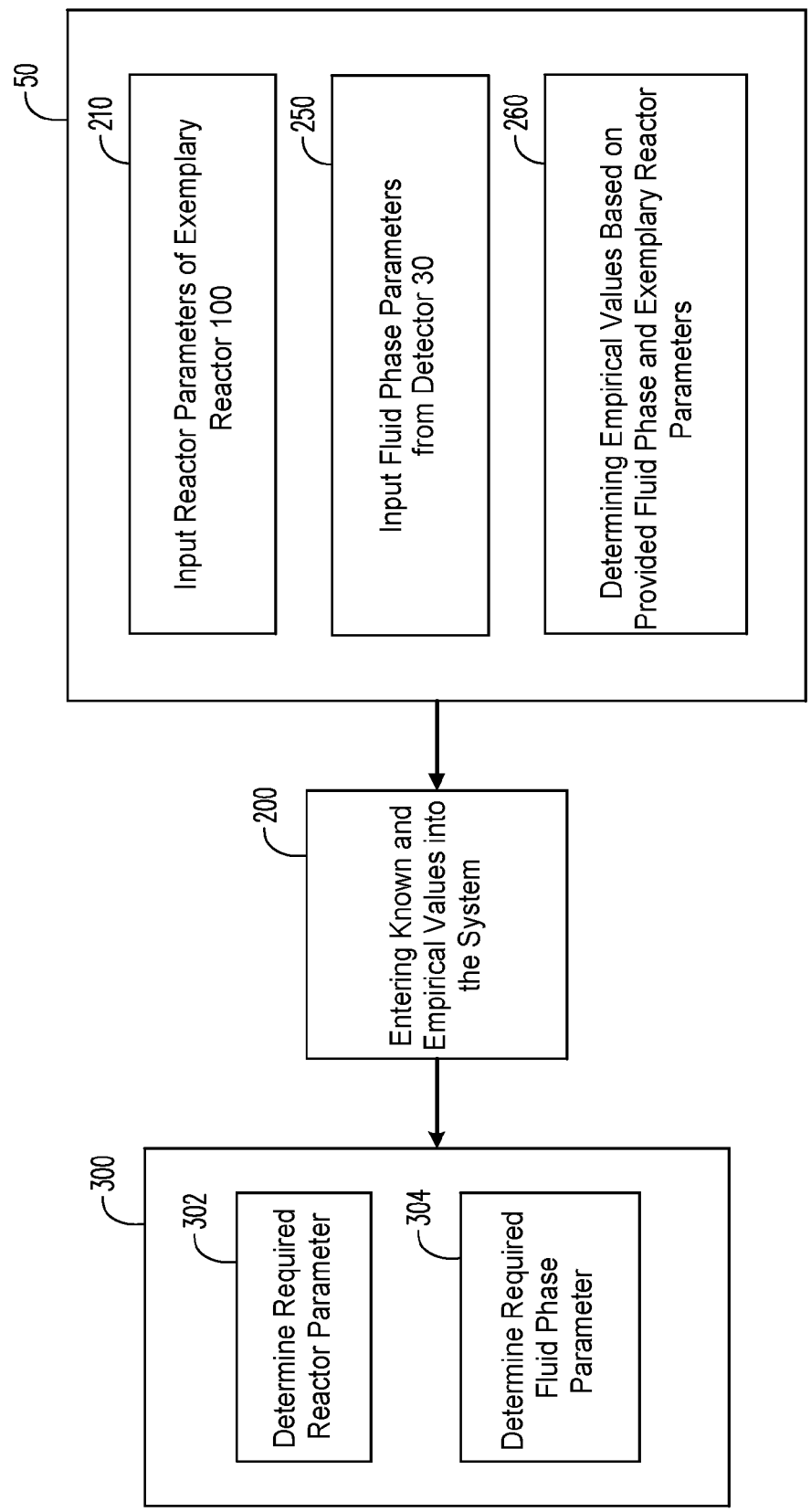
FIG. 4 illustrates the overview of the relationship between the comparator and the non-empirical variables, according to an example of the present disclosure.
Figure 5A:
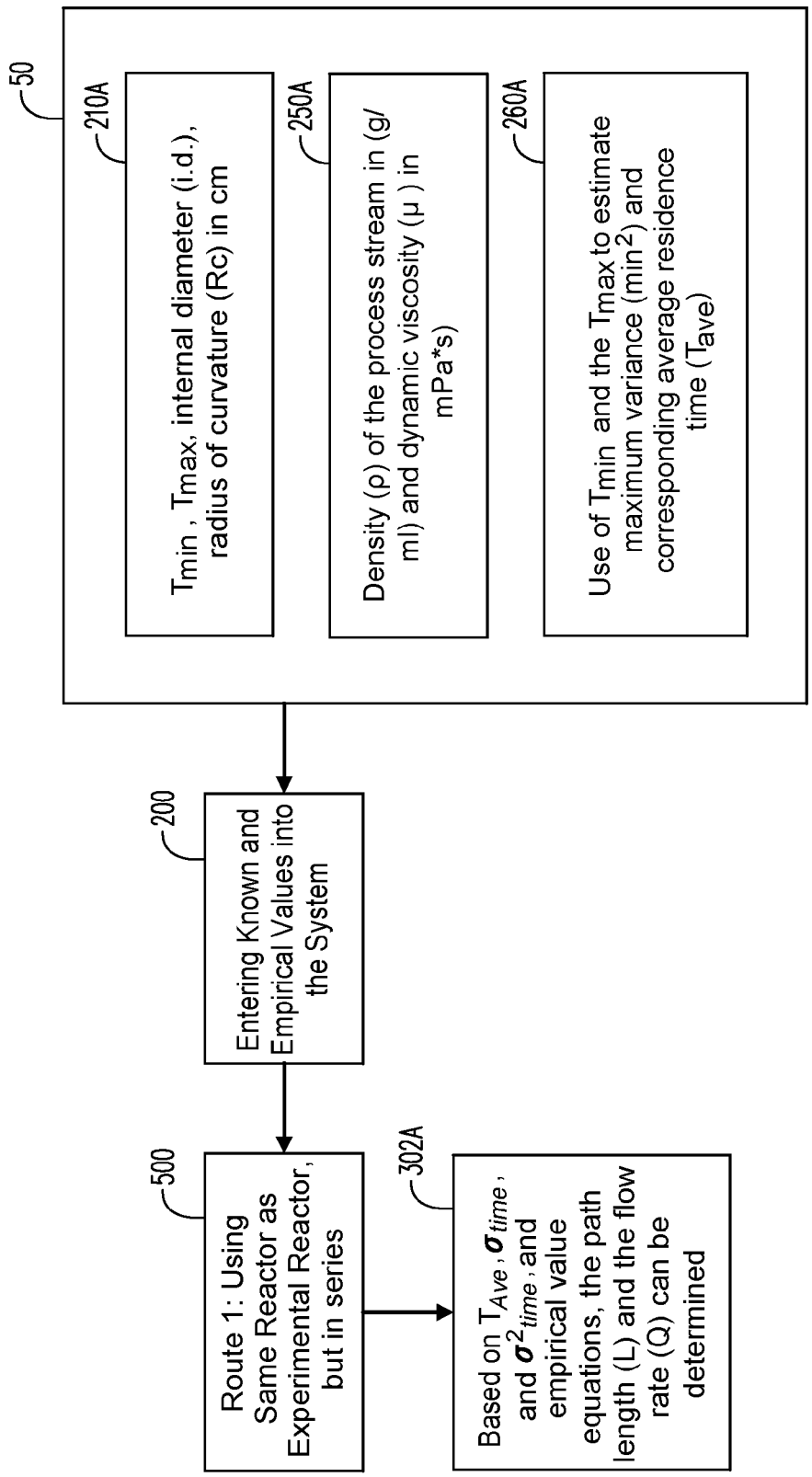
FIG. 5A illustrates the overview of how the system derives at reactor tube path length and flow rate, according to an example of the present disclosure.
Figure 5B:
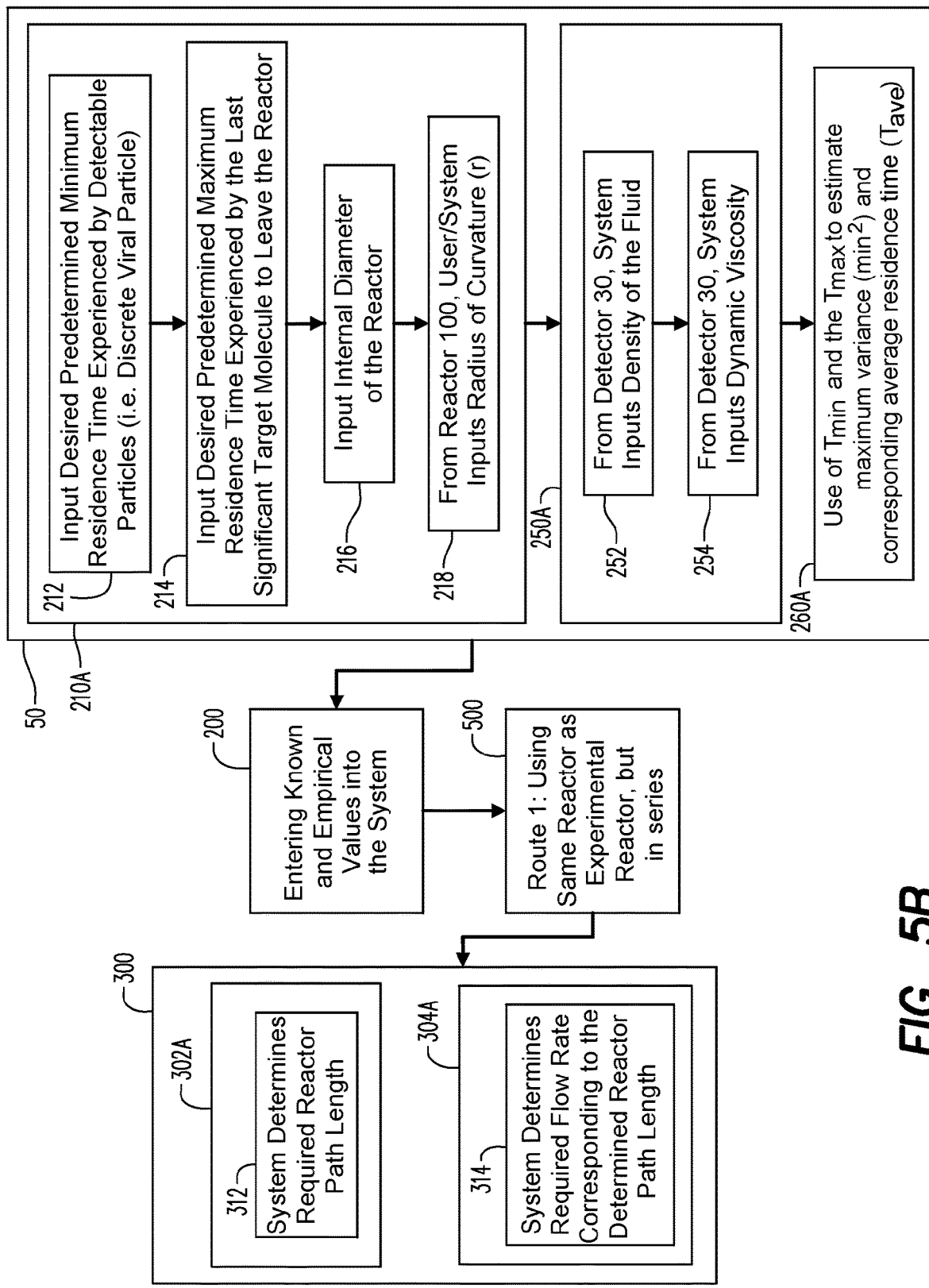
FIG. 5B illustrates the details of how the system derives at reactor tube path length and flow rate, according to an example of the present disclosure.

Referring to FIGS. 4, 5A, and 5B, at 50, the system 1000 can determine or the user can input the known values 210/210A, 250/250A, and empirical values and/or variables 260/260A. These empirical values and/or variables 260/260A can be divided into reactor parameters of the experimental reactor 100 and/or the fluid-phase parameters. For example, as shown in FIGS. 5A and 5B, at 212, the desired predetermine $T_{min}$ of the experimental reactor 100 can be entered into the comparator 50. At 214, the desired predetermine $T_{max}$ of the experimental reactor 100 can be entered into the comparator 50. Furthermore, at 216, the internal diameter i.d. of the experimental reactor 100 can be entered into the comparator 50. At 218, the radius of curvature Rc of the experimental reactor 100 can be entered into the comparator 50. Thus, in this particular example, the inputted known values corresponding to the reactor parameters can be $T_{min}$, $T_{max}$, internal diameter i.d., and the radius of curvature Rc, shown as 210A in FIG. 5B.

Additionally, referring to FIG. 5B, at 252, the density (ρ) of the fluid in the process stream from the first detector 30 can be entered into the comparator 50. At 254, the dynamic viscosity (μ) can be entered into the comparator 50. Thus, in this particular example, the inputted known values corresponding to the fluid-phase parameters can be density ρ and the dynamic viscosity μ, shown as 250/250A.

The empirical values can then be determined using pulse injection of the process stream into the experimental reactor 100, as described above. For example, referring to FIGS. 5A and 5B, at 260A, the comparator 50 can use the desired pre-determined value for $T_{min}$ (e.g., 60 min) and the $T_{max}$ (e.g., 75 min) to predict and/or determine the empirical values. In this particular example, given the $T_{min}$ and the $T_{max}$, the comparator 50 can determine the maximum variance $\sigma^2_{time}$ (i.e. $\sigma^2_{max}$) and the corresponding average residence time $T_{Ave}$, as shown below:

$$T_{Ave} = T_{min} + (n*\sigma_{max}), \text{ wherein } n \text{ can be 5;} \quad (1)$$

$$T_{Ave} = T_{max} - (m*\sigma_{max}), \text{ wherein } m \text{ can be 3} \quad (2)$$

$$\Delta T = 8\sigma_{max} \quad (3)$$

$$15 = 8\sigma_{max} \quad (4)$$

$\sigma_{time} = 1.875$ min, $\sigma^2_{time} = 3.52$ min$^2$, $T_{Ave} = 69.375$ min Given the determined variance $\sigma^2_{time}$, $T_{Ave}$, and standard deviation $\sigma_{time}$, the comparator 50, utilizing the data from the first and second detectors 30 and 40, respectively, can derive at the empirical values to determine the theoretical plate (HETP) in cm$^2$ and/or Dean Number De, as discussed above. For example, HETP can be defined as follows:

$$\text{HETP} = (aDe^3 + bDe^2 + cDe + d), \quad (5)$$

where De is the Dean Number, a, b, c, and d are based on empirical data fits only valid for Dean Number ≥ 100.

$$HETP = \frac{\sigma^2_{time} * L}{T^2_{Ave}}$$

By applying a panel of Dean Number (De) ≥ 100, each De fixes a flow rate Q and returns an HETP, as shown below.

$$\frac{HETP * T^2_{Ave}}{L_{T_{Ave}}} = \sigma^2_{time} \quad (6)$$

$$\frac{(aDe^3 + bDe^2 + cDe + d) * 69.375^2}{L_{T_{Ave}}} = \sigma^2_{time} = \sigma^2_{max} \quad (7)$$

$$De \equiv \frac{\rho}{\mu} 2rv \sqrt{\frac{r}{R_c}} = \frac{\frac{\rho}{\mu} 2Q}{r\pi} \sqrt{\frac{r}{R_c}} \quad (8)$$

In an example, as shown in FIG. 4, the non-empirical values associated with the reactor parameters can be derived at 302 or the non-empirical values associated with the fluid-phase parameter can be derived at 304. For example, referring to FIGS. 5A and 5B, the empirical value equations above and the determined $\sigma^2_{time}$, $\sigma_{time}$, and $T_{ave}$, can be forwarded to the system at 200 so that the system, at 302A, can simultaneously solve the empirical value related equations as shown below, to determine the path length (L) and the flow rate (Q) for an actual reactor 400.

$$\frac{(aDe^3 + bDe^2 + cDe + d) * T^2_{Ave}}{L_{T_{Ave}}} \leq \sigma^2_{max} \quad (9)$$

$$T_{Ave} = T_{min} + (n*\sigma_{time}), \text{ wherein } n \text{ can be 5} \quad (10)$$

$$T_{Ave} = T_{max} - (m*\sigma_{time}), \text{ wherein } m \text{ can be 3} \quad (11)$$

For a constant $T_{Ave}$, fixing a Q value fixes a corresponding $L_{T_{Ave}}$ value. Each Q value and $L_{T_{Ave}}$ value combination returns a resulting $\sigma^2_{time}$ value as shown below.

$$\frac{(aDe^3 + bDe^2 + cDe + d) * T_{Ave}^2}{L_{T_{Ave}}} = \sigma_{time}^2 \qquad (12)$$

Figure 5C:
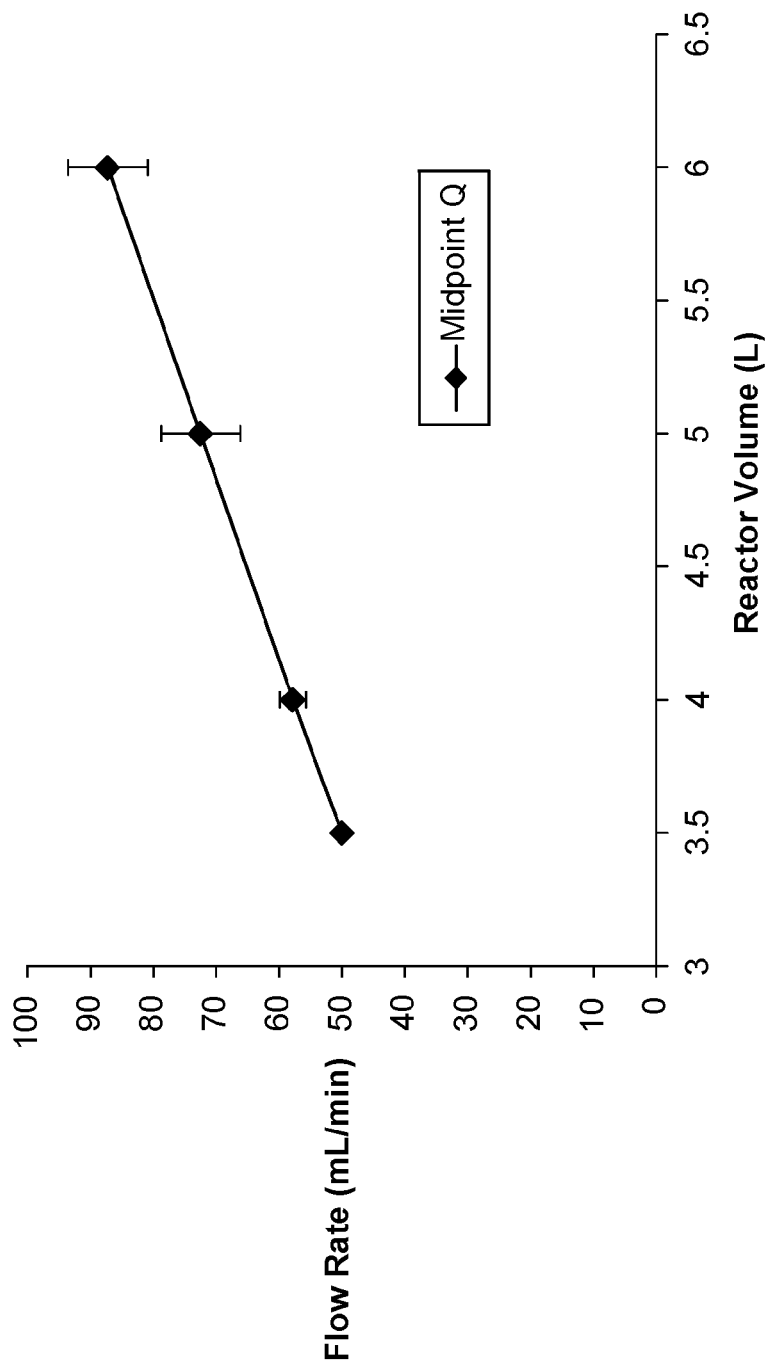
FIG. 5C is a graph illustrating the relationship between the reactor volume and the flow rate of the actual reactor, according to an example of the present disclosure.

Solving $\sigma^2_{time}$ results in a minimum reactor volume that is constrained by $T_{Ave}=T_{min}+(5*\sigma_{max})$ and $T_{Ave}=T_{max}-(3*\sigma_{max})$. FIG. 5C illustrates a graphical representation of different flow rates and their respective corresponding reactor tube length path L to have the desired predetermined $T_{min}$ and $T_{max}$. Additionally or alternatively, as shown in steps 312 and 314 of FIG. 5B, the output can include the reactor tube path length L and the flow rate Q, respectively.

Given that in this example, the experimental reactor and the actual reactor are the same, based on the selected flow rate Q and the corresponding reactor tube path length, a series of reactors can be connected to one another to achieve the corresponding reactor tube path length.

Figure 6A:
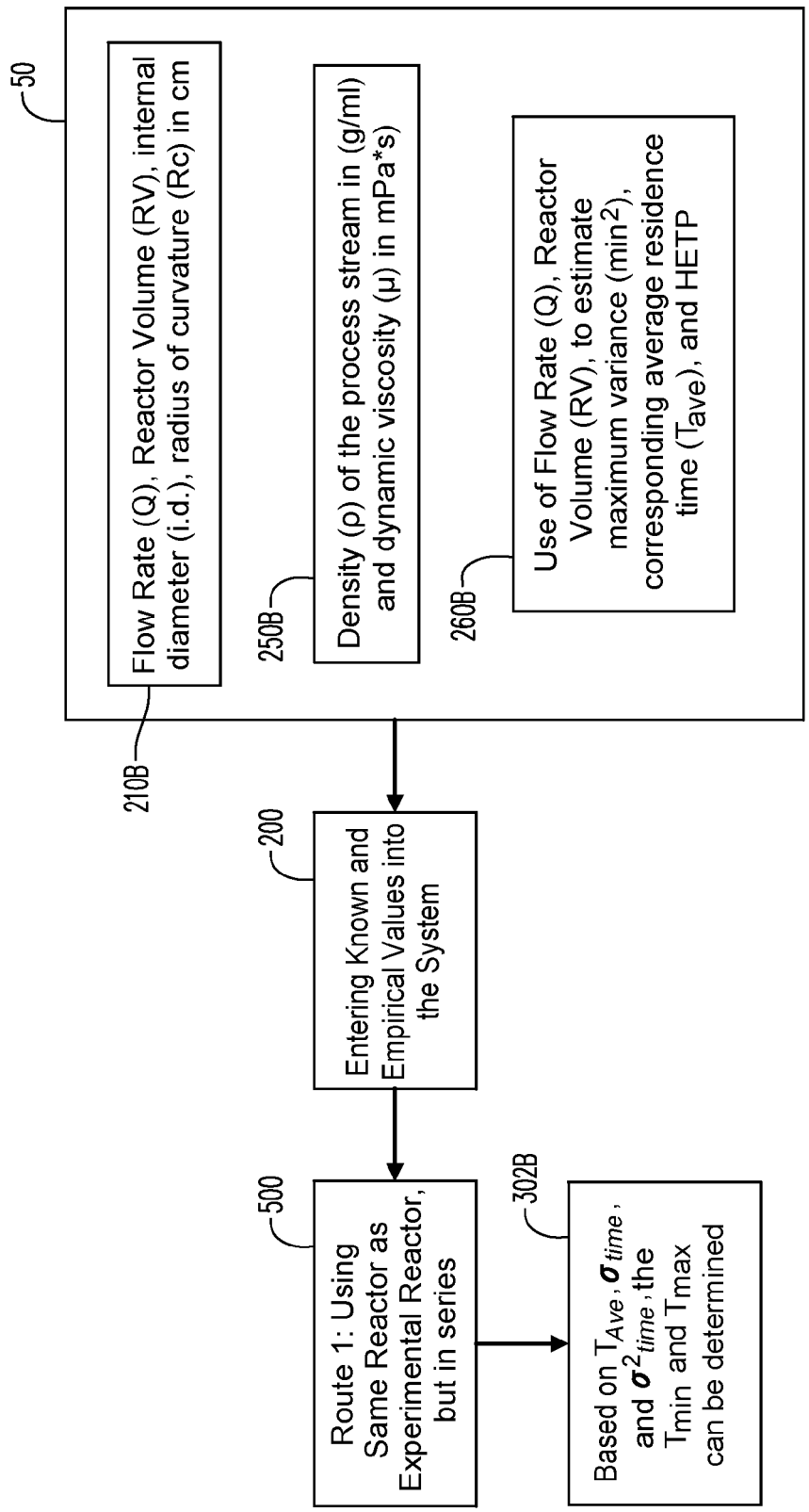
FIG. 6A illustrates the overview of how the system derives at $T_{min}$ and $T_{max}$, according to an example of the present disclosure.

Limiting Factor is Process Parameters—System and Method to Use Reactor Volume RV and Flow Rate Q to Dictate the $T_{min}$ and $T_{max}$ In an example, a user, using the system 1000, can determine the $T_{min}$ and the $T_{max}$ of a reactor having known reactor parameters and fluid-phase parameters. For example, as shown in FIG. 6A, at 210B, the known reactor parameters can include reactor volume RV (e.g. 3120 mL), flow rate Q (e.g., 50 mL), internal diameter i.d., and the radius of curvature Rc. Additionally, as also shown in FIG. 6A, at 250B, the known fluid-phase parameters can include density (ρ) and the dynamic viscosity (μ) of the fluid in the process stream. In this example, reactor volume RV, flow rate Q, internal diameter i.d., and the radius of curvature Rc can be entered into the comparator 50. The comparator 50 can then determine the empirical values such as variance $\sigma^2_{time}$, average residence time $T_{Ave}$, and the HETP.

Figure 6B:
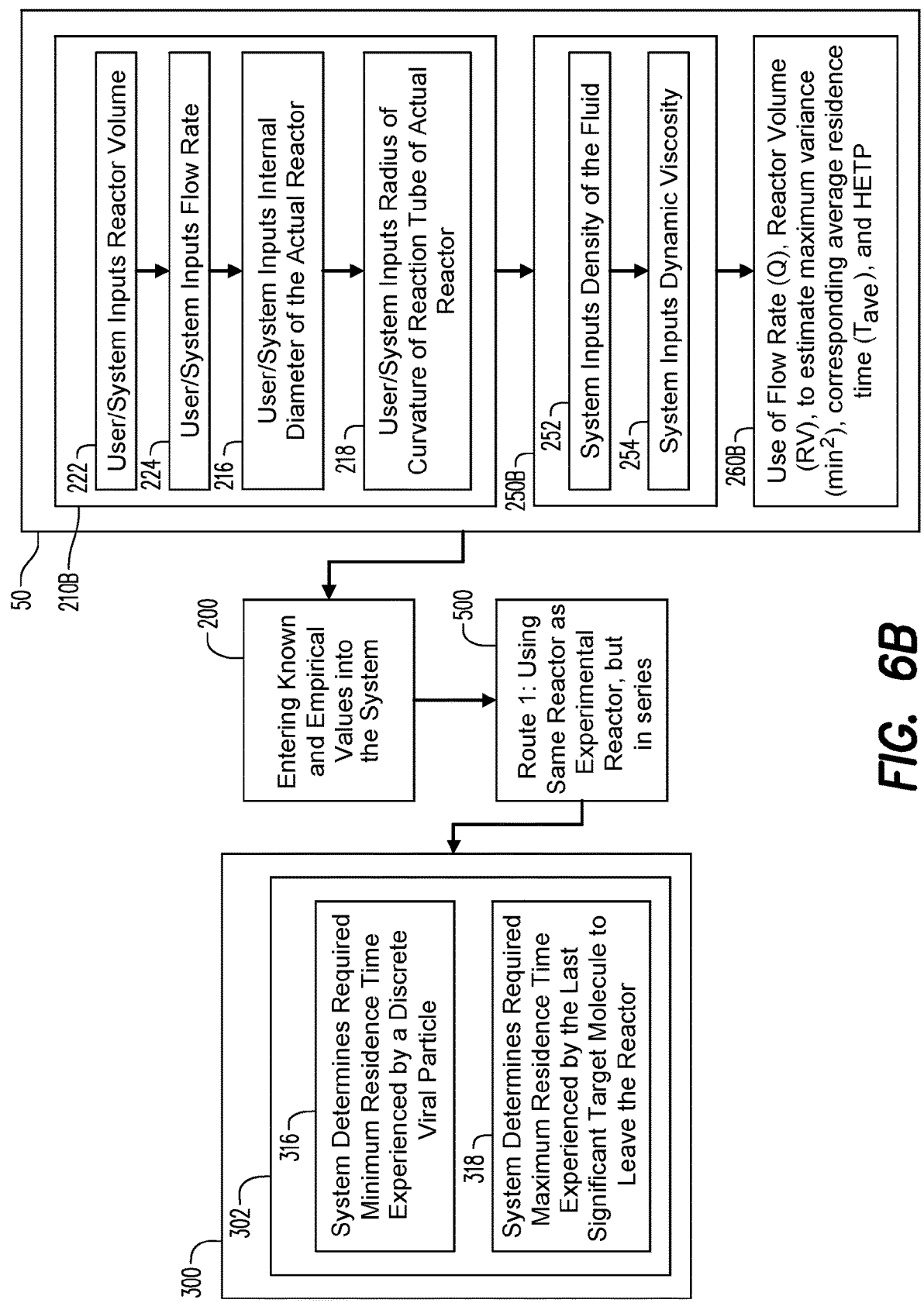
FIG. 6B illustrates the details of how the system derives at $T_{min}$ and $T_{max}$, according to an example of the present disclosure.

Referring to FIG. 6B, in this example, the reactor volume RV of the reactor can be entered into the system at 222, the flow rate Q of the process stream can be entered into the system at 224, the internal diameter i.d. of the reaction tube of the reactor can be entered into the system at 216, and the radius of curvature Rc of the reaction tube of the reactor can be entered into the system at 218. Thus, in this particular example, the inputted values corresponding to the reactor parameters at 210B can be the reactor volume RV, process stream flow rate Q, internal diameter i.d. of the reaction tube of the actual reactor, and the radius of curvature of the reaction tube of the actual reactor Rc.

Additionally, at 252, the density (ρ) of the fluid in the process stream can be entered into the system 1000. At 254, the dynamic viscosity (μ) can be entered into the system 1000. Thus, in this particular example, the inputted known values corresponding to the fluid-phase parameters at 250B can be density ρ and the dynamic viscosity μ.

Based on the known process stream flow rate Q (e.g., 50 mL/min), the known reactor volume RV (e.g., 3120 mL), the known internal diameter of a reaction tube i.d., and the known radius of curvature Rc, the processor 1001 of the system 1000 can predict and determine $T_{min}$ and $T_{max}$.

To predict and/or determine the $T_{min}$ and $T_{max}$, the known values can be entered into the comparator 50. The comparator 50, at 260B, using the experimental reactor as described above, can utilize the process stream flow rate Q and the reactor volume RV to predict and/or determine the average residence time ($T_{Ave}$) as shown in the equations below.

$$T_{Ave} = \frac{RV}{Q} \qquad (13)$$

$$T_{Ave} = \frac{3120 \text{ mL}}{50\frac{\text{mL}}{\text{min}}} \qquad (14)$$

$$T_{Ave} = 62.4 \text{ min} \qquad (15)$$

Once the comparator 50 derives the $T_{Ave}$ value, the comparator 50 can then utilize the $T_{Ave}$, Q, De, Rv, and L to predict and/or determine the variance $\sigma^2_{time}$ using the experimental reactor 100 and the equations below.

HETP=$(aDe^3+bDe^2+cDe+d)$, where De is the Dean Number, a, b, c, and d are based on empirical data fits only valid for Dean Number≥100.

For a Q of 50 mL/min and a De of 118.94, the HETP can equal to 7.464 cm. Based on this derived HETP value, the variance $\sigma^2_{time}$ can be predicted or determined by the comparator 50 using the equations below.

$$HETP = \frac{\sigma^2_{time} * L}{T^2_{Ave}} \qquad (16)$$

$$\frac{HETP * T^2_{Ave}}{L} = \sigma^2_{time} \qquad (17)$$

$$\frac{7.464 * 62.4^2}{9864} = \sigma^2_{time} \qquad (18)$$

$$\sigma^2_{time} = 2.95 \text{ min}^2 \qquad (19)$$

The above empirical values and known values can then be forwarded to the system at 200. The processor 1001 having derived at variance $\sigma^2_{time}$, can utilize this variance $\sigma^2_{time}$, the standard deviation $\sigma_{time}$, reactor tube length L, radius of curvature Rc, Dean Number De, flow rate Q, and $T_{Ave}$, to estimate and/or determine the $T_{min}$ and $T_{max}$ for the actual reactor as shown in the equations below.

$$T_{Ave}=T_{min}+(n*\sigma_{max}), \text{ wherein } n \text{ can be } 5 \qquad (20)$$

$$T_{Ave}=T_{max}-(m*\sigma_{max}), \text{ wherein } m \text{ can be } 3 \qquad (21)$$

$$T_{min}=53.81 \text{ min} \qquad (22)$$

$$_{max}=67.55 \text{ min} \qquad (23)$$

Figure 6C:
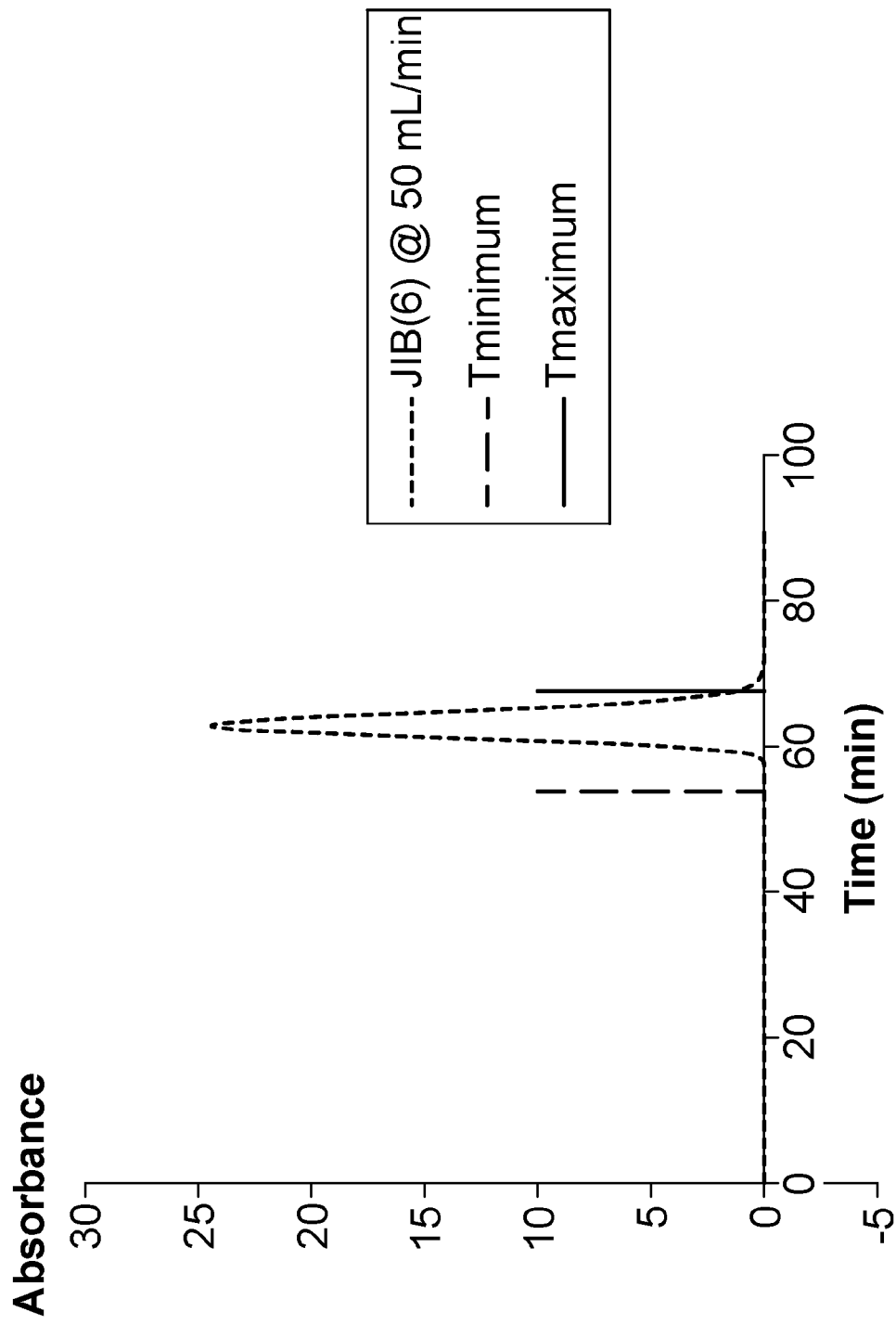
FIG. 6C is a graph illustrating the $T_{min}$ and $T_{max}$ of an actual reactor, according to an example of the present disclosure.

In an example, as shown in FIG. 6B, at 316, a display can show the $T_{min}$ value and at 318, the display can show the $T_{max}$ value. In addition or alternatively, the display can show a graphical representation of the $T_{min}$ and $T_{max}$, as shown in FIG. 6C.

Figure 7A:
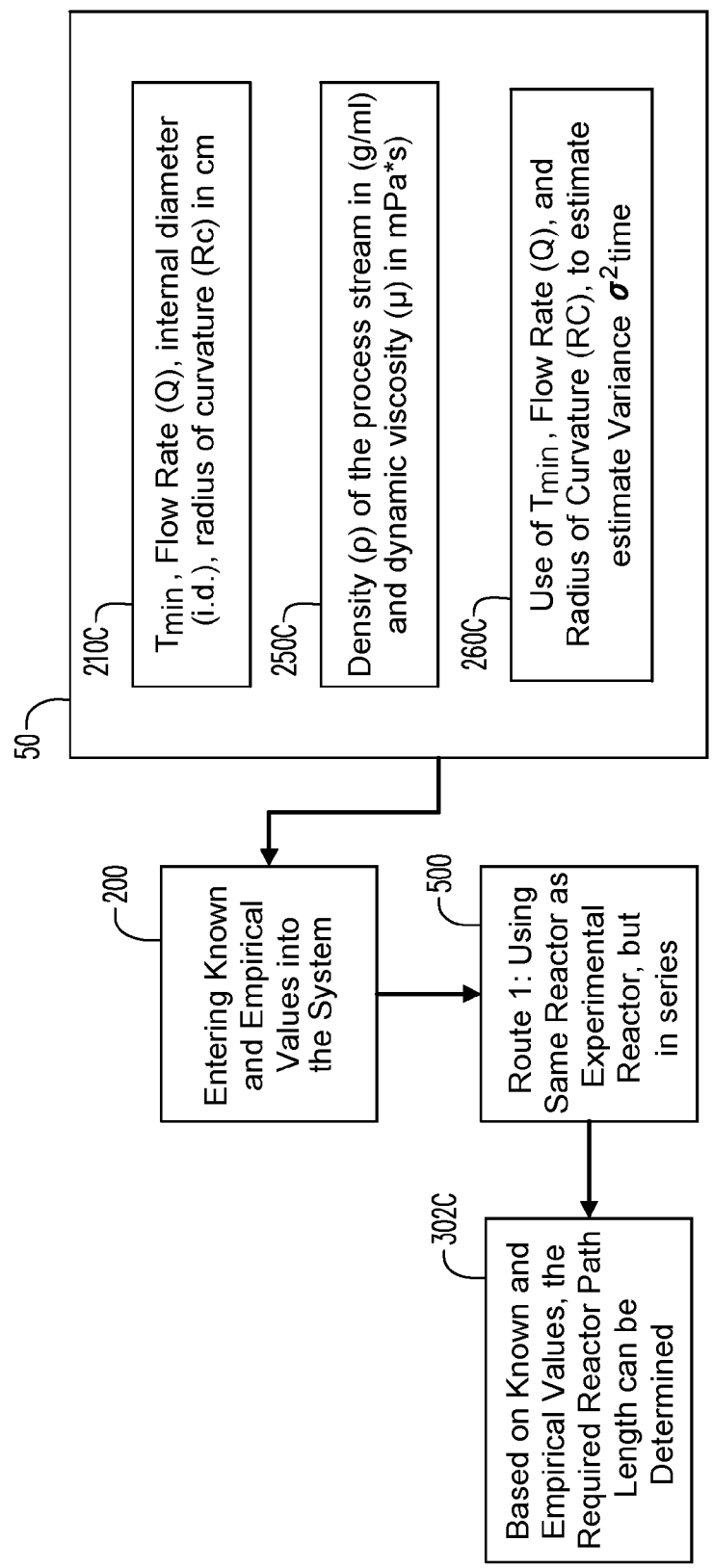
FIG. 7A illustrates the overview of how the system derives at an actual reactor path length, according to an example of the present disclosure.

No Operational or Kinetics Considerations—System and Method to Use Tmin and Operational Flow Rate (Q) to Determine Path Length of an Actual Reactor In an example, a user, using the system 1000, can develop or create an actual reactor based on a desired pre-determined $T_{min}$ (60 min), process stream flow rate Q (50 mL/min), internal diameter i.d. of the reaction tube (0.635 cm), the radius of curvature Rc, density ρ, and the dynamic viscosity μ. For example, as shown in FIG. 7A, at 210C, the known reactor parameters can include $T_{min}$, process stream flow rate Q, internal diameter i.d. of the reaction tube, the radius of curvature Rc. Additionally, as also shown in FIG. 7A, at 250C, the known fluid-phase parameters can include density ρ and the dynamic viscosity μ of the fluid in the process stream. In this example, these known values can be entered into the comparator 50, so that it can determine the empirical values, such as variance $\sigma^2_{time}$ and the average residence time $T_{Ave}$.

Figure 7B:
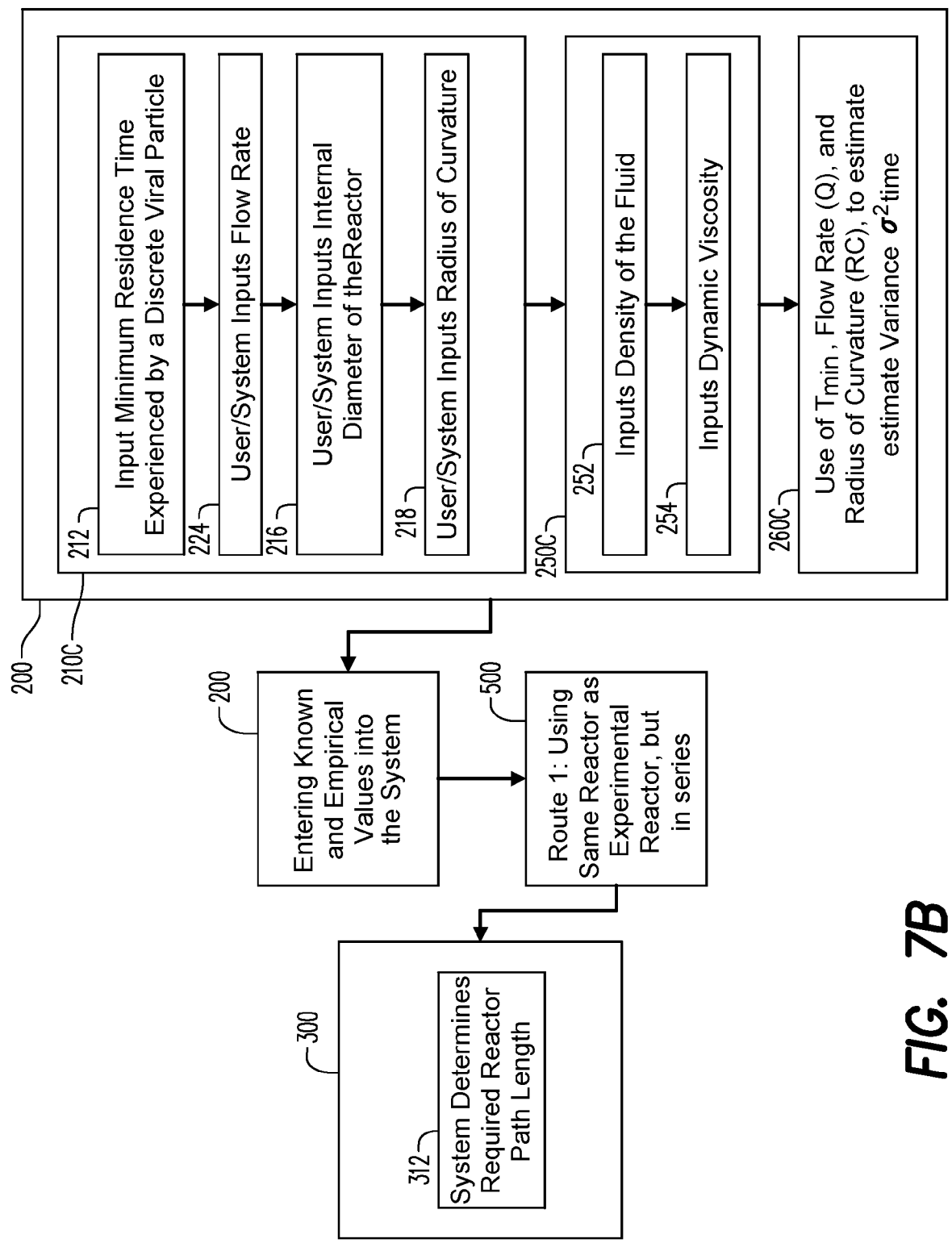
FIG. 7B illustrates the details of how the system derives at an actual reactor path length, according to an example of the present disclosure.

Referring to FIG. 7B, in this example, the $T_{min}$ can be entered into the system at 212, the flow rate Q of the process stream can be entered into the system at 224, the internal diameter i.d. of the reaction tube of the reactor can be entered into the system at 216, and the radius of curvature Rc of the reaction tube of the reactor can be entered into the system at 218. Thus, in this particular example, the inputted values corresponding to the reactor parameters at 210C can be the $T_{min}$, process stream flow rate Q, internal diameter i.d. of the reaction tube of the actual reactor, and the radius of curvature of the reaction tube of the actual reactor Rc.

Additionally, at 252, the density (ρ) of the fluid in the process stream can be entered into the system 1000. At 254, the dynamic viscosity (μ) can be entered into the system 1000. Thus, in this particular example, the inputted known values corresponding to the fluid-phase parameters at 250C can be density (ρ) and the dynamic viscosity (μ).

Based on the known $T_{min}$, process stream flow rate Q (e.g., 50 mL/min), the known internal diameter of a reaction tube i.d., and the known radius of curvature Rc, the processor 1001 of the system 1000 can predict and determine the reaction tube flow path length L of an actual reactor 400.

To predict and/or determine the reaction tube flow path length L of an actual reactor 400, the known values can be entered into the comparator 50. The comparator 50, at 260C, using the experimental reactor as described above, can utilize the $T_{min}$, the process stream flow rate Q and the Dean Number De, to predict and/or determine the $T_{Ave}$ and variance $\sigma^2_{time}$, as shown in the equations below.

$$HETP = \frac{\sigma^2_{time} * L_{T_{Ave}}}{T^2_{Ave}} \quad (24)$$

$$\sqrt{HETP} = f(De) = \frac{\sigma_{time} * \sqrt{L_{T_{Ave}}}}{T_{Ave}} = (aDe^3 + bDe^2 + cDe + d) \quad (25)$$

Wherein a, b, c, and d are based on empirical data fits only valid for Dean numbers≥100

$$T_{Ave} = T\min + (n * \sigma_{time}), \quad (26)$$

wherein n can be 5

$$(27) \quad T_{Ave} = \frac{RV}{Q} = \frac{CA * L_{T_{Ave}}}{Q}$$

By re-arranging the equation $$\sigma_{time} = \frac{1}{5} * \left( \frac{CA * L_{T_{Ave}}}{Q} - T\min \right) \quad (28)$$

$$\sigma_{time} = \frac{f(De) * \frac{CA * L_{T_{Ave}}}{Q}}{\sqrt{L_{T_{Ave}}}} \quad (29)$$

Referring to FIGS. 7A and 7B, the empirical value equations above and the known values can be forwarded to the system at 200 so that the system, at 302C, can determine the path length (L) given the $T_{min}$ of 60 min, flow rate Q of 50 mL/min, and an i.d. of 0.635 m by the equation below.

$$L_{T_{Ave}} = \frac{25 * CA^2 * f(De)^2 \pm 5 * \sqrt{\frac{25 * CA^4 * f(De)^4 + 4 * CA^3 * f(De)^2 * \frac{Q * T_{min}}{} + \frac{2 * CA *}{Q * T_{min}}}{Q * T_{min}}}}{2CA^2} \quad (30)$$

Figure 7C:
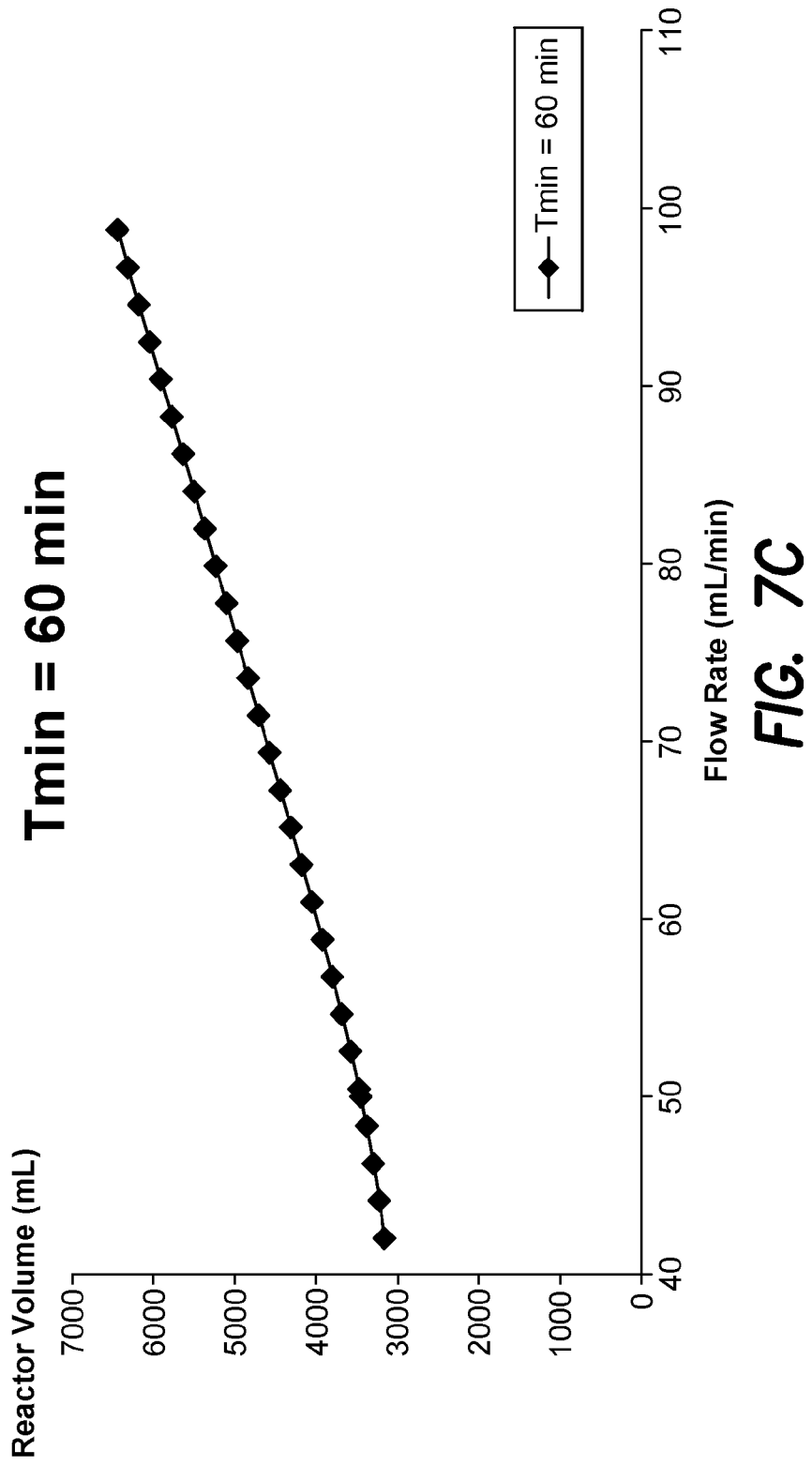
FIG. 7C is a graph illustrating the relationship of the flow rate and reactor volume for designing, selecting, making, and/or manufacturing the actual reactor, according to an example of the present disclosure.

Solving the equation above, L will equal to 108.99 m or a reactor volume of 3.46 L. Referring to FIG. 7C, a graphical representation can also be shown at 300, that illustrates all data points corresponding to flow rate Q and reactor volume RV combinations that result in a $T_{min}$ of 60 min.

In all of the above examples, the internal diameter i.d. and the radius of curvature of the experimental reactor 100 and the actual reactor 400 remain the same. However, in an example, as described below, the system can also design, select, make, manufacture, and recommend a reactor that includes an internal diameter i.d. of the reaction tube that differs from the internal diameter i.d. of the experimental reactor. This is especially useful when submitting data to regulatory agencies, such as the FDA, where applicable regulations require data to demonstrate compliance. The system below will allow a user to run a small scale process stream for data purposes and then scale it up for mass production, without having any significant changes to the process stream or final results of the process stream during scaled-up production.

Scaling Up or Down Using Aspect Ratio

Figure 8A:
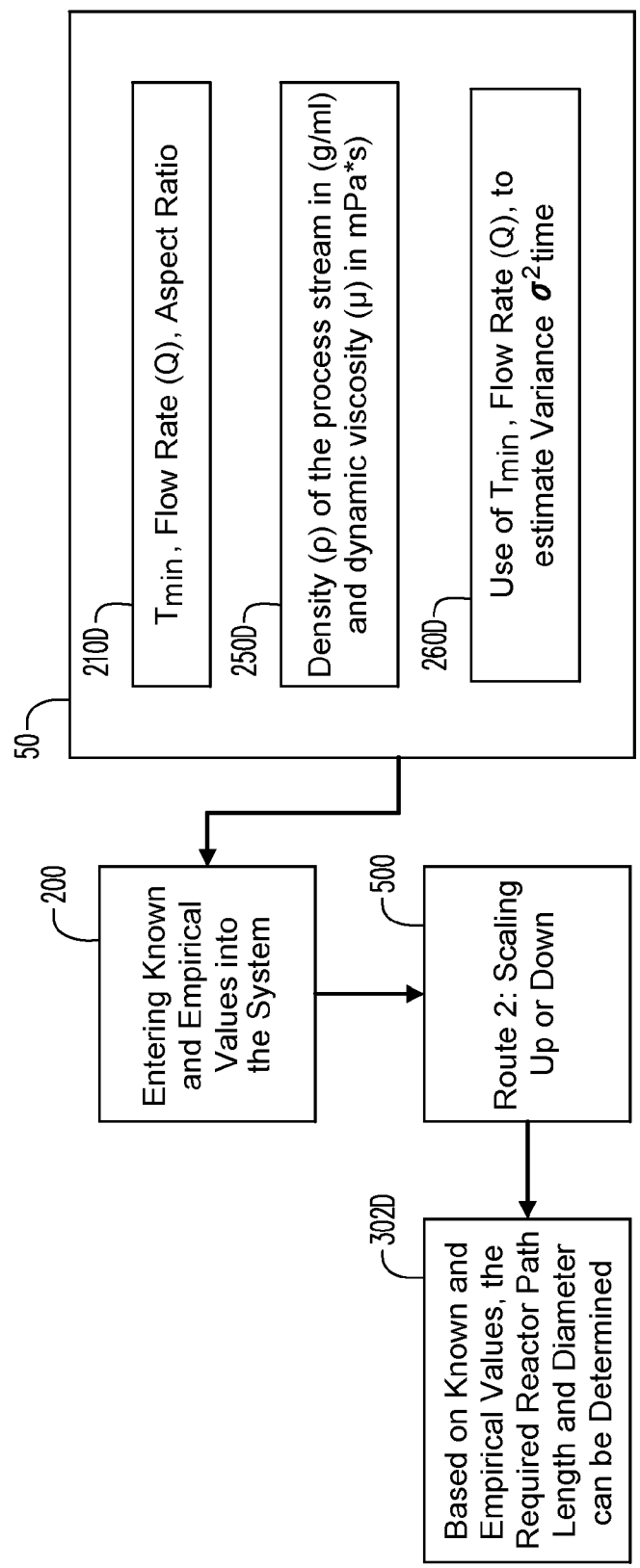
FIG. 8A illustrates the overview of how the system derives at an actual reactor path length and an internal diameter of the reaction tube, according to an example of the present disclosure.

In an example, a user, using the system 1000, can develop or create an actual reactor 400 based on a desired predetermined $T_{min}$ (60 min), process stream flow rate $Q_{Exit}$ (100 mL/min), density ρ, and the dynamic viscosity μ, and a known aspect ratio. For example, as shown in FIG. 8A, at 210D, the known reactor parameters can include $T_{min}$, process stream flow rate Q, and the aspect ratio. The aspect ratio can be defined as the radius of the reaction tube of the experimental reactor over the radius of curvature Rc of the experimental reactor. Moreover, the aspect ratio can be from about 0.01 to about 10, such as from about 0.05 to about 5, for example, from about 0.1 to about 0.5. Additionally, as also shown in FIG. 8A, at 250D, the known fluid-phase parameters can include density ρ and the dynamic viscosity μ of the fluid in the process stream. In this example, these known values can be entered into the comparator 50, so that it can determine the empirical values, such as variance $\sigma^2_{time}$ and the average residence time $T_{Ave}$.

Figure 8B:
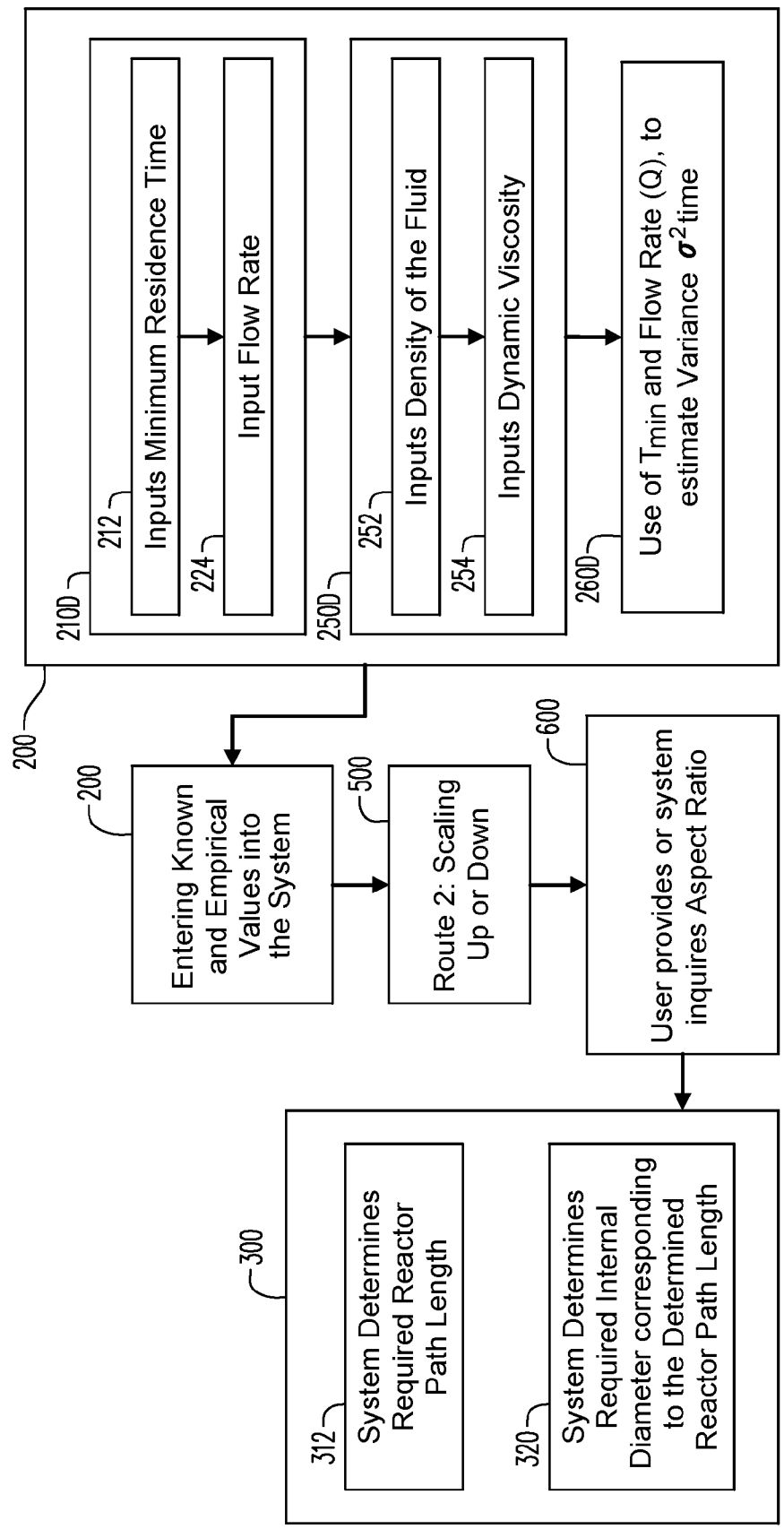
FIG. 8B illustrates the details of how the system derives at an actual reactor path length and the internal diameter of the reaction tube, according to an example of the present disclosure.

Referring to FIG. 8B, in this example, the $T_{min}$ (e.g., 60 min) can be entered into the system at 212 and the flow rate Q (e.g., 100 mL/min) of the process stream can be entered into the system at 224. Thus, in this particular example, the inputted values corresponding to the reactor parameters at 210D can be the $T_{min}$, and process stream flow rate Q.

Additionally, at 252, the density (ρ) of the fluid in the process stream can be entered into the system 1000. At 254, the dynamic viscosity μ can be entered into the system 1000. Thus, in this particular example, the inputted known values corresponding to the fluid-phase parameters at 250D can be density ρ and the dynamic viscosity μ.

To predict and/or determine the reaction tube flow path length L and the internal diameter i.d. of an actual reactor 400, the known values can be entered into the comparator

50. The comparator 50, at 260D, using the experimental reactor 100 as described above, can utilize the $T_{min}$ and the process stream flow rate Q to predict and/or determine the $T_{Ave}$ and variance $\sigma^2_{time}$, as shown in the equations below.

$$HETP = \frac{\sigma^2_{time} * L}{T^2_{Ave}} \quad (31)$$

HETP=$f(v)$=$(av^3+bv^2+cv+d)$, wherein $a$, $b$, $c$, and $d$ are based on empirical data fits for all Dean numbers (32)

$T_{Ave}$=$T$min+$(n*\sigma_{time})$, wherein $n$ can be 5 (33)

$T_{Ave}$=$T_{max}$−$(m*94_{time})$, wherein $m$ can be 3 (34)

$$T_{Ave} = \frac{L}{v} \quad (35)$$

$Q=v*CA$ (36)

$$CA = \prod * \left(\frac{i.d.}{2}\right)^2 \quad (37)$$

$$\sigma_{time} = \frac{1}{5} * \left(\frac{L}{v} - T\min\right) \quad (38)$$

By re-arranging the equations $$\sigma_{time} = \frac{f(v) * \frac{L}{v}}{\sqrt{L}} \quad (39)$$

Referring to FIGS. 8A and 8B, the empirical value equations above and the known values can be forwarded to the system at 200. In this particular example, the system at 500 can ask the user if the user would like to use the actual reactor has a substantially similar diameter as the experimental reactor. If the user replies yes, then the system can determine the length based on the example above and FIGS. 7A and 7B. However, if the user replies no or selects scaling of the reactor, then the system can acquire the aspect ratio and the processor 1001 of the system 1000 can solve for reactor length L in the equation below.

$$L=1/2*(25f(v)^2 \pm 5*\sqrt{25f(v)^4 f(v)^2 T\min * v} + 2 * T\min * v) \quad (40)$$

In an example, scaling of the reactor can include at least one of (i) scaling dimensions of the experimental reactor to the actual reactor having the same aspect ratio as the experimental reactor, but a different internal diameter; (ii) scaling the dimensions of the experimental reactor to the actual reactor having the same aspect ratio and a same internal diameter as the experimental reactor; (iii) scaling the dimensions of the experimental reactor to the actual reactor having a different aspect ratio than the experimental reactor and a different diameter than the experimental reactor; (iv) scaling the dimensions of the experimental reactor to the actual reactor having a different aspect ratio as the experimental reactor, but a same diameter as the experimental reactor.

Once L has been determined, the system 1000, based on the derived values of reactor length L, standard deviation $\sigma_{time}$, and the average linear flow velocity (cm/min), can determine the internal using the equations below:

$$A = \prod r^2 = \prod \left(\frac{i.d.}{2}\right)^2 T_{Ave_{Defined}} = \frac{L}{v} = \frac{CA * L}{Q} \quad (41)$$

$$T_{Ave_{Defined}} = \frac{CA * L}{Q} \quad (42)$$

$$\frac{Q * T_{Ave_{Defined}}}{L * \prod} = r^2 \quad (43)$$

$$i.d. = 2\sqrt{\frac{Q * T_{Ave_{Defined}}}{L * \prod}} \quad (44)$$

For this particular example, in order to design, select, make, and/or manufacture the actual reactor having a fixed aspect ratio a plot can be derived between the HETP and the linear flow velocity. For example, FIG. 8C can be derived from an experimental small size reactor having a fixed aspect ratio with an internal diameter of from about 0.1 cm to about 0.2 cm, such as 0.156 cm tested with water and an experimental medium-size reactor having the same fixed aspect ratio with an internal diameter of from about 0.6 cm to about 0.7 cm, such as 0.635 cm tested with water and dextrose.

Figure 8C:
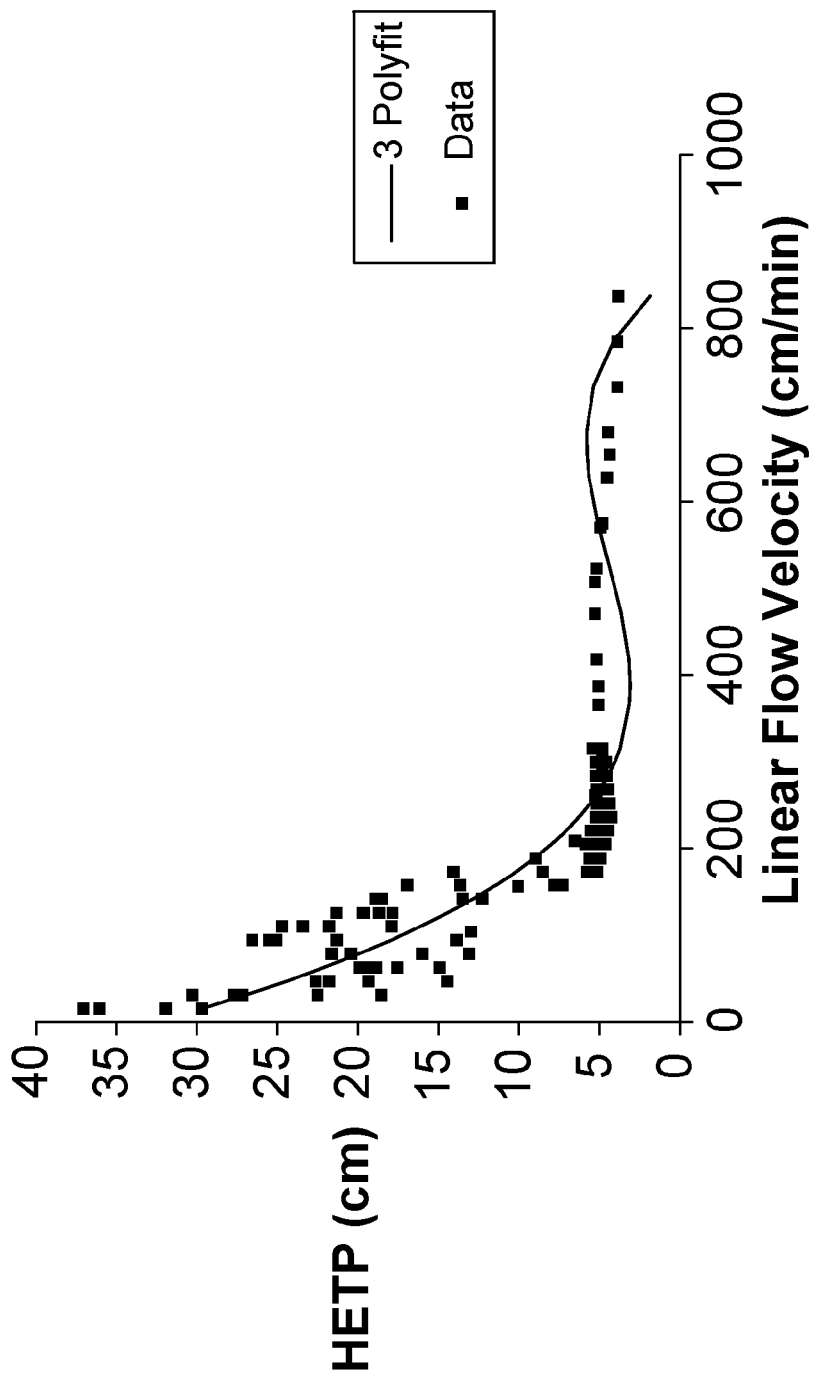
FIG. 8C is a graph of HETP vs the linear flow velocity, according to an example of the present disclosure.
Figure 8D:
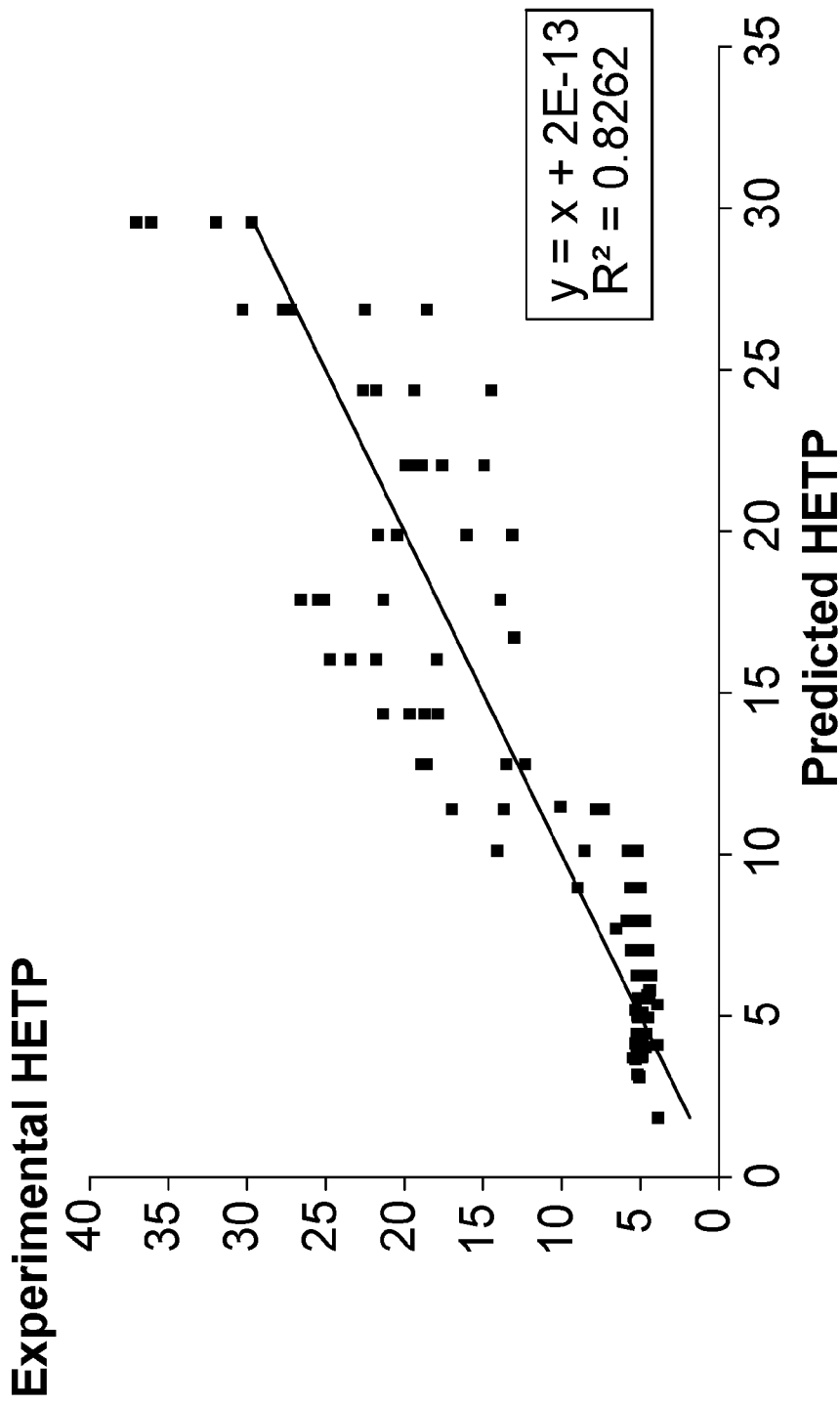
FIG. 8D is a graph of predicted vs the actual HETP, according to an example of the present disclosure.

FIG. 8D is a plot between experimental HETP and the predicted HETP that illustrates the parity between the predicted HETP based on FIG. 8C and the experimental HETP.

Figure 8E:
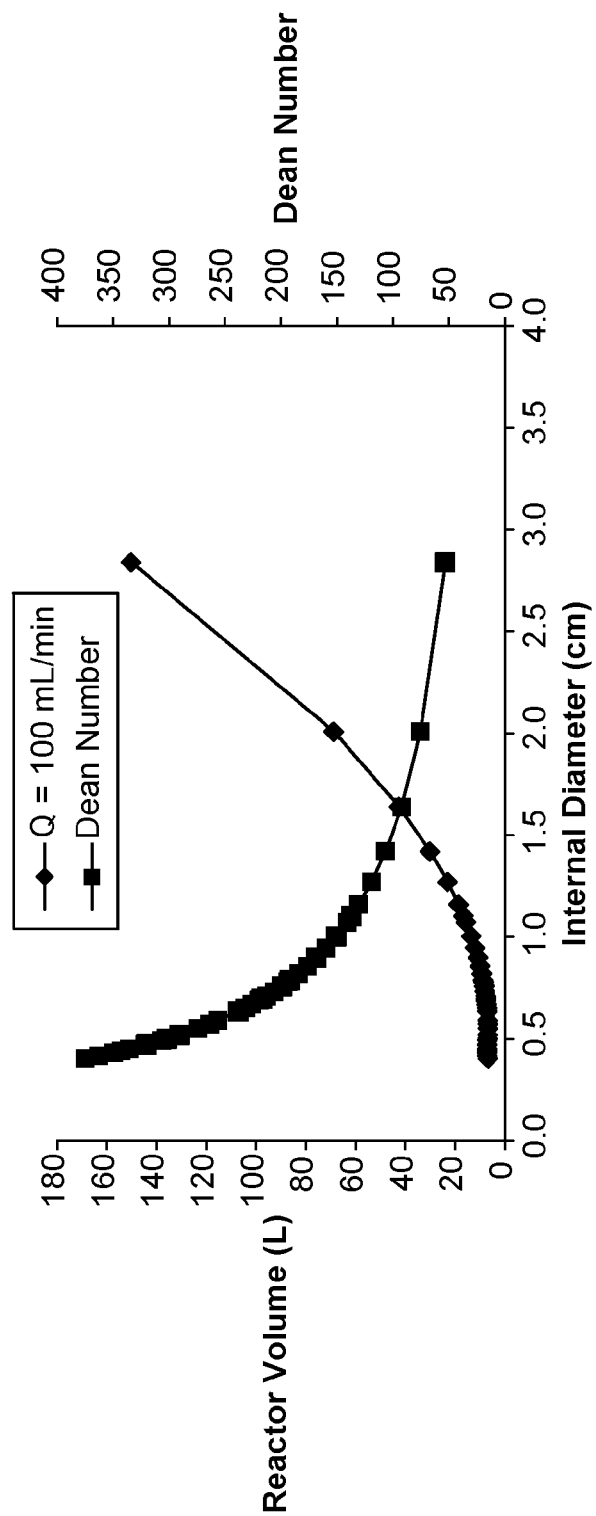
FIG. 8E is a graph showing the reactor volume and internal diameters that satisfy a predetermined flow rate and $T_{min}$, according to an example of the present disclosure.

As shown at 312 and 320 of FIG. 8B, the reactor path length and the internal diameter of an actual reactor can be derived and/or determined. As shown in FIG. 8E, based on the derived reactor path length, the derived internal diameter, and the predicted HETP values, a plot can be created that illustrate all solutions for reactor volume and internal diameter that satisfies Q=100 mL/min and $T_{min}$=60.

FIG. 9 illustrates an exemplary embodiment, where the system 1000 can determine the ideal reactor given the fluid and the reactor volume. In this example, as prior examples above, the user can enter the known parameters into the comparator 50. The comparator 50, based on the known values, can determine the empirical values, which can be entered into the system 1000 at 200. The non-empirical values, such as the reactor tube length L can then be determined at 300 as described above. Given the reactor length, the system can determine the reactor volume at 700. The system, at 750, based on the known fluid characteristics, detectable particles/tracer, and the determined volume of the reactor, can communicate with a database 770. The database 770 can include previously designed or manufactured reactors based on volume of the reactor and known fluid and detectable particle/tracer parameters. The database 770 can then provide the system 1000 with a list of different actual reactors each having substantially similar volume that was used with similar fluid and detectable particles/tracer that accomplish the same desired end result. The processor 1001 of the system 1000, can then review the list of the provided actual reactors to select a best actual reactor 400 for the intended purpose.

Figure 10A:
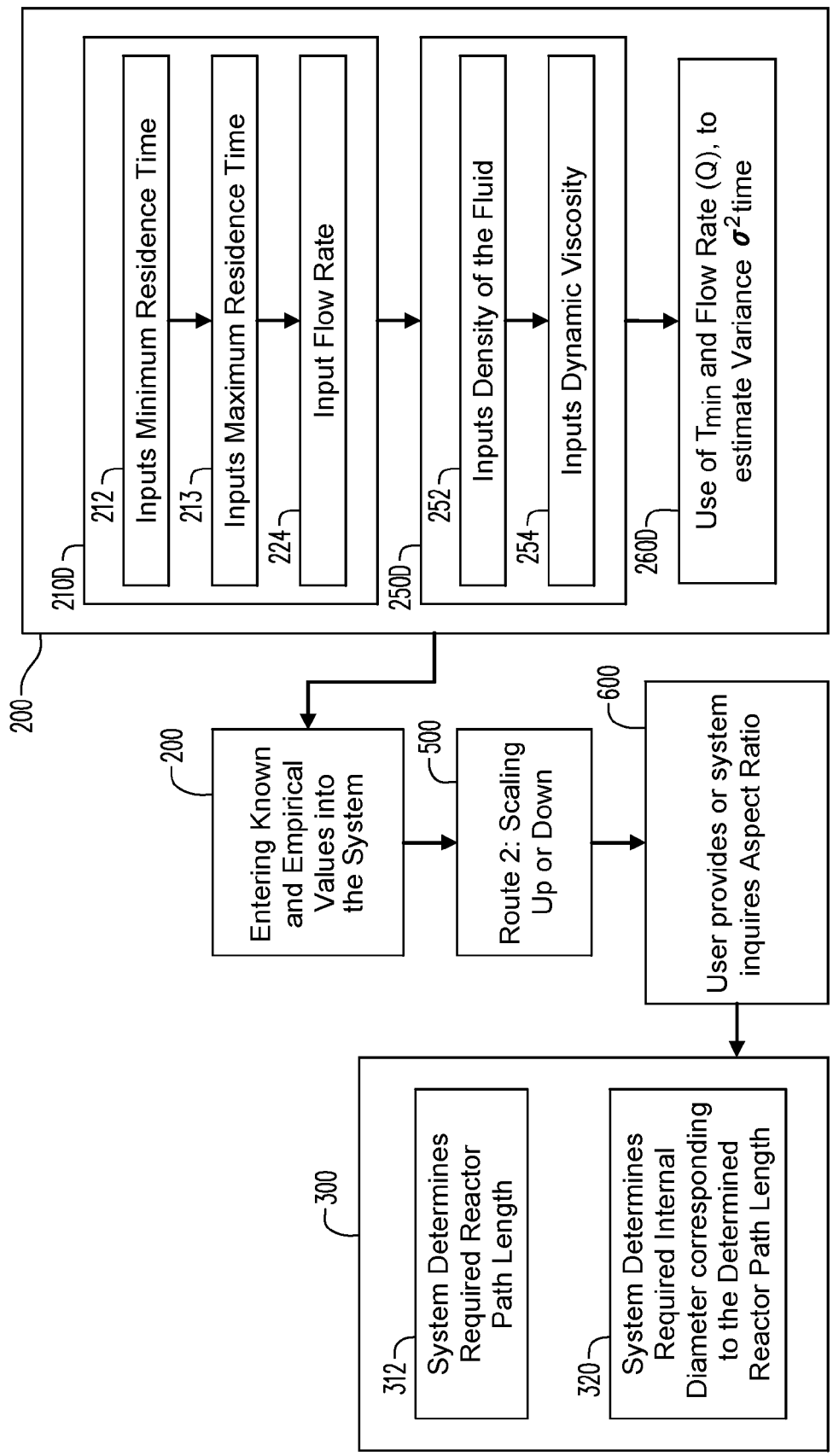
FIG. 10A illustrates the details of how the system derives at an actual reactor path length and the internal diameter of the reaction tube, according to an example of the present disclosure.

Referring to FIG. 10A, in another example, the $T_{min}$ (e.g., 60 min) can be entered into the system at 212, the $T_{max}$ (e.g.

75 min) can be entered into the system at 213, and the flow rate Q (e.g., 500 mL/min) of the process stream can be entered into the system at 224. Thus, in this particular example, the inputted values corresponding to the reactor parameters at 210D can be two $T_{min}$ and a process stream flow rate Q. Additionally, the aspect ratio at 600 can be entered at this time or at a later time, as discussed below.

Additionally, at 252, the density (ρ) of the fluid in the process stream can be entered into the system 1000. At 254, the dynamic viscosity μ can be entered into the system 1000. Thus, in this particular example, the inputted known values corresponding to the fluid-phase parameters at 250D can be density ρ and the dynamic viscosity μ.

To predict and/or determine the reaction tube flow path length L and the internal diameter i.d. of an actual reactor 400, the known values can be entered into the comparator 50. The comparator 50, at 260D, using the experimental reactor 100 as described above, can utilize the $T_{min}$, $T_{max}$, and the process stream flow rate Q to predict and/or determine the $T_{Ave}$ and variance $\sigma^2_{time}$, as shown in the equations below.

$$T_{Ave} = T_{min} + (n*\sigma_{max}), \text{ wherein } n \text{ can be 5} \quad (45)$$

$$T_{Ave} = T_{max} - (m*\sigma_{max}), \text{ wherein } m \text{ can be 3} \quad (46)$$

$$\Delta T = 8\sigma_{max} \quad (47)$$

$$15 = 8\sigma_{max}$$

$$\sigma_{time} = 1.875 \text{ min}; \sigma^2_{time} = 3.52 \text{ min}^2; T_{Ave} = 69.375 \text{ min}$$

Figure 10B:
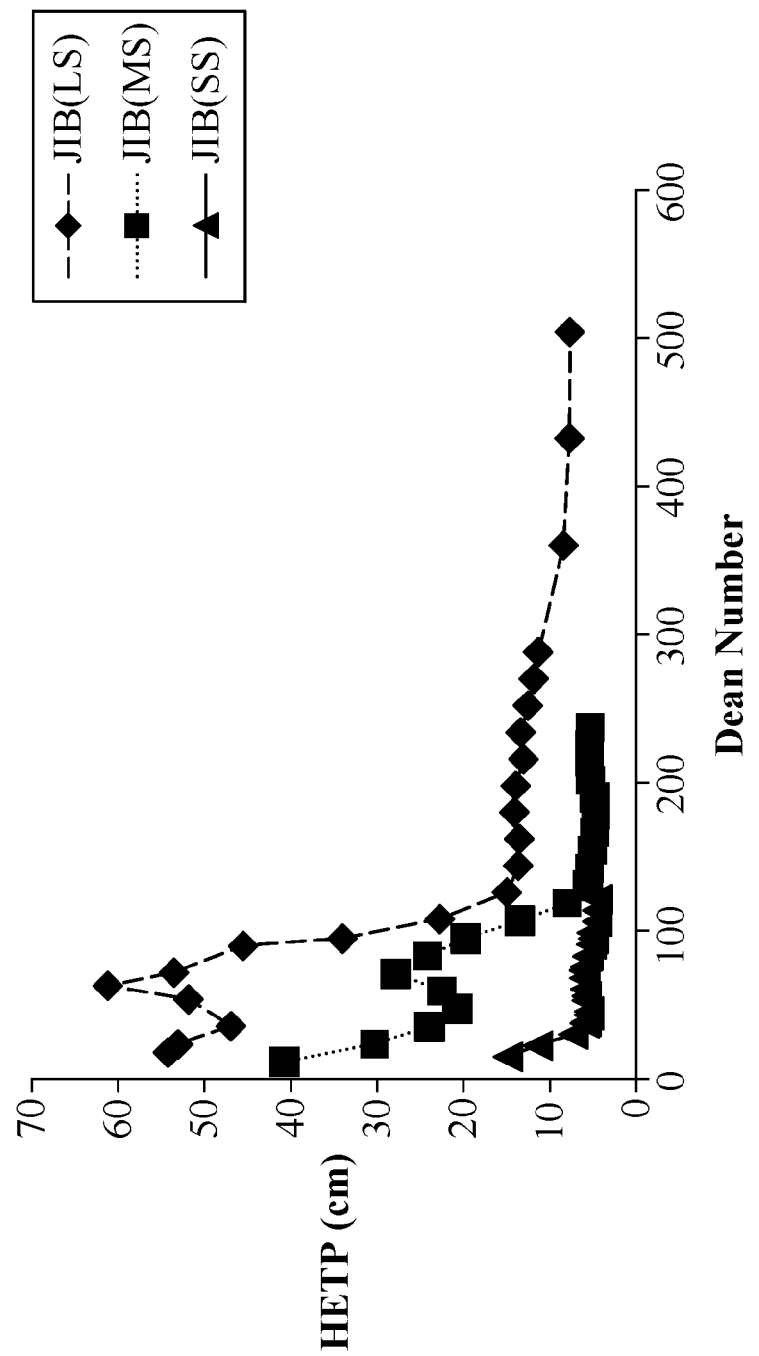
FIG. 10B is a graph illustrating the relationship between HETP and Dean Number by using a small-size JIB, a medium-size JIB, and a large-size JIB, according to an example of the present disclosure.
Figure 10C:
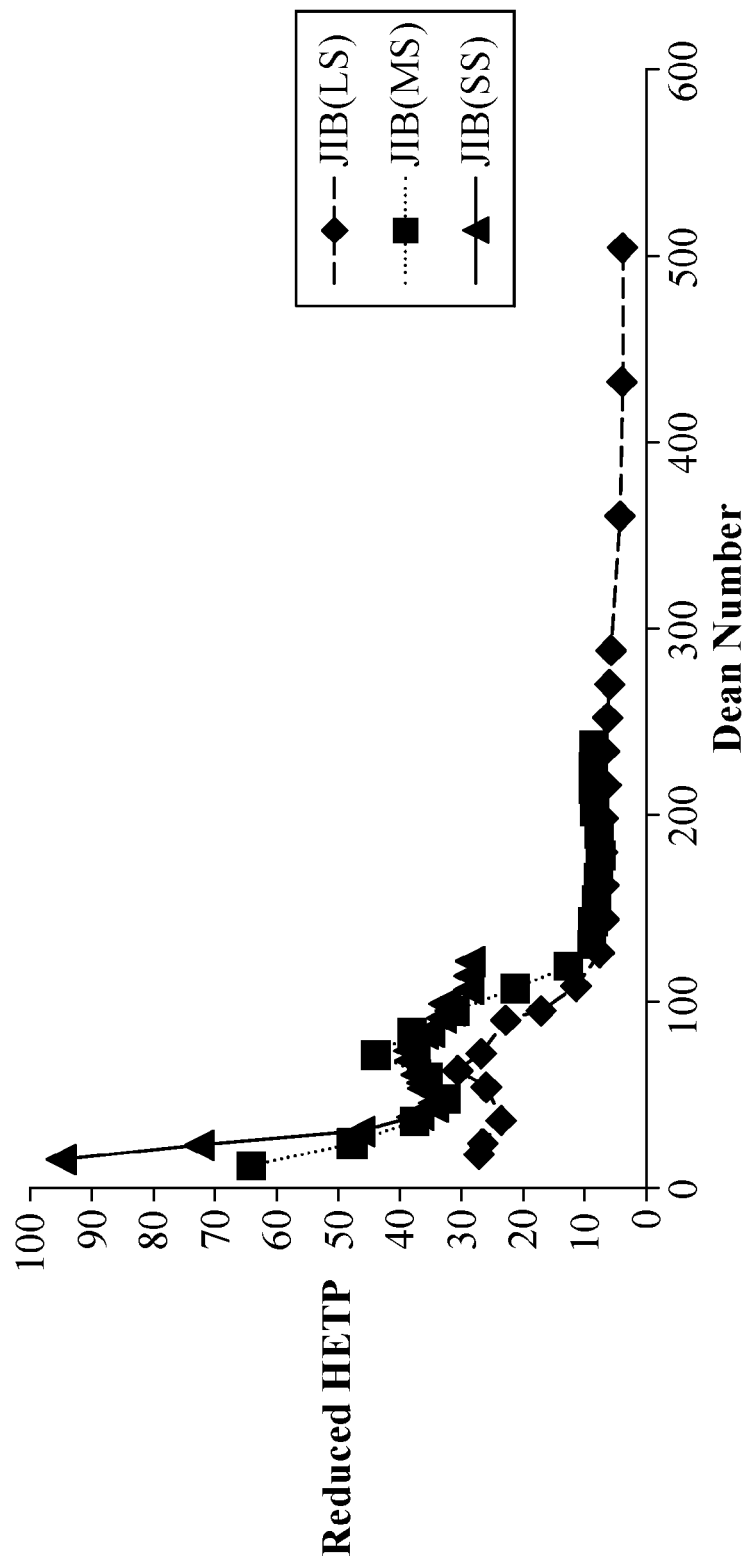
FIG. 10C is a graph of FIG. 10B when HETP is normalized by internal diameter, according to an example of the present disclosure.

Referring to FIG. 10A, the empirical value equations above and/or their corresponding values and the known values can be forwarded to the system at 200. In this particular example, the system at 500 can ask the user if the user would like to use the actual reactor has a substantially similar diameter as the experimental reactor. If the user replies yes, then the system can determine the length based on the example above and FIGS. 7A and 7B. However, if the user replies no or selects scaling of the reactor, then the system can acquire the aspect ratio and the processor 1001 of the system 1000 can divide the experimental HETP experimental data points by JIB internal diameter of a small, a medium, and a large reactor, as shown in FIG. 10B. The system can then fit a curve to the dataset, as shown in FIG. 10C. Using the equations below, the system can then graph the path length versus internal diameter for a flow rate of 500 mL/min at a $T_{min}$ of 60 and a $T_{max}$ of 75.

$$HETP = \frac{\sigma^2_{time} * L}{T^2_{Ave}} \quad (48)$$

$$\frac{HETP}{i.d.} = h = (aDe^3 + bDe^2 + cDe + d) = f(De) \quad (49)$$

a, b, c, and d are based on empirical data fits for all Dean numbers $$HETP = (h*i.d.) = \frac{\sigma^2_{time} * L}{T^2_{Ave}} * i.d. \quad (50)$$

Figure 10D:
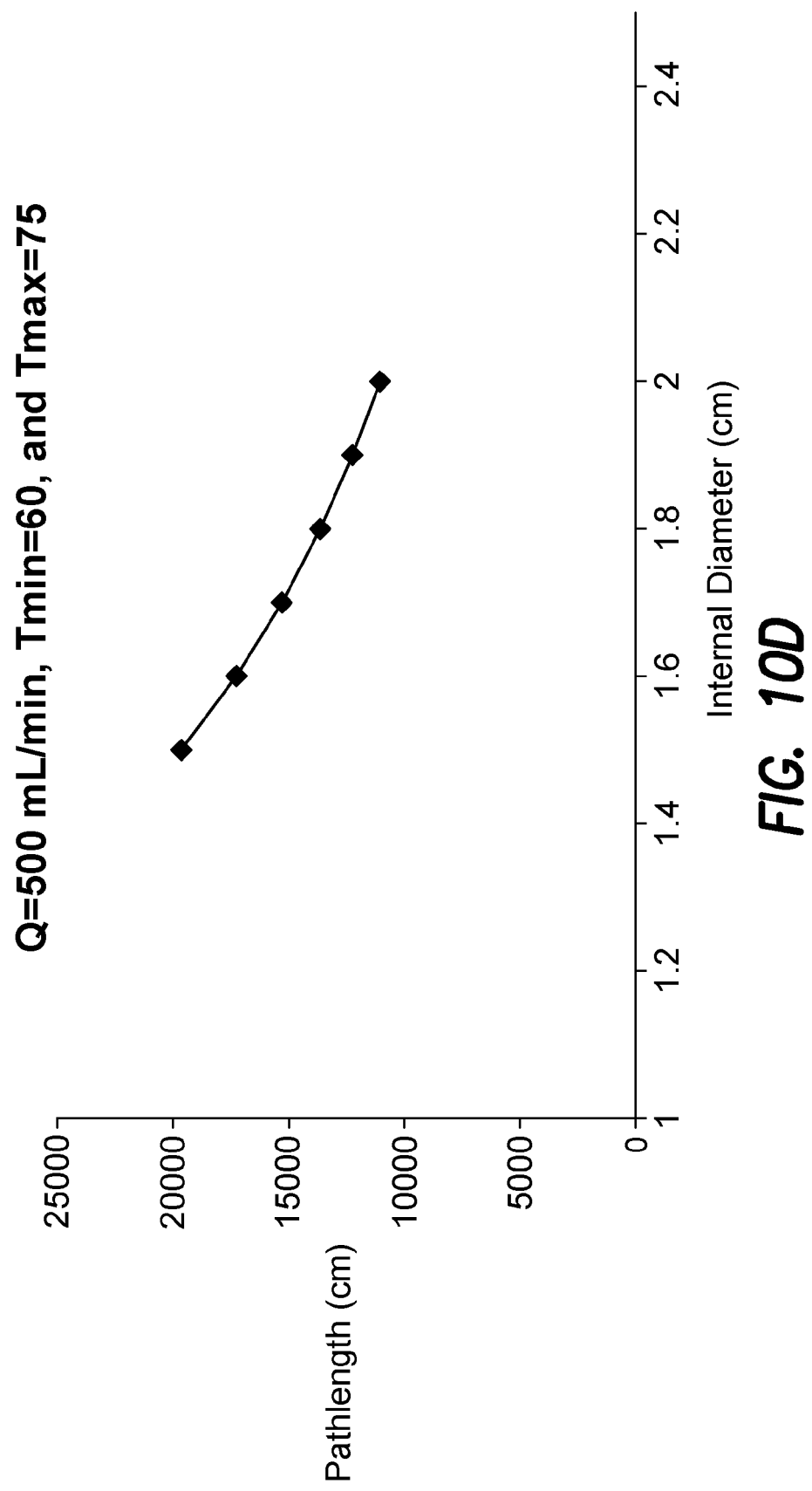
FIG. 10D is a graph illustrating the relationship between the path length and the internal diameter at a flow rate of 500 mL/min having a Tmin of 60 and a Tmax of 75, according to an example of the present disclosure.

Fixing an i.d. returns a path length term as shown in FIG. 10D.

Example 1

Residence Time Distribution Generation.

The JIB was designed from previous development projects at Boehringer Ingelheim and was 3D printed utilizing SLA Technology by 3D Systems (Rock Hill, SC). The riboflavin and dextrose used in creating the mobile phases and pulse tracer were purchased through Thermo Fisher Scientific (Suwanee, GA). The viscosities of the solutions were determined by a microVISC S Viscometer utilizing an A05 Chip (San Ramon, CA). The densities of the solutions were determined by a Mettler-Toledo Densito Densometer (Columbus, OH).

The mid-scale 3D printed JIB was tested using an Akta Avant 150, while the large-scale JIB was tested using an Akta Pilot 600 by GE Healthcare (Uppsala, Sweden). The JIB was first flushed with 1 reactor volume of the mobile phase. Next, a fixed volume of riboflavin dissolved in the mobile phase was pulse injected and chased out with the mobile phase. This produced the Residence Time Distribution (RTD) profiles upon exiting the reactor detected and quantified by UV-Vis absorbance at riboflavin's absorbance maximums (i.e. 267, 372, and 445 nm). The RTD peaks were then analyzed by fitting a Gaussian distribution. From this fit, the variance of the peak, $\sigma^2_{time}$ which is a measurement of the spread of the RTD, was determined. This method was tested over a series of flow rates and viscosities which were altered by varying concentrations of dextrose. The $\sigma^2_{time}$ values were converted into HETP. An HETP vs. Dean number graph was created and a $3^{rd}$ order polynomial was fit. Then the following series of equations were utilized:

1. Start governing Equations $$HETP = \frac{\sigma^2_{time} * L_{T_{Ave}}}{T^2_{Ave}} \quad a)$$

$$\sqrt{HETP} = f(De) = \frac{\sigma_{time} * \sqrt{L_{T_{Ave}}}}{T_{Ave}} = (aDe^3 + bDe^2 + cDe + d) \quad b)$$

i. a, b, c, and d are based on empirical data fits only valid for Dean numbers ≥100 c) $T_{Ave} = T\min + (5*\sigma_{time})$ $$T_{Ave} = \frac{RV}{Q} = \frac{CA * L_{T_{Ave}}}{Q} \quad d)$$

2. Re-arrange Equations $$\sigma_{time} = \frac{1}{5} * \left( \frac{CA * L_{T_{Ave}}}{Q} - T\min \right) \quad e)$$

$$\sigma_{time} = \frac{f(De) * \frac{CA * L_{T_{Ave}}}{Q}}{\sqrt{L_{T_{Ave}}}} \quad f)$$

3. Solve for L:

$$L_{T_{Ave}} = \frac{25*CA^2*f(De)^2 \pm 5*\sqrt{\begin{array}{c}25*CA^4*f(De)^4 + \\ 4*CA^3* \\ f(De)^2*Q*T_{min}\end{array}} + 2*CA*Q*T_{min}}{2CA^2}$$

4. Fill Variables

| mAb Concentration (g/L) | Approximate Kinematic viscosity (m²/s) |
|---|---|
| 10 | $1.2 \times 10^{-6}$ |
| 20 | $1.4 \times 10^{-6}$ |
| 50 | $2.0 \times 10^{-6}$ |

The tables below indicate the Tmin at 15 min, 30 min, and 60 min for mid-scale and large-scale reactors.

Mid-scale (0.635 cm i.d.) at 50 mL/min

| | Max Protein Concentration (g/L) | | |
|---|---|---|---|
| | 10 | 20 | 50 |
| | Reactor Volume (L) | | |
| Tmin = 15 min | 1.13 | 1.22 | 1.43 |
| Tmin = 30 min | 2.00 | 2.12 | 2.38 |
| Tmin = 60 min | 3.68 | 3.83 | 4.16 |

Large-scale (2 cm i.d.) at 500 mL/min

| | Max Protein Concentration (g/L) | | |
|---|---|---|---|
| | 10 | 20 | 50 |
| | Reactor Volume (L) | | |
| Tmin = 15 min | 10.47 | 10.47 | 10.47 |
| Tmin = 30 min | 19.00 | 19.00 | 19.00 |
| Tmin = 60 min | 35.46 | 35.46 | 35.46 |

Evaluating the Effect of Flow Mechanics on Critical Process Parameters in a Continuous Viral Inactivation Reactor The JIB was designed from previous development projects and was 3D-printed utilizing SLA Technology by 3D Systems (Rock Hill, SC). The riboflavin and dextrose used in creating the mobile phases and pulse tracer were purchased through Thermo Fisher Scientific (Suwanee, GA). The viscosities of the solutions were determined by a microVISC S Viscometer utilizing an A05 Chip (San Ramon, CA). The densities of the solutions were determined by a Mettler-Toledo Densito Densometer (Columbus, OH).

The small scale and mid-scale 3D-printed JIB were tested using an Akta Avant 150, while the large-scale JIB was tested using an Akta Pilot 600 by GE Healthcare (Uppsala, Sweden). The JIB was first flushed with 1 reactor volume of the mobile phase. Next, a fixed volume of riboflavin dissolved in the mobile phase was pulse injected and evacuated with the mobile phase. This produced the RTD profiles upon exiting the reactor detected and quantified by UV-Vis absorbance at riboflavin's absorbance maximums (i.e. 267, 372, and 445 nm). The internal diameters, flow rates, mobile phases, and a number of JIBs connected in series tested in this study are outlined in Table 1 below.

g) TABLE 1

An outline of all of the mobile phases, internal diameters, path lengths, and flowrate combinations tested via pulse injection experiments using the JIB

| Scale | Internal Diameter (cm) | Number of JIB's connected in Series | Mobile Phase | Flow Rates Tested |
|---|---|---|---|---|
| Small Scale | 0.156 | 1 (L = 11.09 m) | DI Water | 1-16 mL/min |
| Mid Scale | 0.635 | 1 (L = 16.44 m) | DI Water | 5-100 mL/min |
| | | 2 | DI Water | |
| | | 6 | DI Water | |
| | | 1 | 50 g/L Dextrose | |
| | | 1 | 100 g/L Dextrose | |
| | | 1 | 200 g/L Dextrose | 10-125 mL/min |
| Large-scale | 2.0 | 1 (L = 16.60 m) | DI Water | 25-700 mL/min |

The peaks were then analyzed by fitting a Gaussian distribution. From this fit, the variance of the peak, ($\sigma_{time}^2$), which is a measurement of the spread of the RTD, was determined. To better understand the influence of the quantitative value of the variance, Equation 1 was calculated, where Q is the volumetric flow rate. Additionally, the dataset was converted using Equations 2 and 3 where HETP is height equivalent to a theoretical plate, $T_{Ave}$ is the mean residence time, RV is reactor volume, and L is the length of the flow path of the JIB.

$$\sigma_{Volume} = \sqrt{\sigma_{time}^2 * Q^2} \quad (1)$$

$$HETP = \frac{\sigma_{time}^2 * L}{T_{Ave}^2} \quad (2)$$

$$T_{Ave} = \frac{RV}{Q} \quad (3)$$

Flow Rate and Path Length

Figure 11A:
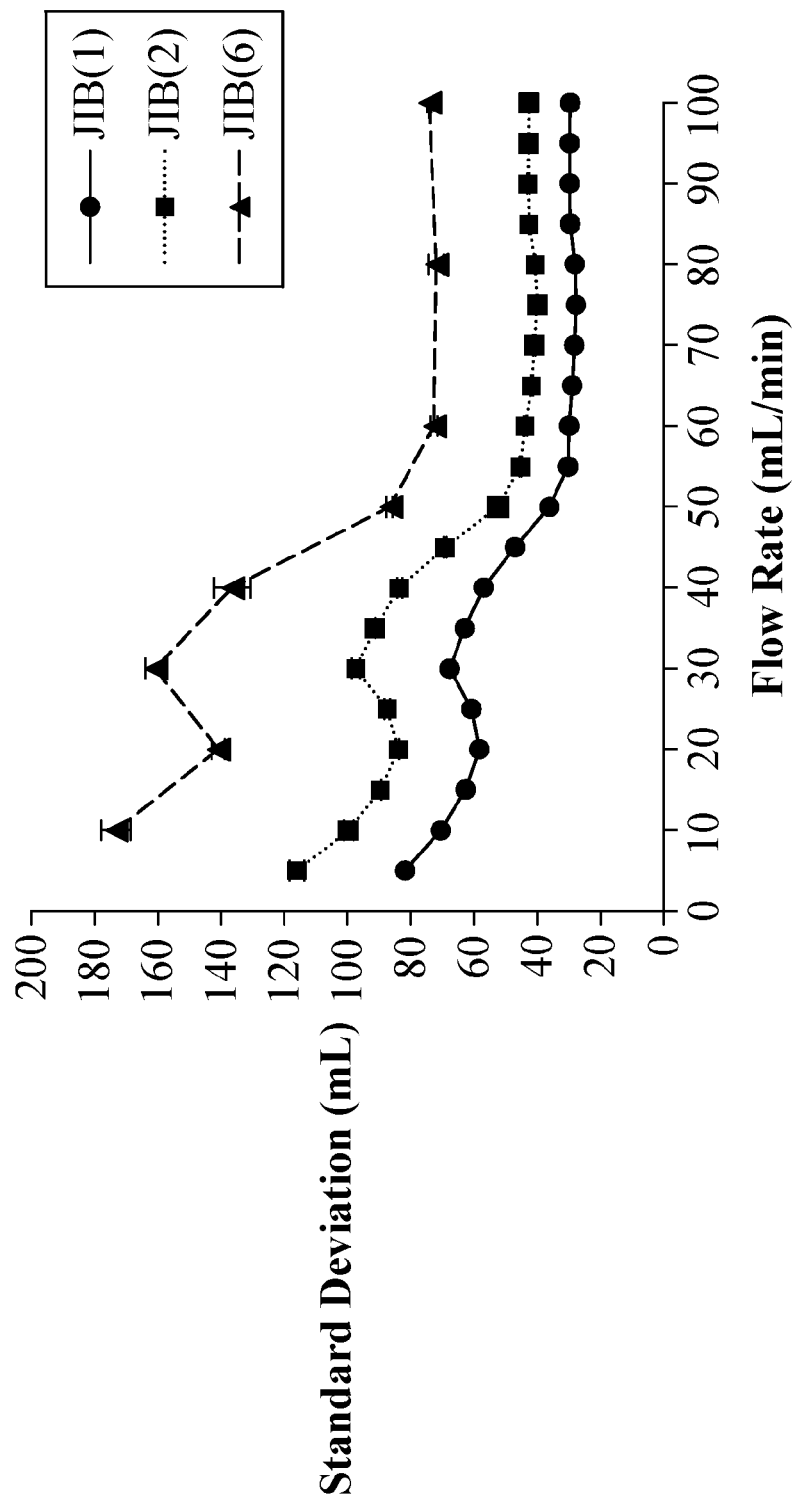
FIG. 11A is a graph illustrating the volumetric spreading reaction of an exiting pulse injection from variable flow rate and path length of JIB operation, according to an example of the present disclosure.

As seen in FIG. 11A, the slowest flow rate produces the widest peak for all three reactor sizes. This is shown in the graph as having a relatively high standard deviation (ex. ~82 mL for the JIB(1) dataset at 5 mL/min) which describes the volume distance from the center of the peak (i.e. $T_{Ave}$) to 34% of total mass to the left or right. As the flow rate increases the peak narrows, with the standard deviation decreasing at an exponential rate. However, an inflection point is attained when the flow rate increases above 20 mL/min. The peak becomes wider until another inflection point is reached at the 30 mL/min set point. With the flow rate increasing higher, the peaks substantially narrow until the 55 mL/min set point. In total, the progression from slower to faster flow rate displays an initial asymptote, two inflection points, and finally a second asymptote. Looking at the JIB(1), JIB(2) and JIB(6) data in FIG. 11A, the phenomenon of 2 asymptotes and 2 inflection points is maintained at identical flow rates across all path lengths.

Figure 11B:
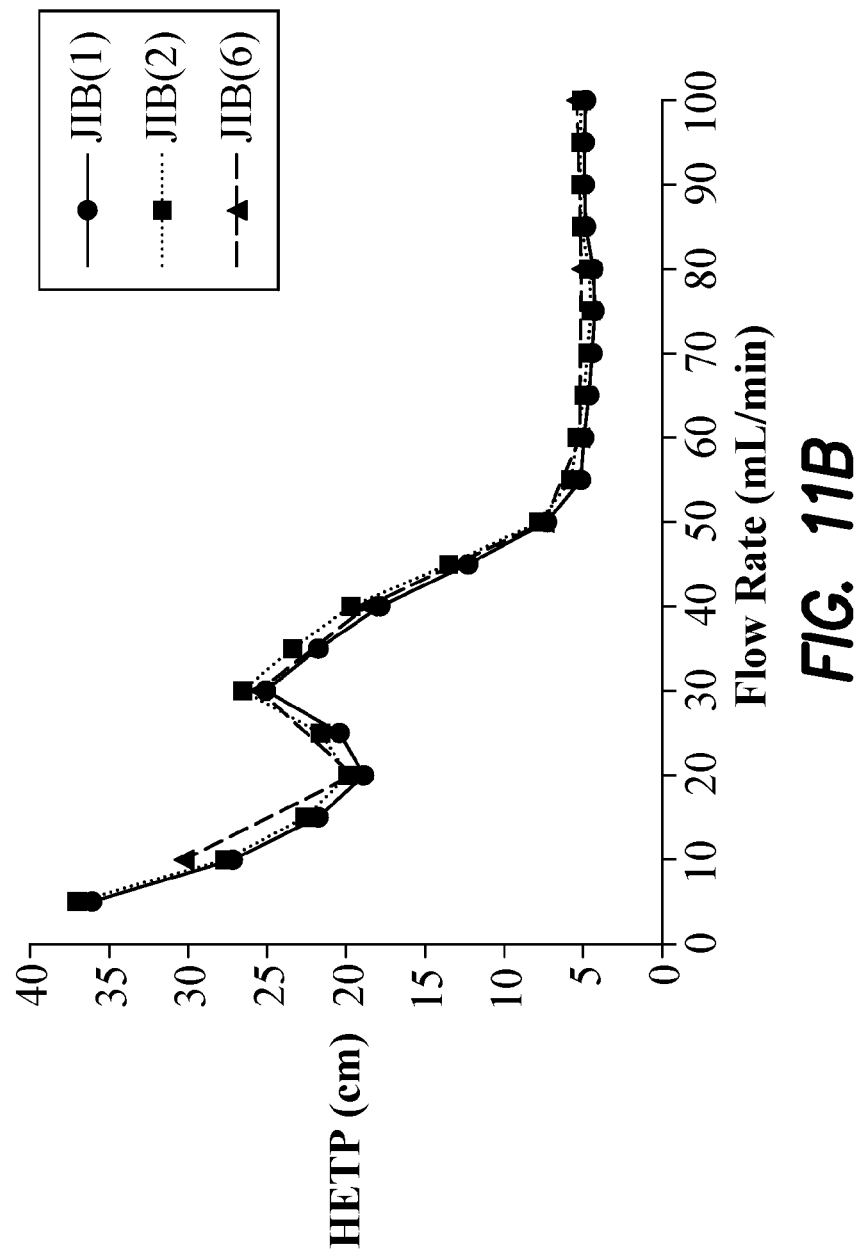
FIG. 11B is a graph illustrating the normalization of the path lengths by HETP, according to an example of the present disclosure.

Comparing the path length, the peaks widen with the longer path length. This is a well-characterized observation that is a reproducible phenomenon for PFR's. When the data points from FIG. 11A are translated using Equation 3 and converted into height equivalent to an HETP, FIG. 11B is created making the three path length's datasets overlay.

Figure 12:
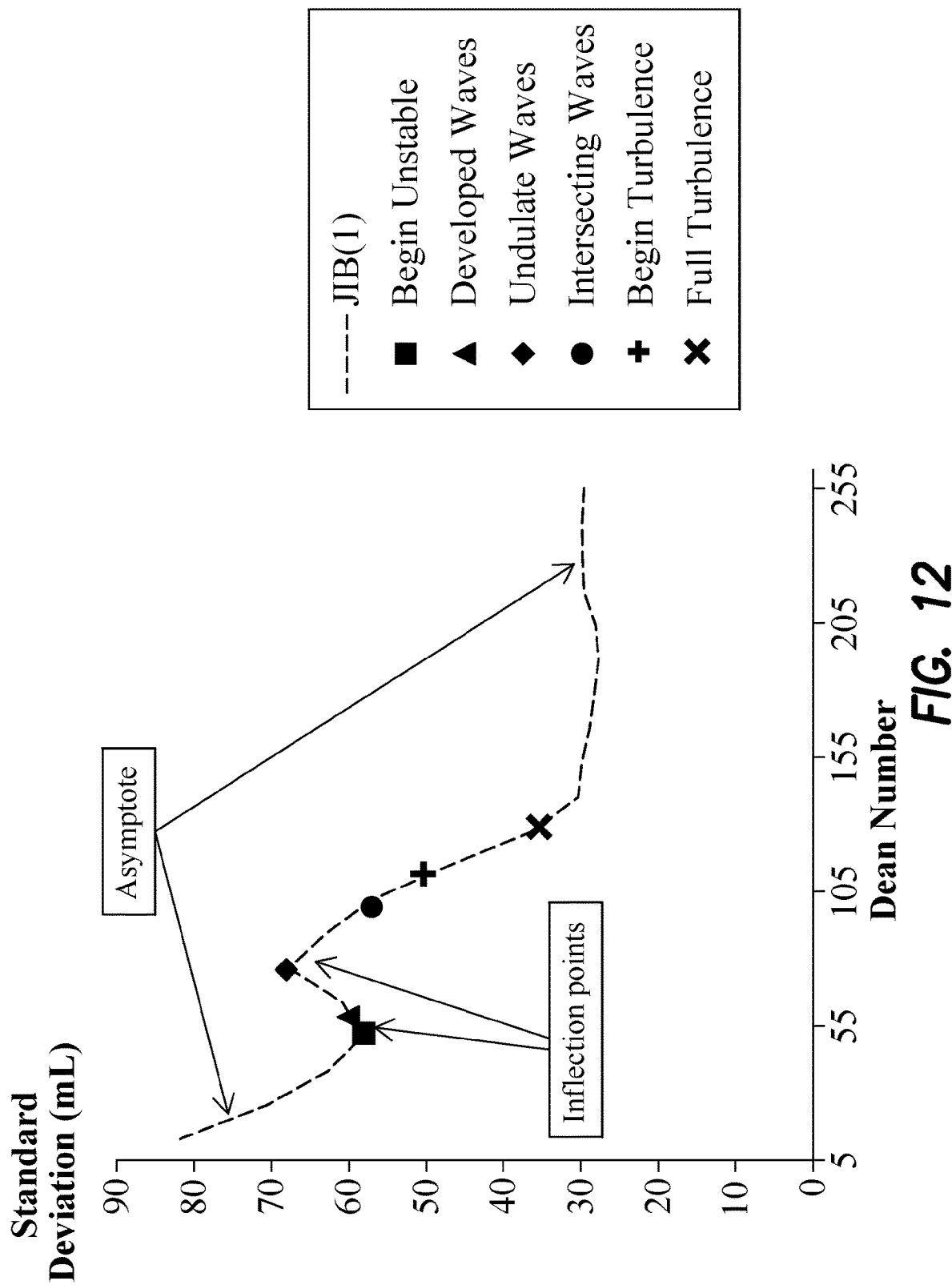
FIG. 12 is a graph illustrating the correlation of the Dean Numbers required to generate transitions in Taylor-Couette flow and the two inflection points and asymptote created in the spreading of the RTD profiles of the JIB, according to an example of the present disclosure.

To understand the driving force for this shift (i.e. the two inflection points), further exploration into previously published work on Dean Vortices was undertaken. Flow patterns were visualized using suspensions in water when between two rotating drums (i.e. Taylor-Couette flow). As the flow increased in velocity in the flow cell, Aider made observations at specific Dean number's at which the flow patterns shifted from laminar to chaotic. A similar experiment was conducted in the JIB using suspended mica in water and found the same laminar to a chaotic flow transition. These specific Dean numbers and corresponding observations outlined in Aider et al. are co-plotted on FIG. 12. Dean number is defined by Equation 4, where ρ is the fluid density, u is average linear flow velocity, D is a flow path internal diameter, μ is dynamic viscosity, and $R_c$ is the radius of curvature of the serpentine pattern.

$$De = \left(\frac{\rho u D}{\mu}\right) * \sqrt{\frac{D}{2R_c}} \quad (4)$$

The two inflection points and the faster flow rate asymptote correspond to the visually observable manifestations of the flow transitioning from the onset of unstable flow, undulated waves, and full turbulence respectively. Given that for flow in a circular straight pipe, the onset of turbulence is typically observed at a Reynolds number of ~2000. The JIB was able to simulate turbulent flow behavior at a Reynolds number of ~174. Due to this large discrepancy, the term "weak turbulence" was used.

Figure 13A:
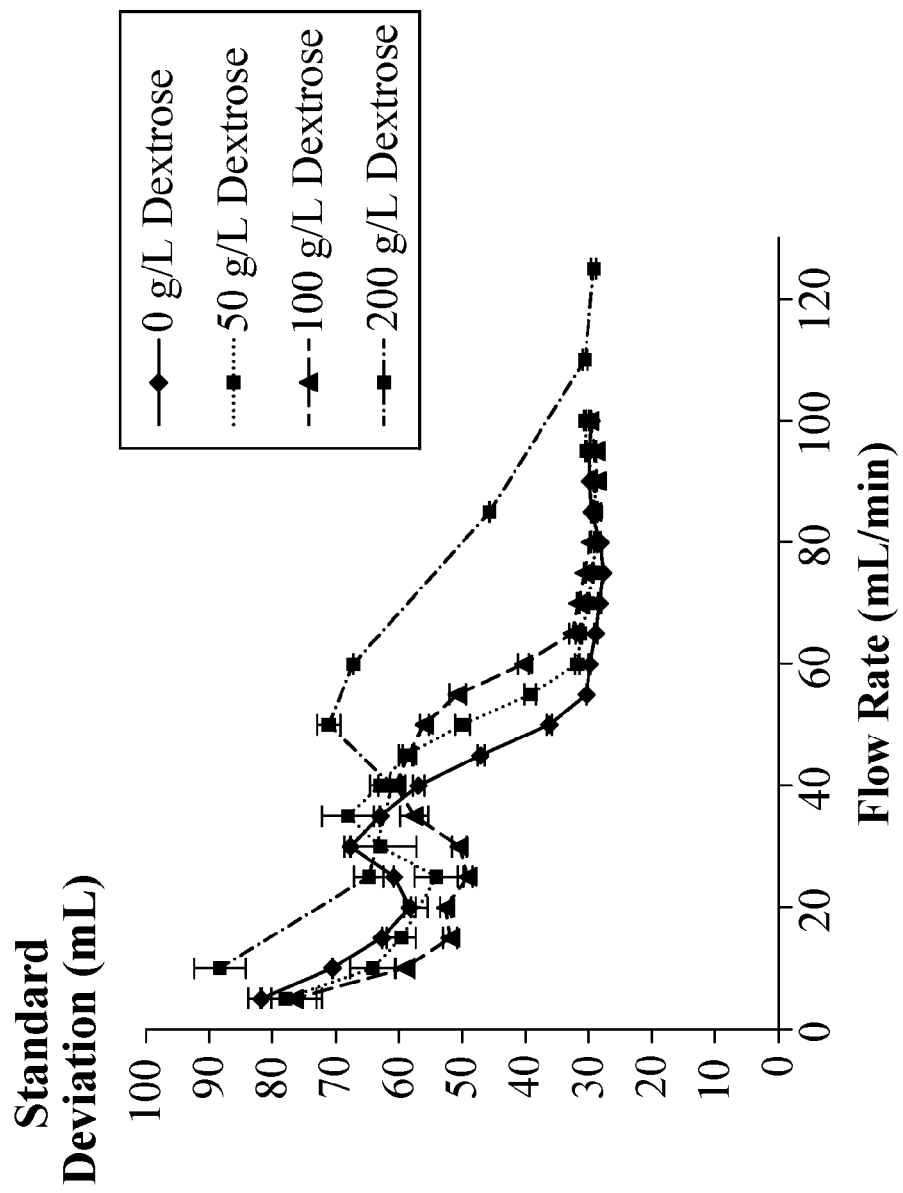
FIG. 13A is a graph illustrating the reaction of exiting pulse injection from variable flow rate and viscosity of JIB operation, according to an example of the present disclosure.

In order to prove the validity of the shift of 2 asymptotes and 2 inflection points behavior found in the section above was controlled by the Deans number, the mobile phase's viscosity was increased with three concentrations of dextrose. FIG. 13A displays the reaction of the addition of the dextrose. For all four mobile phases, the standard deviation began at its highest value at the slowest flow rate and narrowed with the increase in flow rate. However, with the increase in dextrose concentration and higher viscosity, the flow rate required to reach inflection point 1 increased. The same is true for inflection point 2 and flow rate required to reach the 2nd asymptote.

Figure 13B:
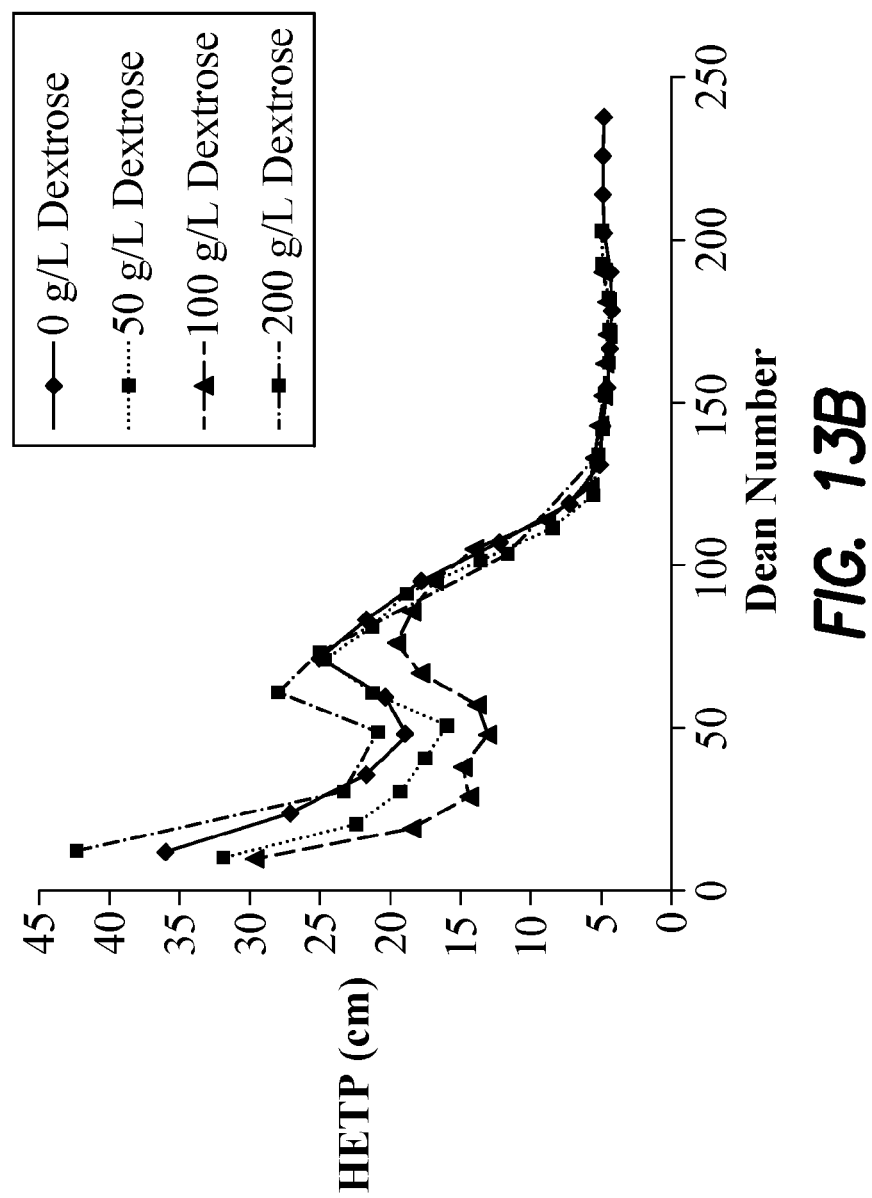
FIG. 13B is a graph illustrating the normalization of the various viscosity experimental HETP by Dean Number, according to an example of the present disclosure.

To account for this apparent shift in the inflection points and asymptote, the x-axis was normalized by converting the flow rate to Dean Number described in Equation 4 and shown in FIG. 13B. Once normalized to the Dean Number, the asymptotes and inflection points align. While the shift in the dataset returns to normal with the correction, the magnitude of the spreading appears only to be corrected for the higher Dean Number (i.e. De>100) operation. This is due to Dean Vortices taking over the radial mass transfer above De=70. For the lower Dean numbers (De<70), where other dispersion mechanisms dominate, the mobile phase's rank from most wide to most narrow is 200, 0, 50, and 100 g/L Dextrose, not following a concentration based trend.

Figure 13C:
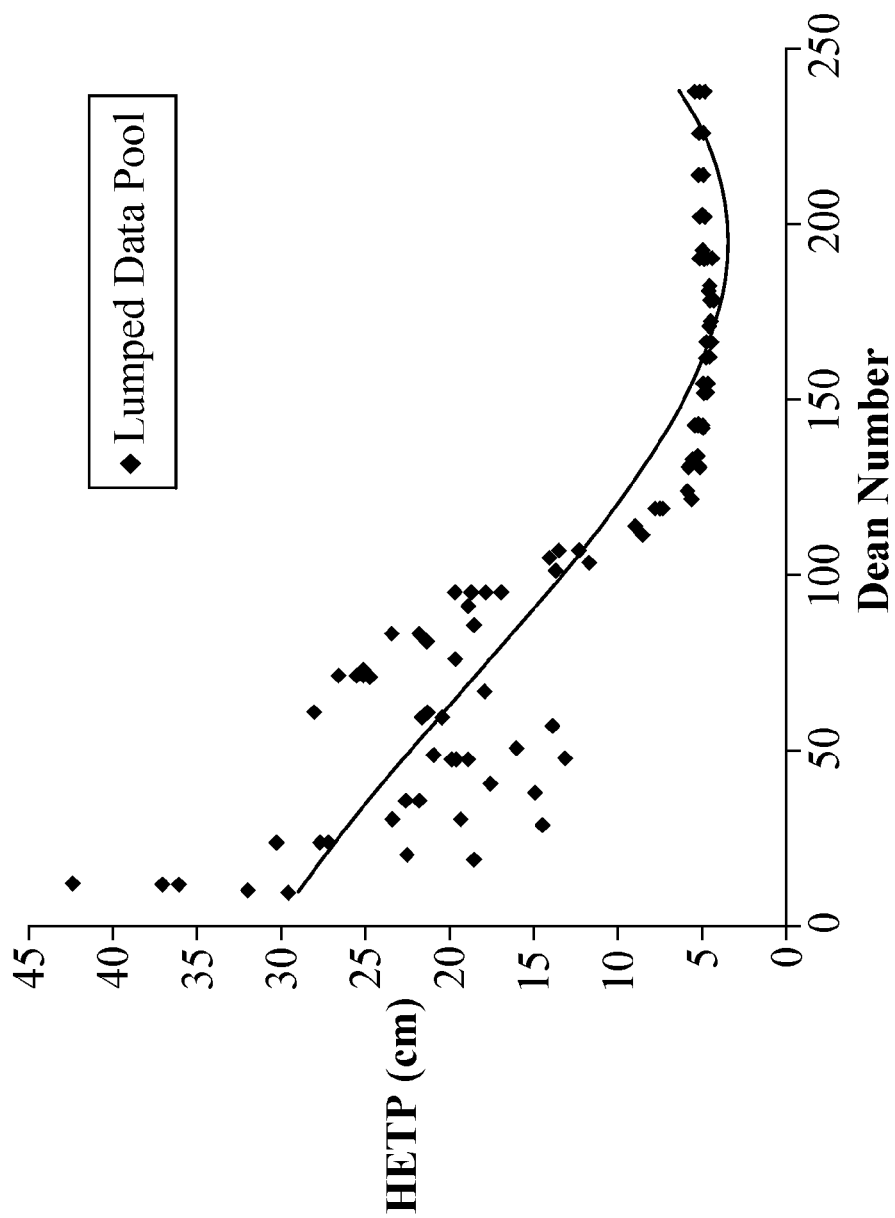
FIG. 13C is a graph illustrating the third order polynomial fit to a lumped dataset across all tested flow rates and viscosities, according to an example of the present disclosure.
Figure 13D:
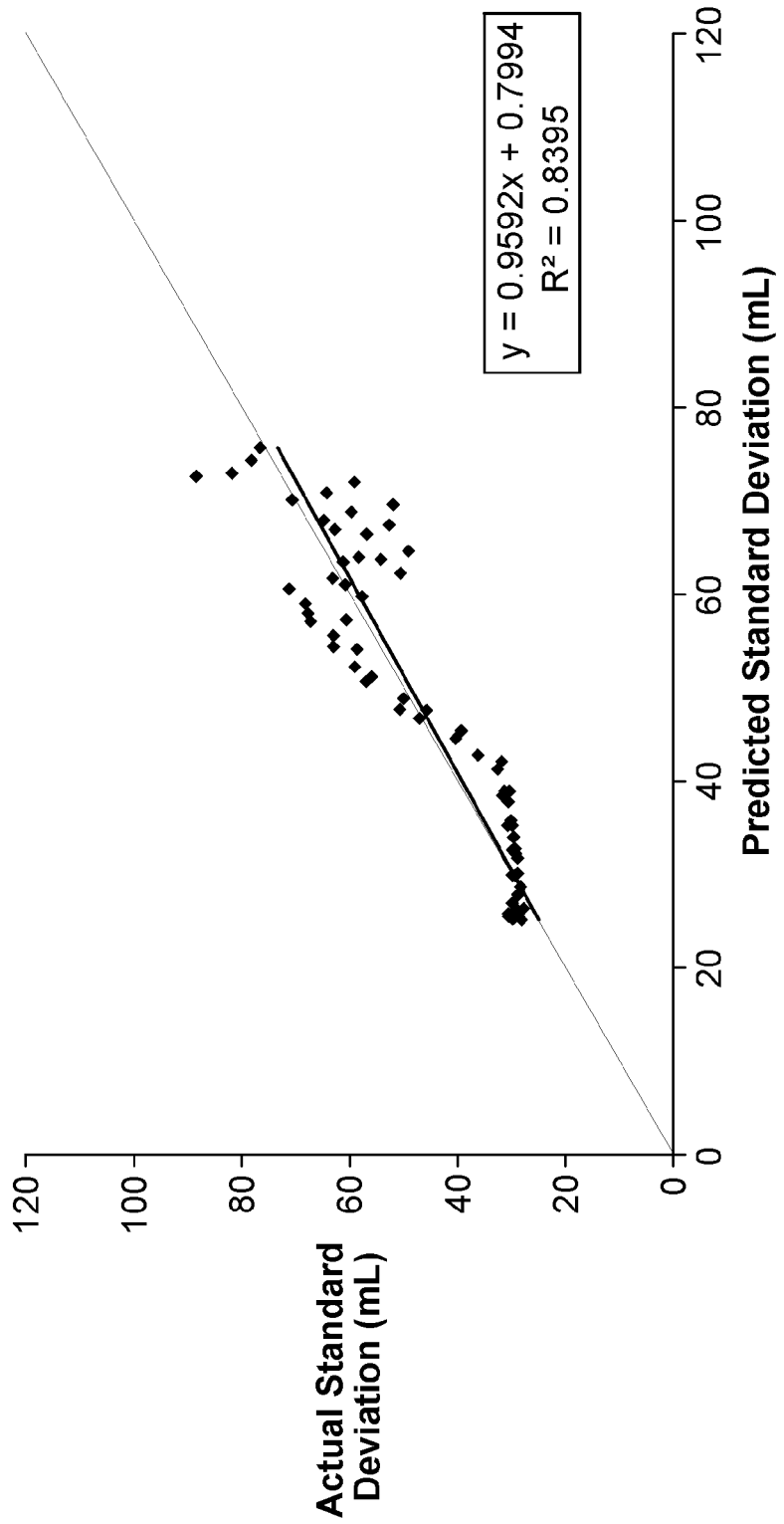
FIGS. 13D and 13E are the resulting parity plots of the lumped dataset for Standard Deviation and $T_{min}(5\sigma)$ respectively, according to an example of the present disclosure.
Figure 13E:
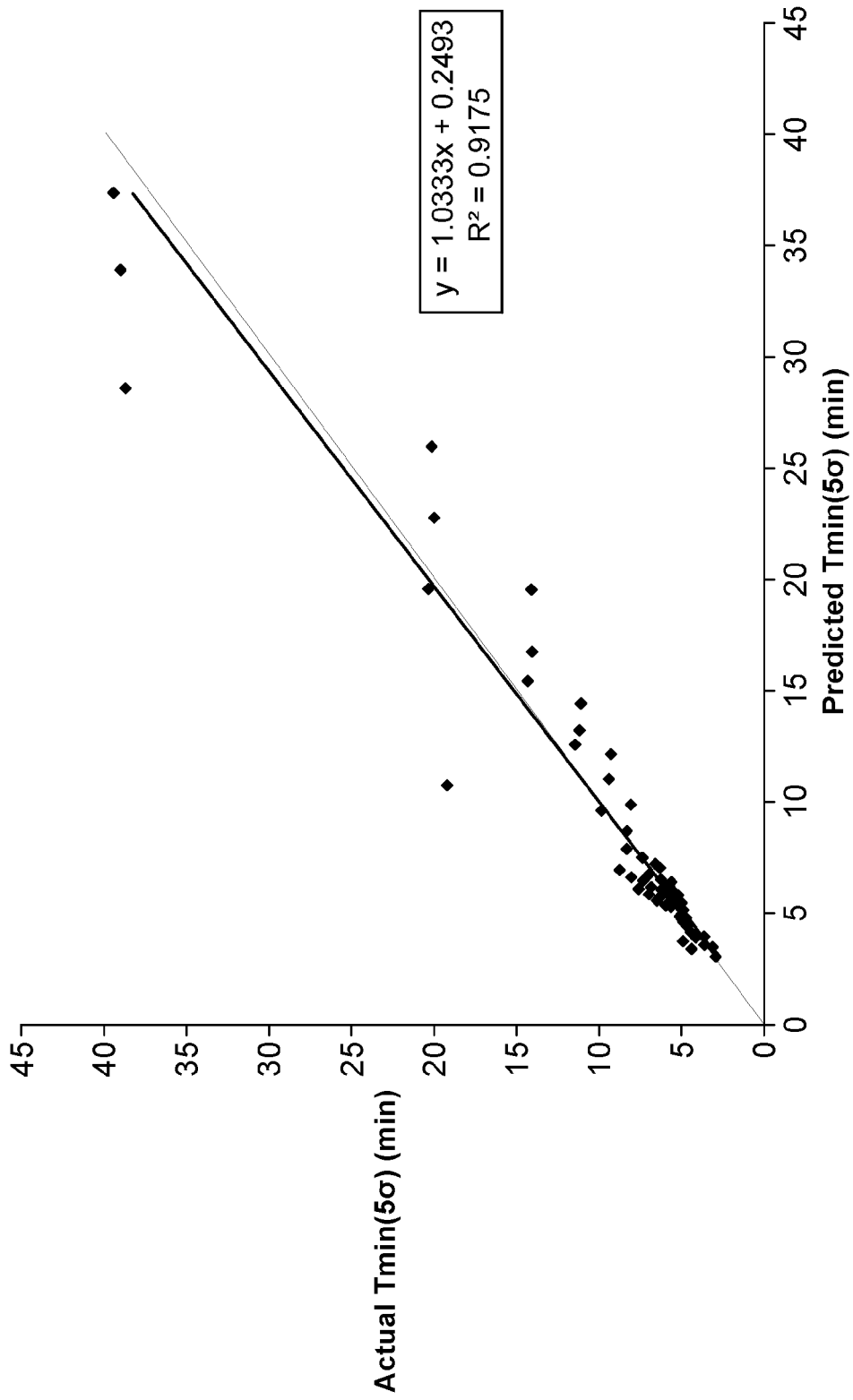

To inform the operation of the JIB, two prediction model approaches can be generated. The first uses a lumped data pool approach utilizing all of the experimental data from the various dextrose mobile phase experiments and normalizing the data to HETP and Dean Number (FIG. 13B). From this dataset, a $3^{rd}$ order polynomial can be fit to this data pool resulting in FIG. 13C and Equation 5 where a, b, c, and d are based on the polynomial fit. Equation 5 allows for the prediction of how wide a peak will become as a function of Dean Number. A parity plot can be generated for this model (FIG. 13D) which describes how well the model predicts the volumetric spreading of the pulse injection in the JIB. The fit has a relatively low $R^2$ value of 0.8405, which was expected due to a large amount of variability in the De<100 dataset. Using the Equations 2 and 6, an approximation can be made of when $T_{min}(5\sigma)$ (i.e. the time estimate in which the first detectable particle, such as a viral particle or a surrogate tracer exits the reactor) is expected to occur shown in FIG. 13E. The significance of the $T_{min}(5\sigma)$ will be explained later. The fit improves with an $R^2$ value of 0.9175, however, all data points below the y=x line represent scenarios where the model predicted a longer incubation than what actually occurred. Most of the error occurs at the larger $T_{min}$ time points which correspond to the lower Deans number experiments. This is a significant issue since the key unit operation specification is residence time.

$$HETP = aDe^3 + bDe^2 + cDe + d \quad (5)$$

Figure 14A:
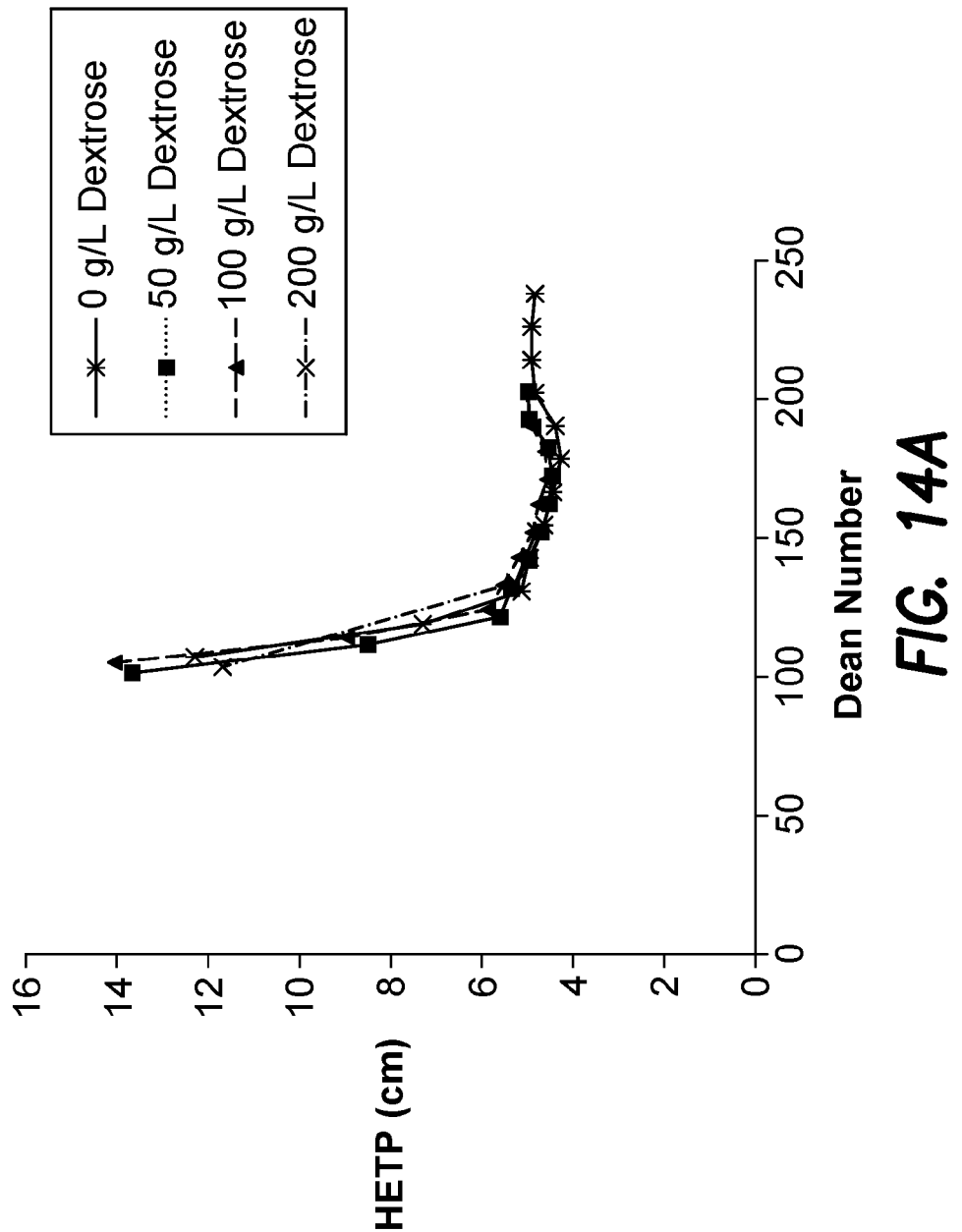
FIG. 14A is a graph illustrating the reaction of exiting pulse injection from variable flow rate and viscosity of JIB operation excluding the data point where De<100, according to an example of the present disclosure.
Figure 14B:
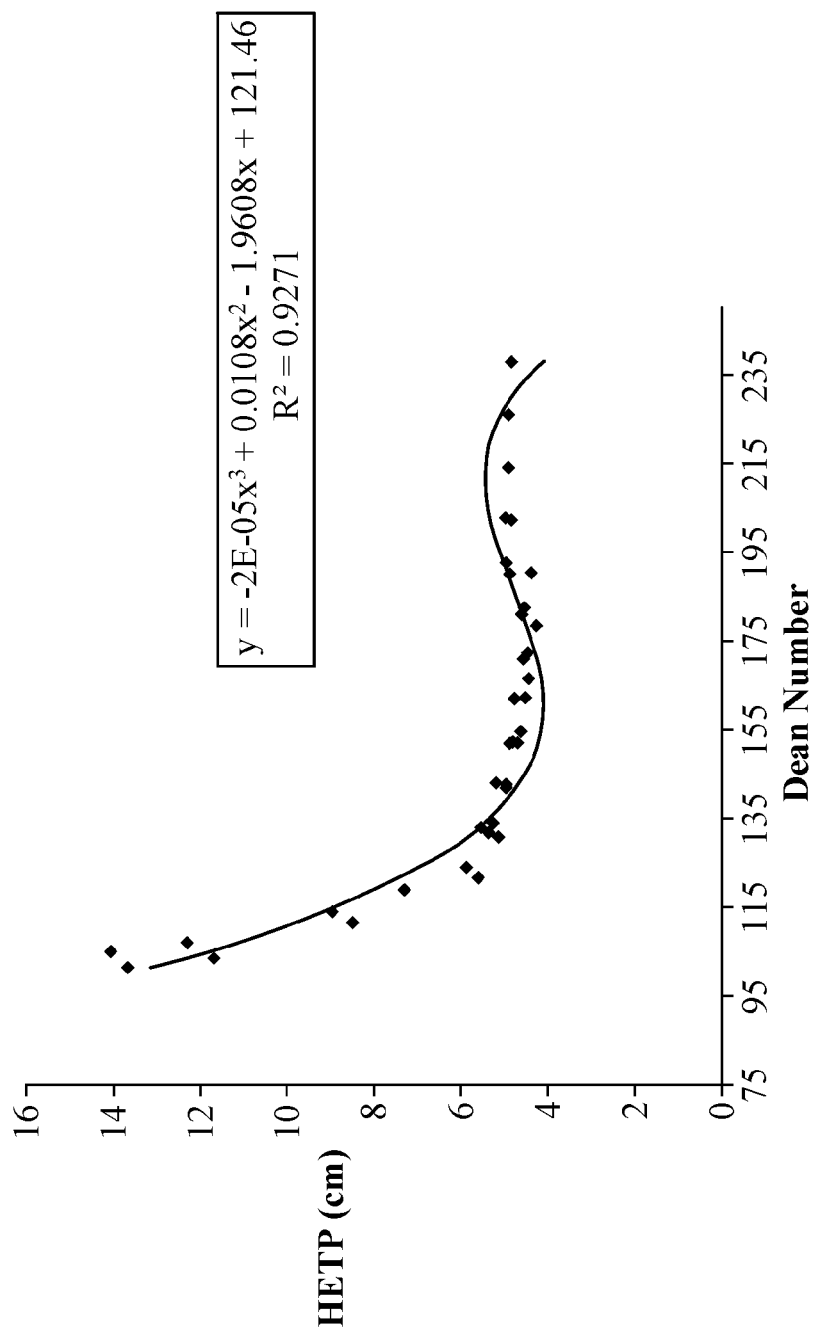
FIG. 14B is a graph illustrating the third order polynomial fit to a lumped dataset across all tested flow rates and viscosities excluding the data point where De<100, according to an example of the present disclosure.
Figure 14C:
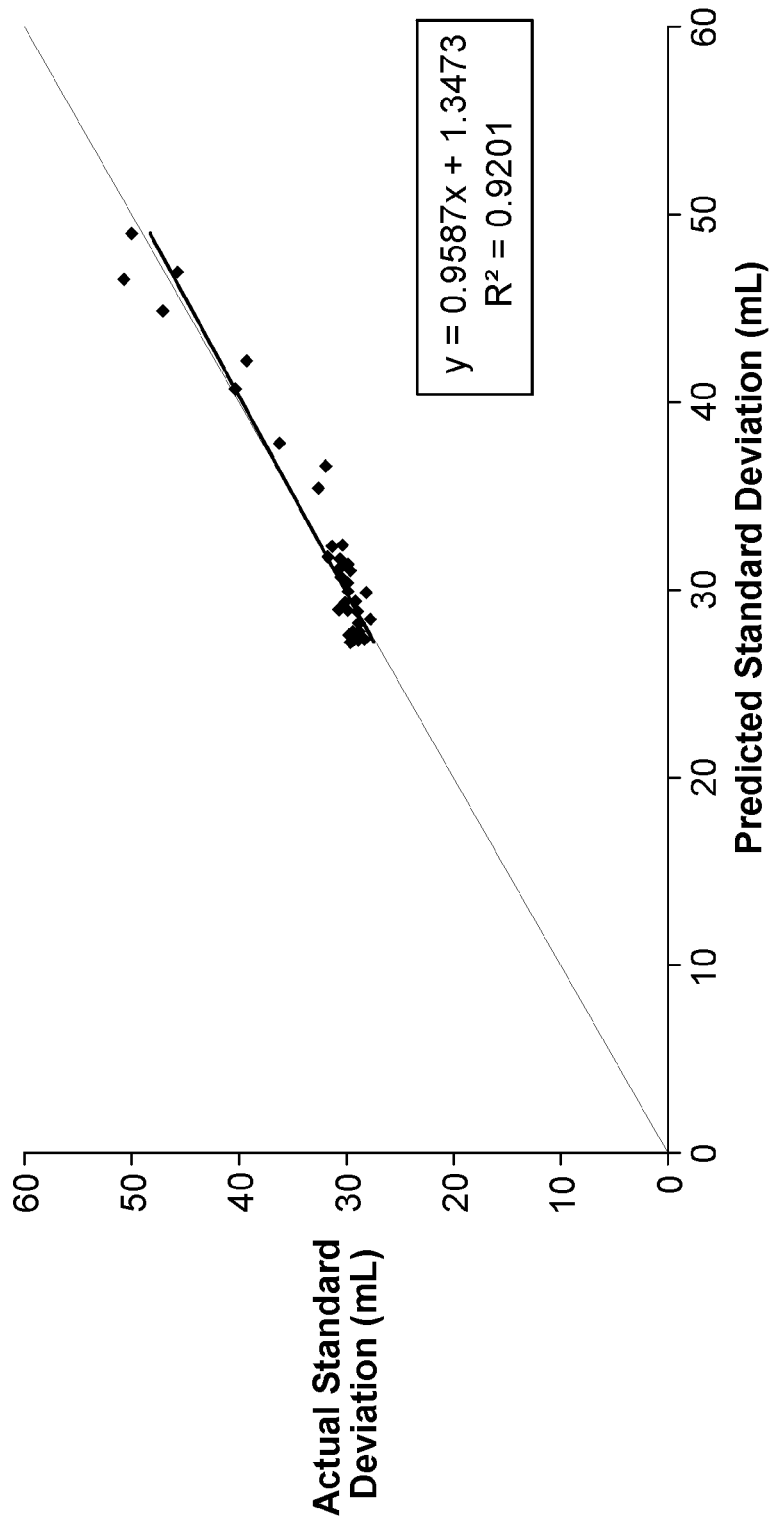
FIGS. 14C and 14D are the resulting parity plots of the lumped dataset, where data points where De<100 were excluded, for Standard Deviation and $T_{min}(5\sigma)$ respectively, according to an example of the present disclosure.
Figure 14D:
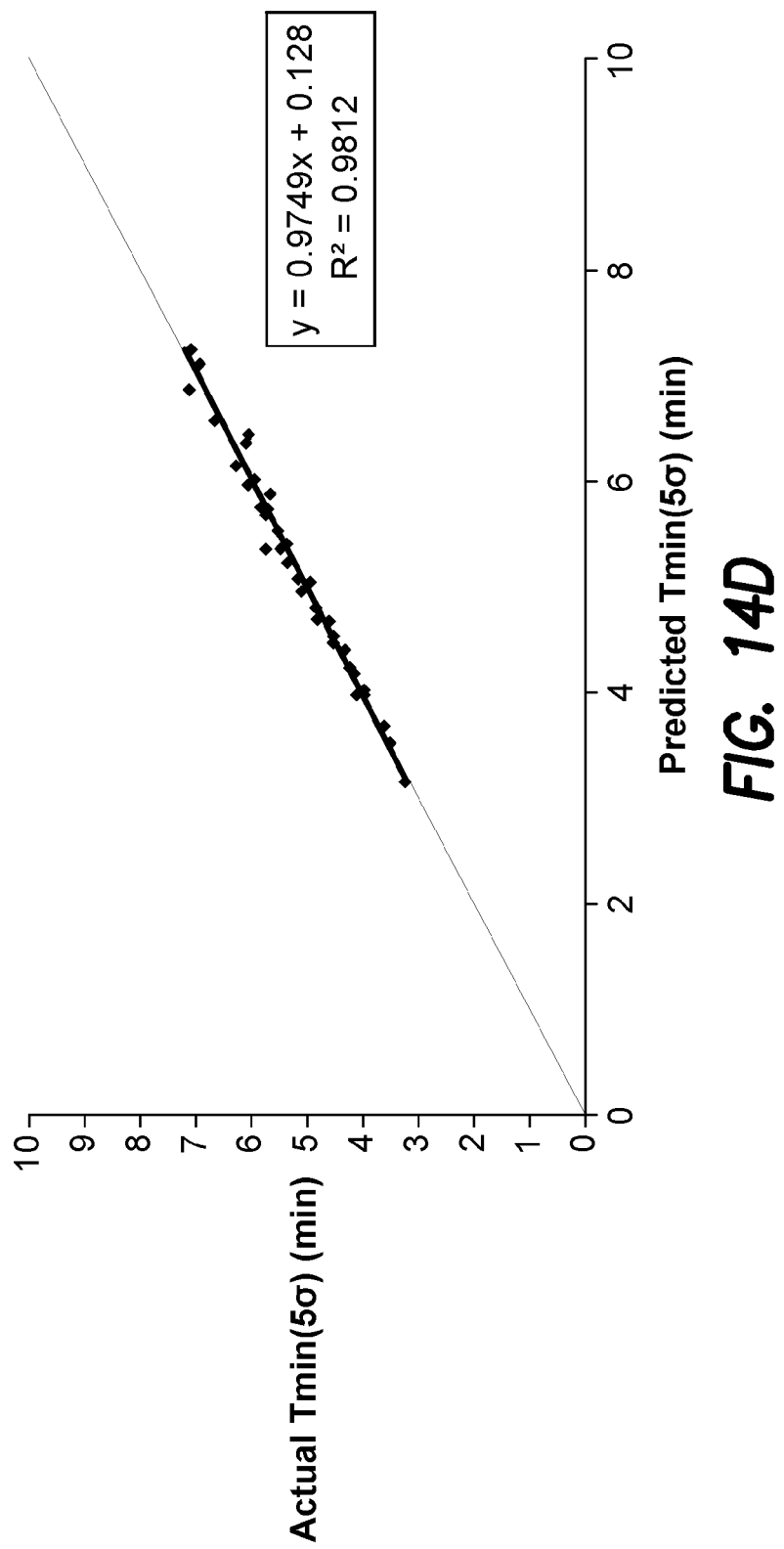

The second approach is applicable if a criterion of the JIB unit operation is to maintain a Dean Number of >100. When this condition is true, an exclusion criterion of only allowing data points collected at the De>100 set point are implemented into the model (FIG. 14A). This approach aims to reduce the noise in the model by removing the highly variable lower Dean number dataset. When this change is applied, the variability decreases which allows the spreading of the peak in the JIB to be predictable for variable viscosity and density fluids operated at different flow rates (FIG. 14B). FIG. 14C displays the parity plot of volumetric spreading of the pulse, and this second model approach has an increased $R^2$ value of 0.9201 compared to the lumped dataset approach. When the $T_{min}(5\sigma)$ is calculated and plotted (FIG. 14D) a better prediction model is generated with an $R^2$ value of 0.9812.

This model has two main applications to be used when determining the design and conditions of the JIB based CVI unit operation:

1. Given product stream requirements (i.e. $T_{min}$ and $T_{max}$), determine a length of a reactor and operational flow rates
2. Given the size of the reactor and operational flow rate, predict product stream outputs Starting with an understanding of the minimum residence time required for required viral inactivation and the maximum time the target molecule can be in the acidic condition before impacting product quality, Equations 6 and 7 can be applied to help determine the flow rate and path length required to meet those specifications.

$$T_{Ave} = T_{min} + (n^* \sigma_{time}) \quad (6)$$

$$T_{Ave} = T_{max} - (m^* \sigma_{time}) \quad (7)$$

$$T\min(2v) = \frac{T_{Ave}}{2} \quad (8)$$

Table 2A illustrated below outlines the quantitative aspect of the choice for the "n" and "m" value for $\sigma_{time}$.

TABLE 2A

Tangible Quantifications of the Standard Deviation Parameter Relating to Viral Clearance Risk Assessment
Viral Clearance Risk Assessment

| Time point | Time (min) | Quantity of pulse that has exited the reactor (%) |
|---|---|---|
| TAve | 78.8 | 50% |
| Tmin(2σ) | 71.8 | 2.275% |

TABLE 2A-continued

Tangible Quantifications of the Standard Deviation
Parameter Relating to Viral Clearance Risk Assessment
Viral Clearance Risk Assessment

| Time point | Time (min) | Quantity of pulse that has exited the reactor (%) |
|---|---|---|
| Tmin(3.5σ) | 66.5 | 0.023% |
| Tmin(5σ) | 61.2 | 0.00003% |
| Tmin(2v) | 39 | 0% |

Figure 15A:
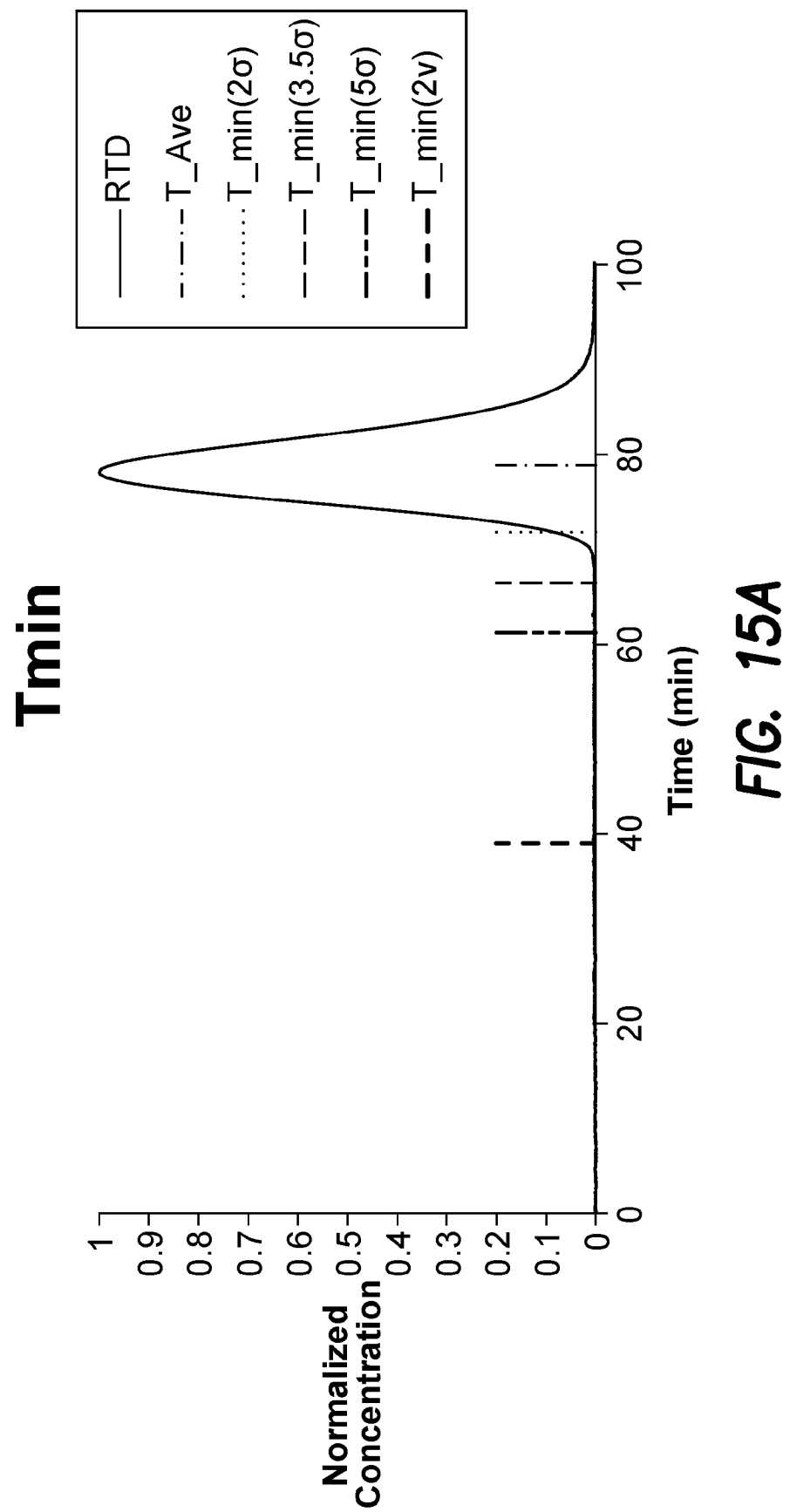
FIGS. 15A and 15B illustrate the Standard Deviation choices chosen from Tables 2A and Table 2B on an RTD profile, according to an example of the present disclosure.

FIG. 15A illustrates the resulting decisions on an RTD profile. The theoretical onset of the breakthrough of virus and target product starts with $T_{min}(2v)$ defined by Equation 8. This value is derived from Hagen and Poiseuille which states that for flow in a circular pipe, the fastest portion of the flow occurs in the geometric center of the cross-sectional area of the flow path and operates at two times the average velocity of flow. This is thought of as our "speed of light." A condition that it is close to impossible to reach in real-world practice due influencing mass transfer phenomenon (i.e. convection, diffusion, and Dean Vortices) and would require a highly specific and extreme set of conditions to attain operating in the JIB.

The exiting pulse injection is thought of as a Gaussian peak, and therefore its spread is thought of in terms of σ. For example, n=5 (i.e. $T_{min}(5\sigma)$) is understood to represent that 0.00003% of the product exited the reactor in-between $T_{min}(2v)$ and $T_{min}(5\sigma)$. This difference between $T_{min}(2v)$ and $T_{min}(5\sigma)$ can be visualized in FIG. 15A. This is considered to be a conservative ideology that overestimates the under incubated population. The intersection of $T_{min}(2v)$ and $T_{min}(5\sigma)$ are both derived estimation ideologies that ignore real-world possibilities. Where $T_{min}(2v)$ is the "speed of light" discussed above and there is no limit to the "n" value for $\sigma_{time}$. A large enough selected "n" value can calculate a $T_{min}$ to occur in negative time.

Figure 15B:
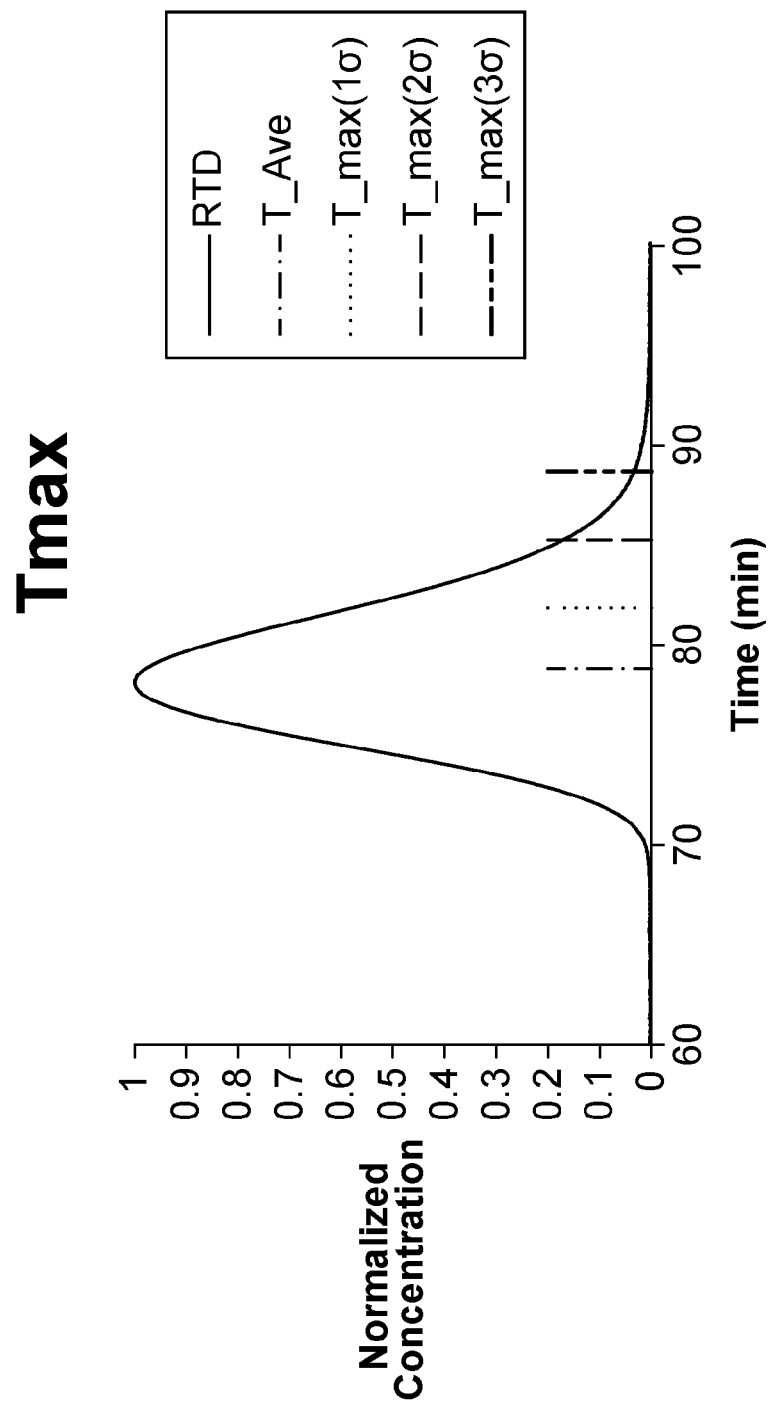

In a similar fashion, Table 2B and FIG. 15B correspond to a $T_{max}$ decision where m=3 (i.e. $T_{max}(3\sigma)$) would predict that ~99.865% of the product pool would exit the reactor less than or equal to $T_{max}$.

TABLE 2B

Tangible Quantifications of the Standard Deviation
Parameter Relating to Product Quality Risk Assessment
Product Quality Risk Assessment

| Time point | Time (min) | Quantity of pulse that has exited the reactor (%) |
|---|---|---|
| TAve | 78.8 | 50% |
| Tmax(1σ) | 81.9 | 84.134% |
| Tmax(2σ) | 85.3 | 97.725% |
| Tmax(3σ) | 88.7 | 99.865% |

This decision would be reliant on the product stability data or accepted yield loss in the presence of the acidic or any other viral inactivating condition. If we combine Equations 6 and 7 we get Equation 9.

$$T_{max} - T_{min} = \Delta T = (n+m) * \sigma_{time} \quad (9)$$

With a defined $T_{min}$ and $T_{max}$, a $T_{Ave}$ and $\sigma_{time}$ can be calculated. Using Equations 2, 3, and 5, multiple path lengths and flow rate combinations (i.e. starting with flow rates that yield a De>100) can be found to meet the specifications resulting in FIG. 5C. With calculated $T_{Ave}$ and $\sigma_{time}$ constrains, the minimum flow rate and minimum reactor volume can be calculated. This is an unadvisable location to operate as any increase or decrease in flow rate will result in residence times that are unbounded by $T_{min}$ or $T_{max}$. As the reactor volume increases, the volumetric flow rate increases as well to maintain the target $T_{max}$. When the flow rate increases, the efficiency of the JIB also increases. This allows more freedom in JIB operation displayed as error bars in FIG. 5C. In addition to the increasing efficacy, alteration of the operation window can be modulated by altering the n, m, $T_{min}$, or $T_{max}$ values of Equation 6 and 7.

Figure 16:
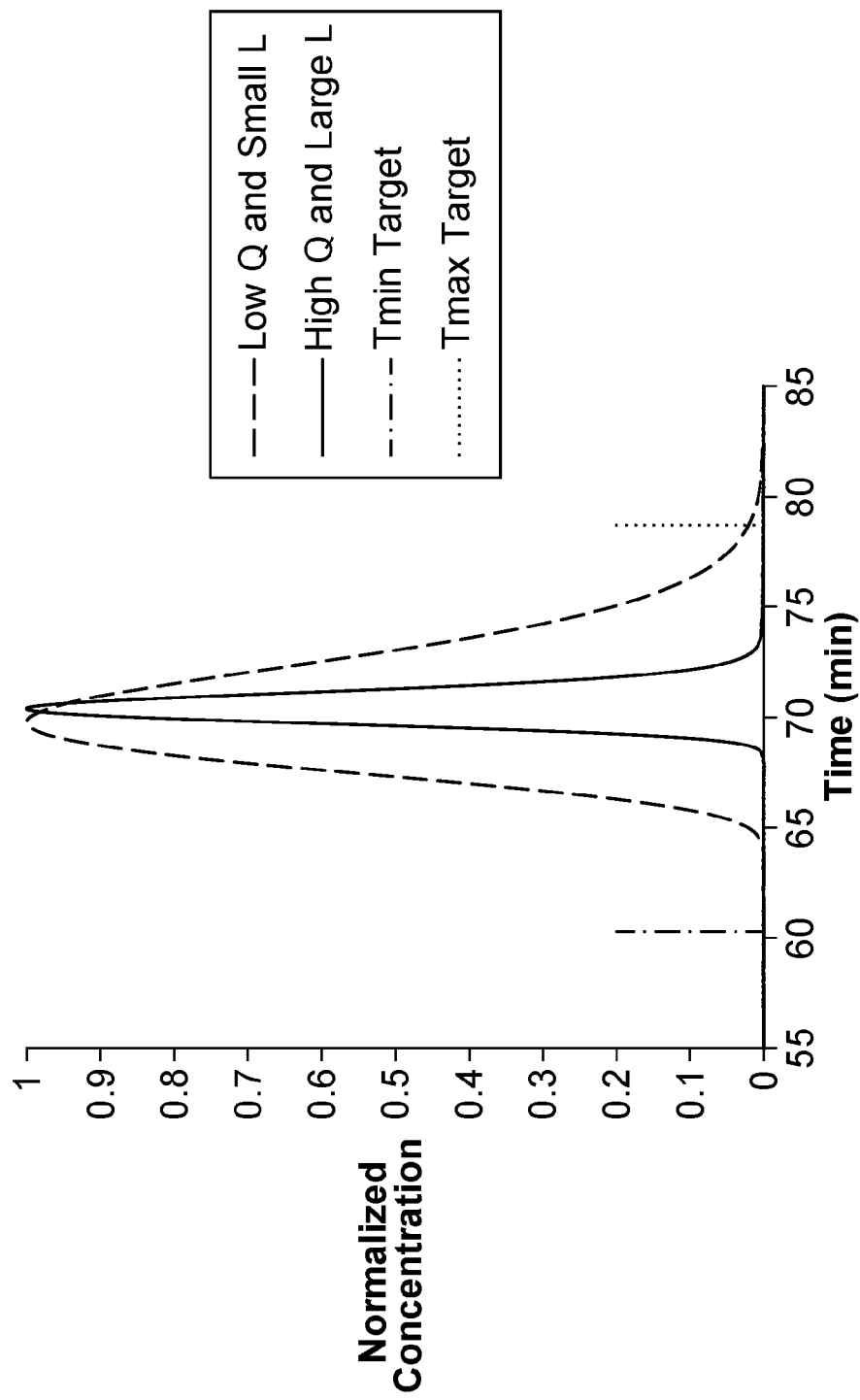
FIG. 16 illustrates two RTD profiles of varying combinations of path length and flow rate satisfying the arbitrary, but strict requirements of Tmin(5σ)>60 min and Tmax(3σ) <79 min, according to an example of the present disclosure.

To visualize this ideology and phenomenon, and given a process where the $T_{min}(5\sigma)$ and $T_{max}(3\sigma)$ are strictly defined at >60 min and <79 min respectively, FIG. 16 was generated. For the smaller reactor size operated at a slower flow rate, the $\sigma_{time}$ value is larger compared to the higher flow rate with a larger reactor size, visualized by the difference in width of the two peaks. Operating at the target flow rates, both designs obey the $T_{min}$ and $T_{max}$ constrains. With the increased sized reactor and corresponding faster flow rate, the $\sigma_{time}$ decreases allowing flexibility for deviations during operation.

When the CVI is implemented into real-world operation in a GMP setting, variable flow rates and viscosity are inevitable. With the work conducted in this experimental series, this variability can be addressed by understanding process operational extremes and corresponding worst-case conditions and predict how they propagate into the process outputs. Based on these isocratic viscosity experiments, it appears that the worst-case for viral incubation time is a high viscosity solution. Given that a chromatography elution peak's viscosity experiences one peak maximum, this should, therefore, be considered the worst-case. All other portions of the peak (i.e., the front and tail) will have lower viscosities relative to peak max, a larger Dean number, and therefore better mixing.

Figure 17A:
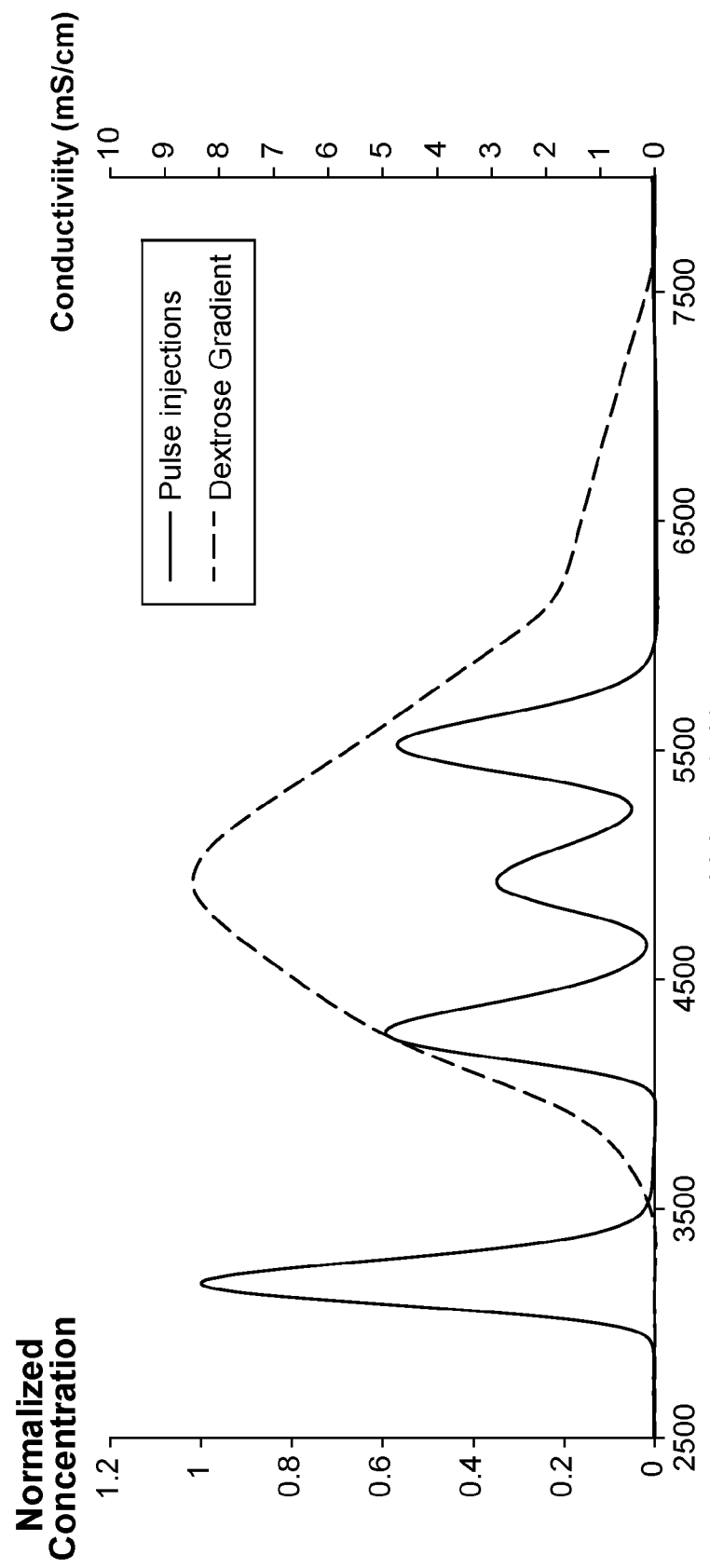
FIG. 17A illustrates the results of applying pulse injections into a simulated protein elution peak occurring before the addition of dextrose, the 2 peak mid-heights and the peak max, according to an example of the present disclosure.

To validate this claim, a mock protein peak was generated using dextrose to increase viscosity and NaCl to generate a conductivity trace. In the theoretical case of a protein A column, where the mAb will elute from the column in a Gaussian-like shape with some tailing. This general peak shape was generated used the gradient function of the Akta Avant 150, where the A1 line contained DI Water, A2 contained Riboflavin dissolved in water, and B1 Contained 200 g/L dextrose with approximately 150 mM NaCl. To evaluate the different viscosity gradient locations, four pulse injection locations were chosen with the first occurring before the addition of dextrose (0 g/L dextrose), the 2 peak mid-heights (50 g/L dextrose) and the peak max (100 g/L dextrose). FIG. 17A displays all four injections. To insert the peak without disturbing the density gradient, the A pump was switched from A1 to A2 while maintaining the gradient slope. This explains why the pulse injections are at different heights underneath the dextrose curve. Since the injections overlapped, the pulse injection locations were evaluated in their own experiment.

Figure 17B:
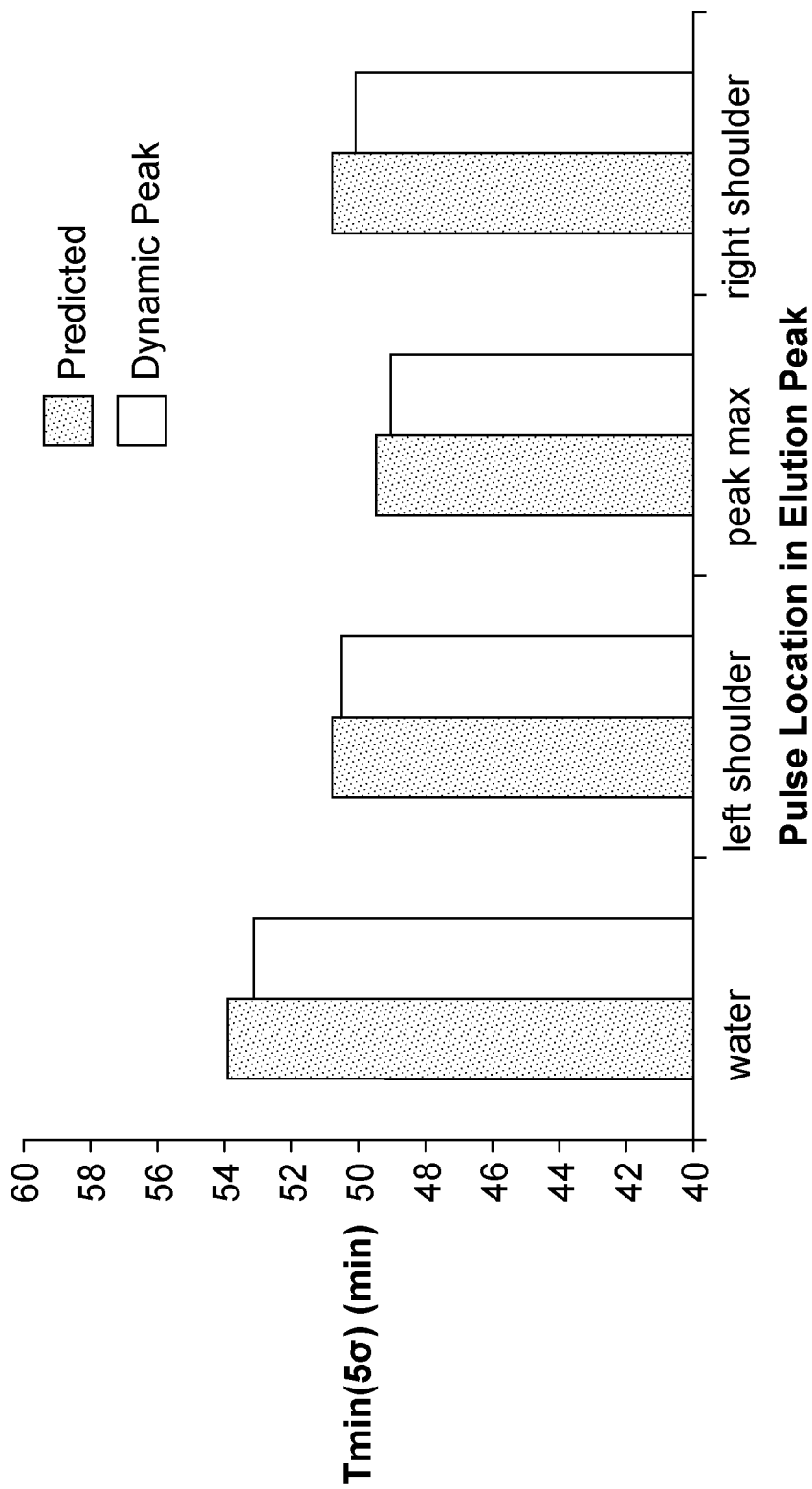
FIG. 17B is a comparison graph of predicted Tmin (5σ) based on the isocratic data versus the results from dynamic peak results, according to an example of the present disclosure.

The phenomena of peak spreading as a function of viscosity occurred in the dynamic composition setting. FIG. 17B shows how well the prediction model was at predicting Tmin(5σ). The difference between isocratic prediction and the dynamic experimental result was less than 1 minute, while the difference between the first water pulse injection and the pulse at peak max was approximately 4 minutes making it the worst-case for viral incubation.

Example 2

Mobile Phases and Flow Chamber:

The JIB was designed from previous development projects, which is described in the U.S. Pat. Ser. No. 62/742,534 (incorporated in its entirety by reference herein), and was 3D printed utilizing SLA Technology by 3D Systems (Rock Hill, SC). The riboflavin, Tris Buffer Saline (TSB), and dextrose used in creating the mobile phases were purchased through Thermo Fisher Scientific (Suwanee, GA). The viscosities of the solutions were determined by a microVISC S Viscometer utilizing an A05 Chip (San Ramon, CA). The densities of the solutions were determined by a calibrated pipette and a scale.

Bacteriophage Selection:

ΦX174 and the corresponding host bacteria $E.$ $Coli$ C were purchased from ATCC (ATCC Catalog #: 13706-B1 and 13706 respectively). The concentration of ΦX174 was quantified by utilizing standard plaque-forming assays, which entailed co-plating the fluid in question and the host bacteria $E.$ $Coli$ C with plating agar (i.e., Tryptic Soy Broth with 0.7% agarose) onto Tryptic Soy Agar plates. The bacteriophage ΦX174 was chosen as the appropriate tracer for this experiment due to some of its innate characteristics. ΦX174 is a relatively resilient bacteriophage where chances of loss in infectivity while suspended in an appropriate mobile phase conditions are low, but can also be easily sanitized with 0.1 M NaOH and a reasonable contact time. The surface characteristics of this bacteriophage are relatively inert compared to other viruses. Previous experience with this bacteriophage had shown significantly less surface adsorption relative to other viral models to both positively charged, hydrophobic, and multi-modal chromatography resins. Therefore, the probability of the virus non-specifically adsorbing in a slightly basic solution with a low ionic strength (i.e., pH 7.5 with 150 mM NaCl) to the 3D printed plastics was low. The plaque morphology of ΦX174 was also advantageous. ΦX174's plaque-forming units (pfu) create very large, bullseye type plaques that are easy to identify.

Preliminary Work

To determine the efficacy of the experimental protocol, a few preliminary experiments were conducted. First, pulse injections of ΦX174 were introduced into the JIB at the highest Dean number (i.e., high flow rate and low viscosity), which corresponds to the most chaotic flow stream due to Dean vortices. The discharge of the JIB was then collected and titered which was able to determine the mass balance of the injection. The result showed that recovered bacteriophage titer was within the typical error associated with a titering assay (i.e., (+/−) 0.5 logs). Sampling the dead volume remaining in the outlet valve, ~300 pfu/mL persisted. A sanitization program was then created to thoroughly sanitize the injection valve, JIB, and outlet valve with 0.1 M NaOH with a contact time of ≥15 min. After the sanitization cycle, no infectious particle remained in the outlet lines.

Determining Minimum Residence Time (ΦX174):

A 0.32 and 0.64 cm i.d. 3D printed JIB's were tested using an Akta Explorer 100 by GE Healthcare (Uppsala, Sweden). To prepare for the experiment, a 30 mL aliquot of the mobile phase was taken and set aside for spiking. The aliquot was then spiked at 0.06% (v/v) targeting a mobile phase concentration of $10^{6.5}$ pfu/mL. The spike was purposely spiked at a considerably low level to ensure the fluid properties of the experimental injection were not changed by the ΦX174 spike. Using a syringe, 25 mL of spiked sample was then loaded into a 50 mL capacity Superloop by GE Healthcare (Uppsala, Sweden) while the remaining sample was held on the bench as a holding sample to determine if significant ΦX174 death occurred as a function of mobile phase condition independent of flowing through the JIB. ΦX174 never experienced an off-target mobile phase concentration within the typical error of a titering assay (i.e., (+/−) 0.5 logs). Finally, the empty fraction collection containers were then weighted to determine the tare weight.

To start the experiment, the Akta began pushing mobile phase through the injection valve, in the "Inject" position, into the Superloop to introduce the ΦX174 spiked buffer into the JIB for 3% of the total reactor volume, with the discharge of the flow directed into a large volume container. The injection valve then switched to "Load" position to stop flow of mobile phase through the Superloop and redirected to go directly to the JIB to flush out the injection with the discharge remaining in the same large volume container. After a predetermined amount of time, the outlet valve switched to direct flow from the large volume container to a small volume container. The outlet valve subsequently switched two more times creating two more fractions. The time and volume of the three small and one large fractions were determined by Tmin 3, 4, and 5σ using the modified peak analysis. The outlet flow path for the three small volume fractions were 1 mm capillary PEEK tubing by GE Healthcare (Uppsala, Sweden). When the experiment was completed, the three small and one large container were then weighed. To sample for virus, the dead volume of the capillary tube was then drained in sterile tubes for a sample volume of ~100 uL. The sample left behind in the capillary tube would have been the last drop of that fraction and can be thought of as an instantaneous grab sample. The entire volume of this grab sample was then titered without dilution; therefore, the issue of "probability of detection of viruses at low concentrations" outlined in ICH Q5A does not apply.

After all post Akta experiment activities were completed, the remaining spiked mobile phase was expelled from Superloop, and the Superloop was taken offline. The injection loop position was then replaced with PEEK capillary tubing and the sanitization step outlined above was completed, and then subsequently quenched with TSB.

Results

Figure 18:
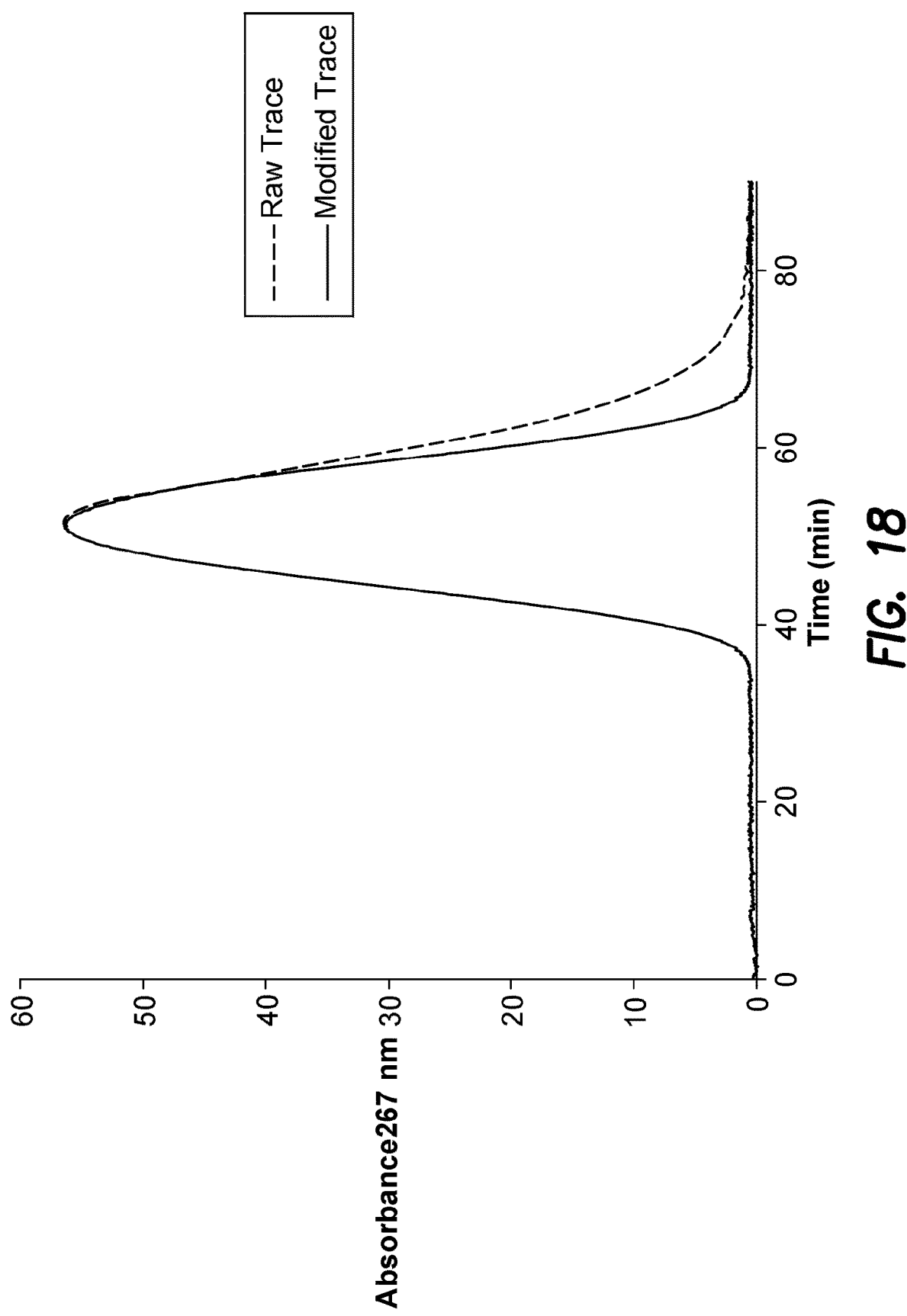
FIG. 18 is a comparison graph of the peak generated from the pulse injection and a modified peak, according to an example of the present disclosure.
Figure 19:
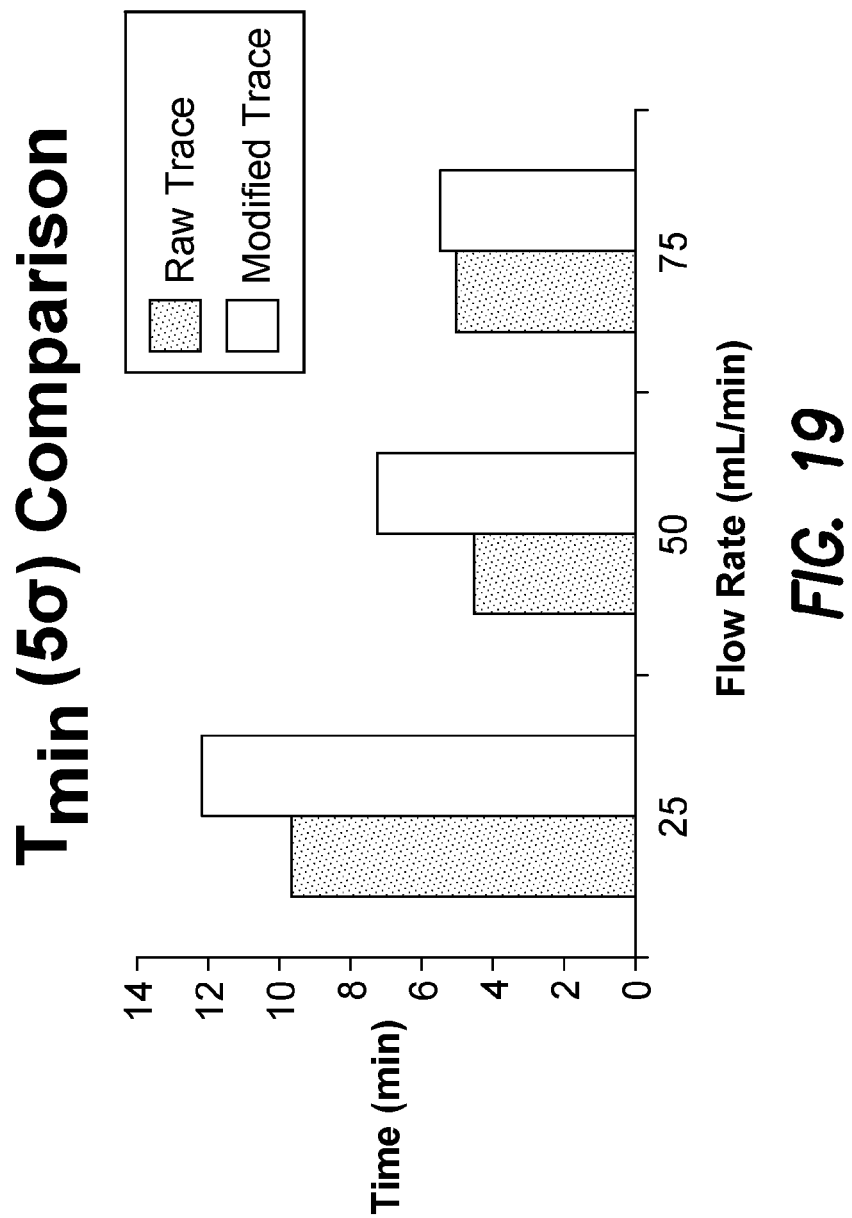
FIG. 19 is a comparison graph of the calculation of time (5σ) from the raw and modified traces, according to an example of the present disclosure.

Through preliminary results with the bacteriophage, it was found that the calculation model discussed above provided a very conservative estimate of the minimal residence time (Tmin). To account for this, the raw peaks were modified. FIG. 18 displays a comparison of the peak generated from the detector of the Akta as the dye pulse injection (i.e., Raw Trace, dashed line) exits the JIB and a modified peak (i.e., Modified Trace, solid line). The Modified Trace was created by determining the peak's maximum absorbance and mirroring the left side trace to the right side of the peak maximum. FIG. 19 displays the calculated Tmin(5σ) as a function of the original Raw Trace versus the Modified Version.

Figure 20:
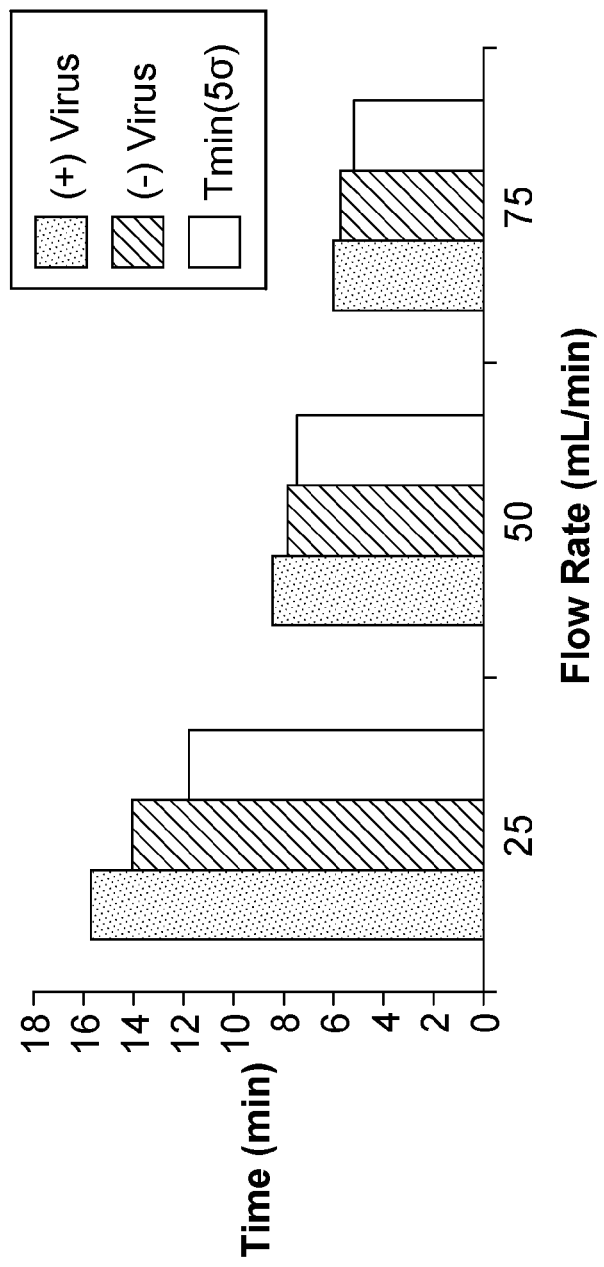
FIG. 20 is a comparison graph of the low viscosity bacteriophage pulse injection experiments where (+) Virus represents the first time point to test positive for virus and (−) Virus represents the last time point to test negative for virus.
Figure 21:
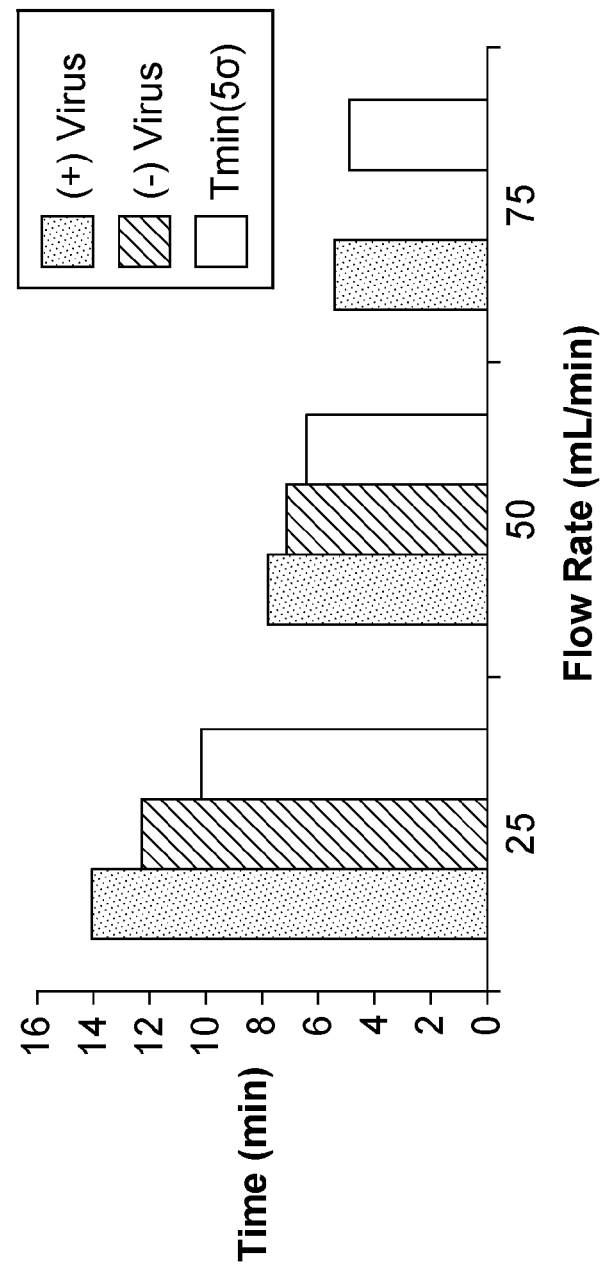
FIG. 21 is a comparison graph of the high viscosity bacteriophage pulse injection experiments where (+) Virus represents the first time point to test positive for virus and (−) Virus represents the last time point to test negative for virus.
Figure 22:
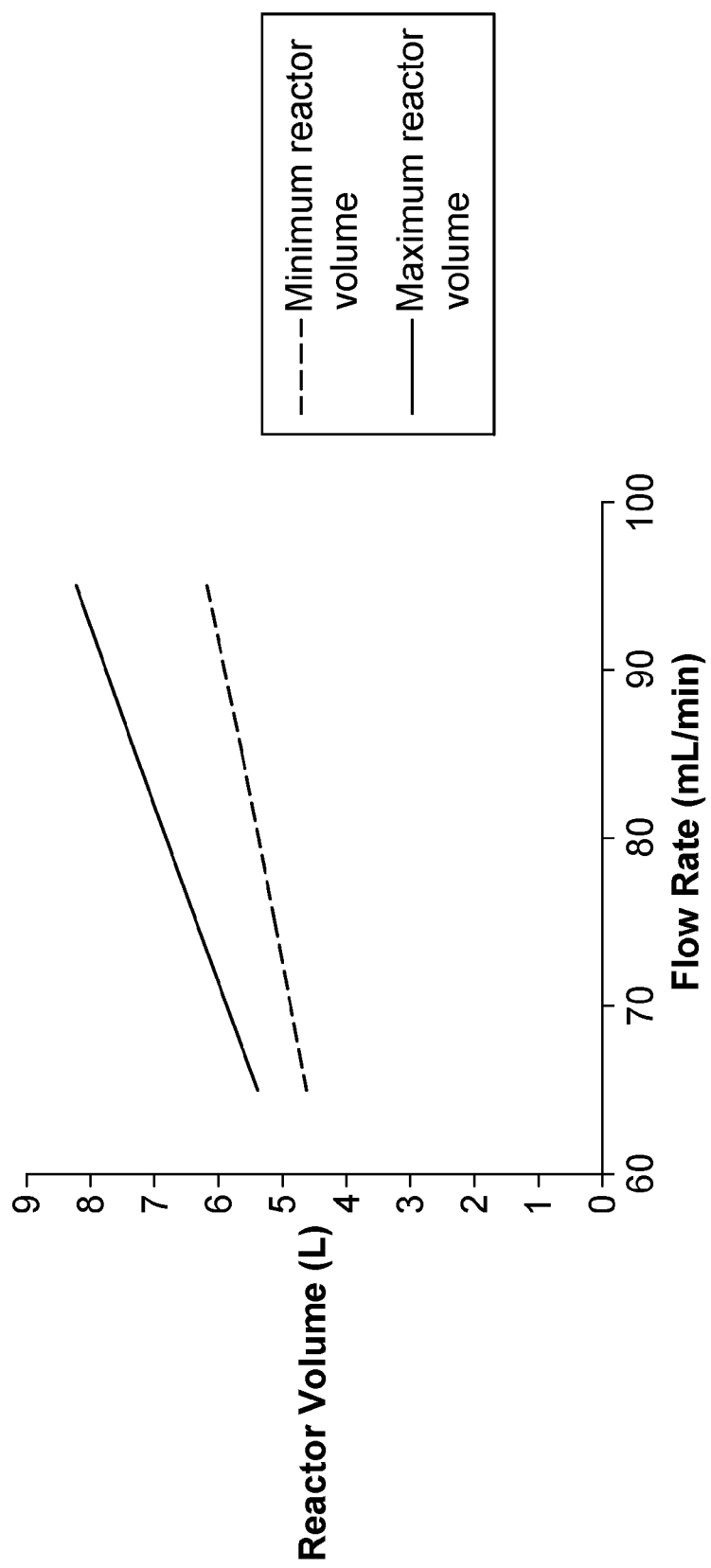
FIG. 22 is a graph illustrating the relationship between the reactor volume and the flow rate of the actual reactor, according to an example of the present disclosure.

FIG. 20 displays the results of the low viscosity bacteriophage experiments that utilized TSB as the mobile phase. The sampling strategy for these experiments sought to collect an instantaneous grab sample at the discharge of the JIB at Tmin 3, 4, and 5σ. For the three flow rates tested 4σ and 5σ tested negative for virus, while 3σ tested positive for virus. It is known from the equations that increasing the viscosity decreases the JIB efficiency. Since 4σ and 5σ were negative for virus for the low viscosity, the same volumetric sampling strategy was utilized assuming this would be enough volumetric space to capture the reduced efficacy. When the viscosity is increased by the addition of dextrose, the breakthrough of virus occurred sooner for the higher viscosity. However, as shown in FIG. 21, the 75 mL/min data point lacks a (−) virus result. This is due to the sampling strategy, not the efficacy of the reactor or the calculations.

Example 3

Determining Parameters to Scale a Reactor 5×

In an example, a user, using the reactor in FIG. 1C, can calculate the number of devices connected in series (e.g. as shown in FIG. 1D) to provide the target residence time distribution for a process. In addition, a user can leverage the work completed to calculate the dimensions of a larger scale reactor. In this experiment the inner diameter (i.d.) of the flow path and the radius of curvature of the reactor shown in FIG. 1C in the system shown in FIG. 2A were determined. The i.d. of the flow path in the reactor in FIG. 1C was determined to be 0.635 cm and radius of curvature was 0.6825 cm in the system shown in FIG. 2A. To obtain these parameters, a tracer was pulse injected into the reactor shown in FIG. 1C and was flushed out at various flow rates. The results of each of these experiments are shown in FIGS. 2B-C. Once the pulse injection experiments were completed, the resulting peaks were analyzed by fitting a Gaussian curve to the discharging peaks as shown in FIG. 2D and a subsequently $\rho^2_{Time}$ was calculated by the fit. The $\sigma^2_{Time}$ value was then converted to HETP (using Equation 1, below) as shown in FIG. 2E, and plotted against the Dean number (using Equation 2, below)

$$HETP = \frac{\sigma^2_{time} * L}{T^2_{Ave}} \tag{1}$$

$$De = \left(\frac{\rho u D}{\mu}\right) * \sqrt{\frac{D}{2R_c}} \tag{2}$$

A best-fit line was applied to the dataset shown in FIG. 2E and expressed in Equation 3, below.

$$HETP = f(De) = (aDe^3 + bDe^2 + cDe + d), \tag{3}$$

wherein a, b, c, and d are based on empirical data fits for all Dean numbers. Equation 1 and 3 were then combined and rearranged to create Equation 4, below.

$$\sigma_{time} = \sqrt{\frac{(aDe^3 + bDe^2 + cDe + d) * T^2_{Ave}}{L}} \tag{4}$$

It is required that 99.99997% of the product remain within the reactor for ≥60 minutes (i.e., $T_{min}$), which makes n=5 (in Equation 5, below). Additionally, it is required that 99.865% of the product exit the reactor for ≤90 minutes (i.e. $T_{max}$), which makes m=3 (in Equation 6, below). The maximum kinematic viscosity allowable within the reactor was $1.5*10^{-6}$ $m^2/s$. Based off this viscosity and the reactor dimensions mentioned previously, to satisfy the requirement of Dean number≥100, the flow rate within the reactor must be ≥65 mL/min and due to arbitrary process constraints, the flow rate must be ≤95 mL/min $$T_{Ave} = T_{min} + (n^*\sigma_{max}), \text{ wherein } n \text{ can be 5 and } T_{min} \text{ can be 60 min} \tag{5}$$

$$T_{Ave} = T_{max} - (m^*(\sigma_{max})), \text{ wherein } m \text{ can be 3 and } T_{max} \text{ can be 90 min} \tag{6}$$

From the above constraints, a locus of solutions can be generated to satisfy the constraints. As seen in the table below, four flow rates were solved. The target flow rate, reactor design (i.e., i.d. of the flow path and the radius of curvature), and maximum kinematic viscosity calculate worst-case Dean number. The outputted Dean number was then entered into Equation 3 and that value was inputted into Equation 4. Through a guess and check method, different reactor volumes were cast through a stepwise cascade of equations. A proposed reactor volume was then divided by flow rate to calculate average residence time (see Equation 7, below) and divided by the cross-sectional area of the internal diameter of the flow path to obtain the path length. The path length and average residence time were also inputted into Equation 4 to get a $\sigma_{time}$ value. Equations 5 and 6 were then used to find the $T_{min}$ and $T_{max}$.

$$T_{Ave} = \frac{\text{Reactor Volume}}{\text{Flow Rate}} = \frac{\text{Linear flow velocity}}{\text{Path Length}} \tag{7}$$

Table 1 displays the maximum and minimum reactor volume solutions for each flow rate as a function of a $T_{min}$ of 60 min or a $T_{max}$ of 90 min. These reactor specifications are displayed in FIG. 22 and are similar to FIG. 5C. Any flow rate and reactor volume chosen between those two lines will satisfy the target residence time distribution selected (i.e. $T_{min}$ and $T_{max}$). The difference between FIG. 22 and FIG. 5C is the viscosity term used in the two figures. The higher viscosity of FIG. 22 reduces the efficacy of the reactor and lends itself to faster flow rates and higher volume reactor. Table 2 displays the decision of reactor operation specification. The flow rate chosen was selected relatively arbitrary with the desire to keep the flow rate low. With the selection of a flow rate, the reactor volume was selected for being the mid-point between the maximum and minimum reactor volume.

TABLE 1

Maximum and Minimum Reactor Volume Solutions for each Flow Rate as a Function of a $T_{min}$ of 60 min or a $T_{max}$ of 90 min

| Flow Rate (mL/min) | Dean number | HETP (cm) | Volume (L) | $T_{Ave}$ (min) | $\sigma_{time}$ (min) | $T_{min}(5\sigma)$ (min) | $T_{max}(3\sigma)$ (min) |
|---|---|---|---|---|---|---|---|
| 65 | 98.77 | 14.31 | 4.62 | 71.13 | 2.23 | 60.00 | 77.82 |
| | 98.77 | 14.31 | 5.38 | 82.79 | 2.40 | 70.78 | 90.00 |
| 75 | 113.97 | 9.33 | 5.11 | 68.19 | 1.64 | 60.00 | 73.11 |
| | 113.97 | 9.33 | 6.34 | 84.52 | 1.82 | 75.40 | 90.00 |
| 85 | 129.16 | 6.25 | 5.63 | 66.21 | 1.24 | 60.00 | 69.93 |

TABLE 1-continued

Maximum and Minimum Reactor Volume Solutions for each Flow Rate as a Function of a $T_{min}$ of 60 min or a $T_{max}$ of 90 min

| Flow Rate (mL/min) | Dean number | HETP (cm) | Volume (L) | $T_{Ave}$ (min) | $\sigma_{time}$ (min) | $T_{min}(5\sigma)$ (min) | $T_{max}(3\sigma)$ (min) |
|---|---|---|---|---|---|---|---|
|  | 129.16 | 6.25 | 7.29 | 85.76 | 1.41 | 78.69 | 90.00 |
| 95 | 144.36 | 4.65 | 6.18 | 65.02 | 1.00 | 60.00 | 68.04 |
|  | 144.36 | 4.65 | 8.22 | 86.52 | 1.16 | 80.73 | 90.00 |

TABLE 2 decision of reactor operation specification

| Flow Rate (mL/min) | Dean number | HETP (cm) | Volume (L) | $T_{Ave}$ (min) | $\sigma_{time}$ (min) | $T_{min}(5\sigma)$ (min) | $T_{max}(3\sigma)$ (min) |
|---|---|---|---|---|---|---|---|
| 70 | 106.37 | 11.56 | 5.33 | 76.13 | 2 | 66.15 | 82.12 |

Additionally, the reactor design specifications in terms of internal diameter, a radius of curvature, flow rate, and path length were determined to satisfy a large scale operation. In this example, the user required the dimensions to operate at 5× the process volumetric flow rate (i.e. 350 mL/min) and also desired to keep the ratio between the internal diameter and radius of curvature to be constant. The dataset shown in FIG. 2E was divided by the internal diameter of the reactor used to generate the dataset (i.e., 0.635 cm) resulting in a figure similar to FIG. 10C. A best-fit line was then applied to the dataset. Table 3 displays the known and unknowns for the new reactor's specifics. With a target flow rate and a $T_{Ave}$ from Table 2, reactor volume can be calculated from Equation 7. From the above constraints, a locus of solutions was generated to satisfy constraints. As seen in Table 4 below divided by the reactor volume returned the path length of the reactor. The outputted Dean number was then entered into Equation 8, below, and multiplied by the internal diameter to return the HETP. The path length and average residence time were also inputted into Equation 4 to get a $\sigma_{time}$ value. Equations 5 and 6 were then used to find the $T_{min}$ and $T_{max}$. As the internal diameter increases the Dean number decreases which subsequently decreases reactor efficiency. Any internal diameter chosen between 1.5-1.7 cm will provide the appropriate residence time distribution.

$$\frac{HETP}{D} = h = (aDe^3 + bDe^2 + cDe + d) \qquad (8)$$

TABLE 3

Known and Unknowns for the New Reactor's Specifics

| Flow Rate (mL/min) | Dean number | HETP (cm) | Volume (L) | $T_{Ave}$ (min) | $\sigma_{time}$ (min) | $T_{min}(5\sigma)$ (min) | $T_{max}(3\sigma)$ (min) |
|---|---|---|---|---|---|---|---|
| 350 | ? | ? | ~26.64 | 76.13 | ? | ? | ? |

TABLE 4

Derived Internal Diameters

Figure 23:
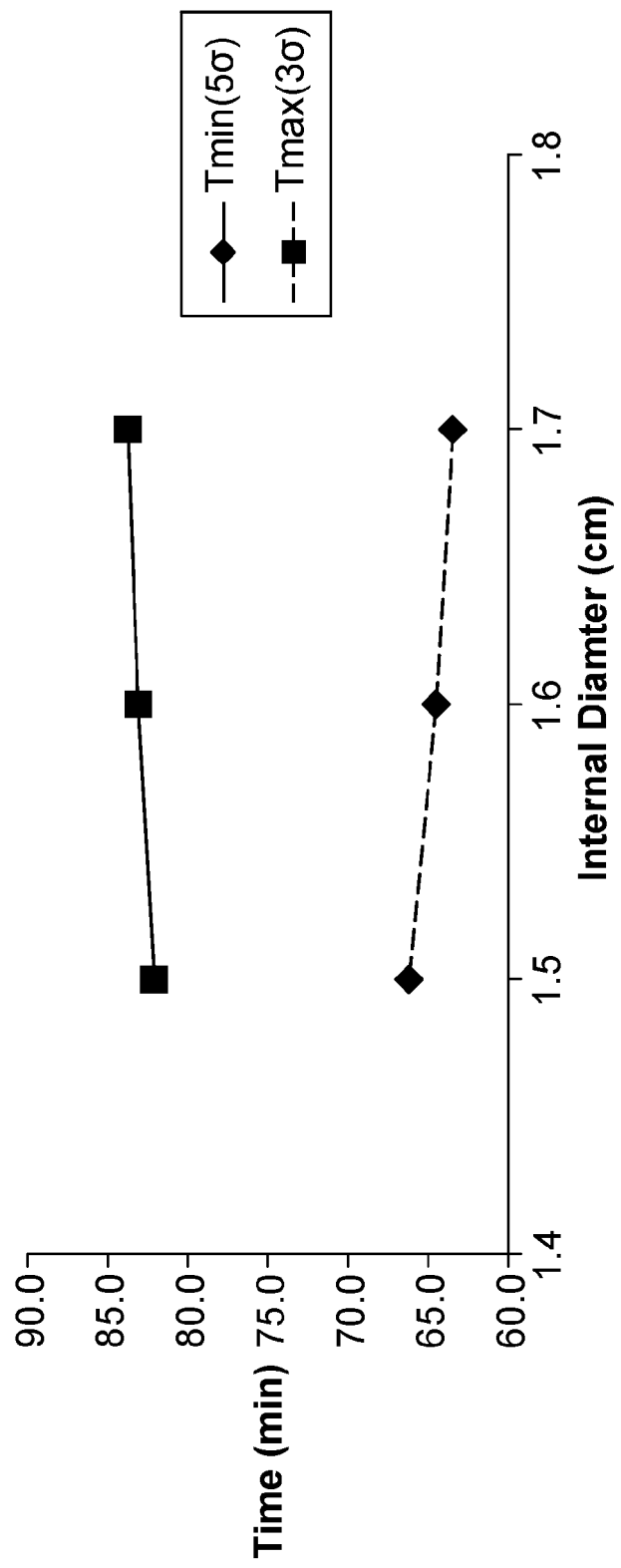
FIG. 23 is a graph illustrating solutions for the internal diameter of scale up.

| Flow Rate (mL/min) | Internal Diameter (cm) | Dean number | Estimated HETP (cm) | Volume (L) | $T_{Ave}$ (min) | Estimated $\sigma_{time}$ (min) | Estimated $T_{min}(5\sigma)$ (min) | Estimated $T_{max}(3\sigma)$ (min) |
|---|---|---|---|---|---|---|---|---|
| 350 | 1.5 | 225 | 10.3 | 26.64 | 76.13 | 2.0 | 66.2 | 82.1 |
|  | 1.6 | 211 | 12.4 | 26.64 | 76.13 | 2.3 | 64.5 | 83.1 |
|  | 1.7 | 198 | 13.0 | 26.64 | 76.13 | 2.5 | 63.4 | 83.7 | and plotted in FIG. 23, three internal diameters are solved for. Any internal diameter selected along this plotted line will be able to supply the proper residence time distribution. Final selection of an internal diameter will be decided on a basis of a compromise of residence time distribution and pressure drop in the reactor where the smaller the internal diameter and longer path length will increase the pressure. The fixed flow rate and average residence time fixed the reactor volume (Equation 7). The variable internal diameter From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The scope of this disclosure is to be broadly construed. It is intended that this disclosure disclose equivalents, means, systems, and methods to achieve the devices, activities and mechanical actions disclosed herein. For each device, article, method, mean, mechanical element or mechanism disclosed, it is intended that this disclosure also encompass in its disclosure and teaches equivalents, means, systems, and methods for practicing the many aspects, mechanisms and devices disclosed herein. Additionally, this disclosure regards a coating and its many aspects, features, and elements. Such a device can be dynamic in its use and operation, this disclosure is intended to encompass the equivalents, means, systems, and methods of the use of the device and/or article of manufacture and its many aspects consistent with the description and spirit of the operations and functions disclosed herein. The claims of this application are likewise to be broadly construed.

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

The invention claimed is:

1. A method for designing an actual reactor for viral inactivation comprising:

introducing a process stream, including detectable particles/tracer, into an experimental reactor having a known radius of curvature and a known internal diameter, wherein the experimental reactor is in communication with at least one of a first detector and a second detector;

detecting a flow rate of the process stream in the experimental reactor by at least one of the first detector and the second detector;

detecting fluid-phase parameters of the process stream by at least one of the first detector and the second detector;

detecting the detectable particles exiting the experimental reactor by the second detector;

determining, based on the introduced process stream including the detectable particles, empirical values relating to at least one of experimental reactor parameters and fluid-phase parameters;

determining non-empirical values relating to at least one of the experimental reactor parameters and the fluid-phase parameters; and designing the actual reactor based on the determined empirical values and the determined non-empirical value;

wherein:

designing the actual reactor comprises at least one of (i)-(v): (i) scaling dimensions of the experimental reactor to the actual reactor having a same aspect ratio as the experimental reactor, but a different internal diameter; (ii) scaling the dimensions of the experimental reactor to the actual reactor having a same aspect ratio and a same internal diameter as the experimental reactor; (iii) scaling the dimensions of the experimental reactor to the actual reactor having a different aspect ratio than the experimental reactor and a different diameter than the experimental reactor; (iv) scaling the dimensions of the experimental reactor to the actual reactor having a different aspect ratio as the experimental reactor, but a same diameter as the experimental reactor;

wherein when designing the actual reactor comprises scaling the dimensions of the experimental reactor to the actual reactor having the same aspect ratio as the experimental reactor, the method:

(i) requires derivation of height equivalent of a theoretical plate ("HETP"), reactor volume, and internal diameter based on average flow velocity, utilizing equations (1a)-(1g) below:

$$HETP = \frac{\sigma_{time}^2 * L}{T_{Ave}^2} \quad (1a)$$

(1b) $HETP = f(v) = (av^3 + bv^2 + cv + d)$, wherein a, b, c, and d are based on empirical data fits for all Dean numbers $$L = \frac{1}{2} * \left(25f(v)^2 \pm 5 * \sqrt{25f(v)^4 + 4f(v)^2 T\min * v} + 2 * T\min * v\right) \quad (1c)$$

$$A = \prod r^2 = \prod \left(\frac{i.d.}{2}\right)^2 T_{Ave_{Defined}} = \frac{L}{v} = \frac{CA * L}{Q} \quad (1d)$$

$$T_{Ave_{Defined}} = \frac{CA * L}{Q} \quad (1e)$$

$$\frac{Q * T_{Ave_{Defined}}}{L * \prod} = r^2 \quad (1f)$$

$$i.d. = 2\sqrt{\frac{Q * T_{Ave_{Defined}}}{L * \prod}}. \quad (1g)$$

or (ii) requires derivation of HETP, reactor volume, and internal diameter based on reduced HETP and Dean Number, utilizing equations (2a)-(2e) below:

$$HETP = \frac{\sigma_{time}^2 * L}{T_{Ave}^2} \quad (2a)$$

$$\frac{HETP}{i.d.} = h = (aDe^3 + bDe^2 + cDe + d) = f(De) \quad (2b)$$

$$T_{Ave} = T_{min} + (n * \sigma_{max}) \quad (2c)$$

$$T_{Ave} = T_{max} - (m * (\sigma_{max})) \quad (2d)$$

$$T_{Ave} = \frac{RV}{Q} = \frac{CA * L_{T_{Ave}}}{Q} \quad (2e)$$

and wherein when designing the actual reactor comprises scaling the dimensions of the experimental reactor to the actual reactor having a same aspect ratio and a same internal diameter as the experimental reactor, the method requires derivation of at least HETP and path length, utilizing equations (3a)-(3f) below:

$$HETP = \frac{\sigma_{time}^2 * L_{T_{Ave}}}{T_{Ave}^2}; \quad (3a)$$

$$\sqrt{HETP} = f(De) = \frac{\sigma_{time} * \sqrt{L_{T_{Ave}}}}{T_{Ave}} = (aDe^3 + bDe^2 + cDe + d); \quad (3b)$$

wherein a, b, c, and d are based on empirical data fits only valid for Dean numbers ≥100

(3c) $T_{Ave}=T_{min}+(n*\sigma time)$;
(3d) $T_{Ave}=T_{max}-(m*\sigma time)$;

$$T_{Ave} = \frac{RV}{Q} = \frac{CA*L_{T_{Ave}}}{Q}; \text{ and} \quad (3e)$$

$$L_{T_{Ave}} = \frac{25*CA^2*f(De)^2 \pm 5*\sqrt{25*CA^4*f(De)^4 + 4*CA^3*f(De)^2*Q*T_{min}} + 2*CA*Q*T_{min}}{2CA^2} \quad (3f)$$

wherein:
- Π=The constant pi
- $\sigma_{max}$=The largest allowed standard deviation defined by the user
- $\sigma_{time}$=Standard deviation in units of time
- $\sigma^2_{time}$=Variance in units of time
- A=Cross sectional Area of flow path
- CA=Cross-sectional Area of flow path
- De=Dean Number
- f( . . . )=function of ( . . . )
- h=Reduced plate height
- i.d.-Internal diameter
- L=Path length
- $L_{T_{Ave}}$=Length of reactor required to provide targeted average residence time
- m=Modifying number
- n=Modifying number
- O=Flowrate
- r=Radius of the flow path
- RV=Reactor volume
- $T_{Ave}$=Average residence time
- $T_{Ave_{Defined}}$=Average residence time, user defined
- $T_{max}$=Maximum residence time
- $T_{min}$=Minimum residence time
- v=Velocity.

2. The method of claim 1, wherein the detectable particles are at least one of a viral particle and a surrogate tracer.

3. The method of claim 1, wherein the empirical values and non-empirical values are task-dependent.

4. The method of claim 1, wherein the experimental reactor parameters and the fluid-phase parameters corresponding to the empirical values and the non-empirical values are theoretical or estimated minimum residence time, theoretical or estimated maximum residence time, internal diameter, volumetric flow rate, path length of a flow path, radius of curvature, density of the process stream, dynamic viscosity, and variance.

5. The method of claim 1, wherein the empirical values are values corresponding to least one of the experimental reactor parameters and the fluid-phase parameters that are linear to an experimental set of data and wherein the non-empirical values correspond to at least one of theoretical or estimated minimum residence time, theoretical or estimated maximum residence time, internal diameter, volumetric flow rate, path length of a flow path, and radius of curvature.

6. The method of claim 1, wherein detecting the detectable particles exiting the experimental reactor further comprises determining a minimum residence time experienced by one of the detectable particles that is equivalent to an incubation time for batch viral inactivation and a maximum residence time experienced by a last significant amount of the detectable particles to exit the experimental reactor.

7. The method of claim 1, wherein the experimental reactor parameters comprise determining at least one of a minimum residence time experienced by one of the detectable particles that is equivalent to an incubation time for batch viral inactivation, a maximum residence time experienced by a last significant amount of the detectable particles to exit the experimental reactor, internal diameter of a reaction tube, volumetric flow rate, length of the reaction tube, radius of curvature, and a volume of the experimental reactor.

8. The method of claim 1, wherein the fluid-phase parameters comprises at least one of a density and a dynamic viscosity.

9. The method of claim 1, wherein designing the actual reactor comprises scaling the dimensions of the experimental reactor to the actual reactor having the same aspect ratio as the experimental reactor, and wherein the method requires derivation of HETP, reactor volume, and internal diameter, based on average flow velocity, utilizing equations (1a)-(1g).

10. The method of claim 1, wherein designing the actual reactor comprises scaling the dimensions of the experimental reactor to the actual reactor having the same aspect ratio as the experimental reactor, and wherein the method requires derivation of HETP, reactor volume, and internal diameter based on reduced HETP and Dean Number utilizing equations (2a)-(2e).

11. The method of claim 1, wherein designing the actual reactor comprises scaling the dimensions of the experimental reactor to the actual reactor having a same aspect ratio and a same internal diameter as the experimental reactor, and wherein the method requires derivation of at least HETP and path length utilizing equations (3a)-(3f).

12. The method of claim 1, wherein the experimental reactor includes a reaction tube that comprises at least one of (i) a set of alternating turns that form a serpentine pattern between an inlet and an outlet and (ii) an interwoven path.

* * * * *